United States Patent [19]

Hwang et al.

[11] Patent Number: 5,409,959
[45] Date of Patent: Apr. 25, 1995

[54] ANTITHROMBOTIC TREATMENT WITH CALIX(N)ARENE COMPOUNDS

[75] Inventors: Kou M. Hwang, Danville; You M. Qi, Sunnyvale; Su-Ying Liu, Belmont; Thomas C. Lee, San Bruno; William Choy; Jen Chen, both of Sunnyvale, all of Calif.

[73] Assignee: Genelabs Incorporated, Redwood City, Calif.

[21] Appl. No.: 928,118

[22] Filed: Aug. 6, 1992

Related U.S. Application Data

[63] Continuation-in-part of Ser. No. 792,135, Nov. 13, 1991, abandoned, which is a continuation-in-part of Ser. No. 647,720, Jan. 29, 1991, Pat. No. 5,196,542, and a continuation-in-part of Ser. No. 647,469, Jan. 29, 1991, Pat. No. 5,166,173.

[51] Int. Cl.$^6$ .............................................. A61K 31/05
[52] U.S. Cl. ..................................... 514/732; 514/680
[58] Field of Search ............... 514/130, 143, 510, 562, 514/569, 577, 602, 709, 732, 680

[56] References Cited

U.S. PATENT DOCUMENTS 4,443,477 4/1984 Witte et al. ......................... 424/319

FOREIGN PATENT DOCUMENTS 721103 1/1978 U.S.S.R. .
WO91/07183 5/1991 WIPO .

OTHER PUBLICATIONS

Akerfeldt, S., et al., "Aromatic Sulfonic Acids as Viral Inhibitors. Structure–Activity Study using Rhino, Adeno 3, Herpes Simplex, and Influenza Viruses," J. Med. Chem. 14(7):596–600 (1971).

Manabe, O., and Shinkai, S., "Calixarene derivatives," abstract from Chem. Abst. 105:568 (1986).

Poh, B.-L., et al., "Complexations of Metal Cations with Cyclotetrachromotropylene in Water and Methanol," Tetrahedron 46(12):4379–4386 (1990).

Poh, B.-L., and Lim, C. S., "Complexations of Amines with Water–Soluble Cyclotetrachromotropylene," Tetrahedron 46(10):3651–3658 (1990).

Poh, B.-L., et al., "A Water–Soluble Cyclic Tetramer from Reacting Chromotropic Acid with Formaldehyde," Tetra. Letters 30(8):1005–1008 (1989).

Shinkai, S., et al., "Selective adsorption of uranyl ion ($UO_2^{2+}$) to a polymer resin immobilizing calixarene–based uranophiles," absract from Chem. Abst. 109:35 (1988).

Shinkai, S., et al., "Synthesis and inclusion properties of neutral water–soluble calixarene," abstract from Chem. Abst. 113:666 (1990).

Shinkai, S., et al., "New Syntheses of Calixarene-p-sulfonates and p-Nitrocalixarenes," J. Chem. Soc. Perkin Trans. I:2297–2299 (1987).

Shinkai, S., et al., "Hexasulfonated Calix[6]arene Derivatives: A New Class of Catalysts, Surfactants, and Host Molecules," J. Am. Chem. Soc. 108:2409–2416 (1986).

Shinkai, S., et al., "New Water–Soluble Host Molecules Derived From Calix[6]arene," Tetra. Letters 25(46):5315–5318 (1984).

Kawasaki, M., "Spot prevention in silver halide photographic material," *Chemical Abstracts* 117(16): abstract no. 160793y (1992).

Primary Examiner—Raymond Henley, III
Assistant Examiner—Russell Travers
Attorney, Agent, or Firm—Peter J. Dehlinger; Carol A. Stratford; Vincent M. Powers

[57] ABSTRACT

A method of inhibiting thrombus formation in a mammalian subject. The method involves administering to the subject a therapeutically effective dose of a calix-(n)arene compound derivatized, at its ring positions meta to the bridge attachments to the ring, with polar substituents having terminal sulfonate groups, including esters and amides which are cleavable in vivo.

9 Claims, 30 Drawing Sheets

+ R'-CHO ⟶

III                         IV

+

III                         V

LXI → LXII

LXIII → LXIV

LXV → LXVI

LXVII → LXVIII

LXIX → LXX

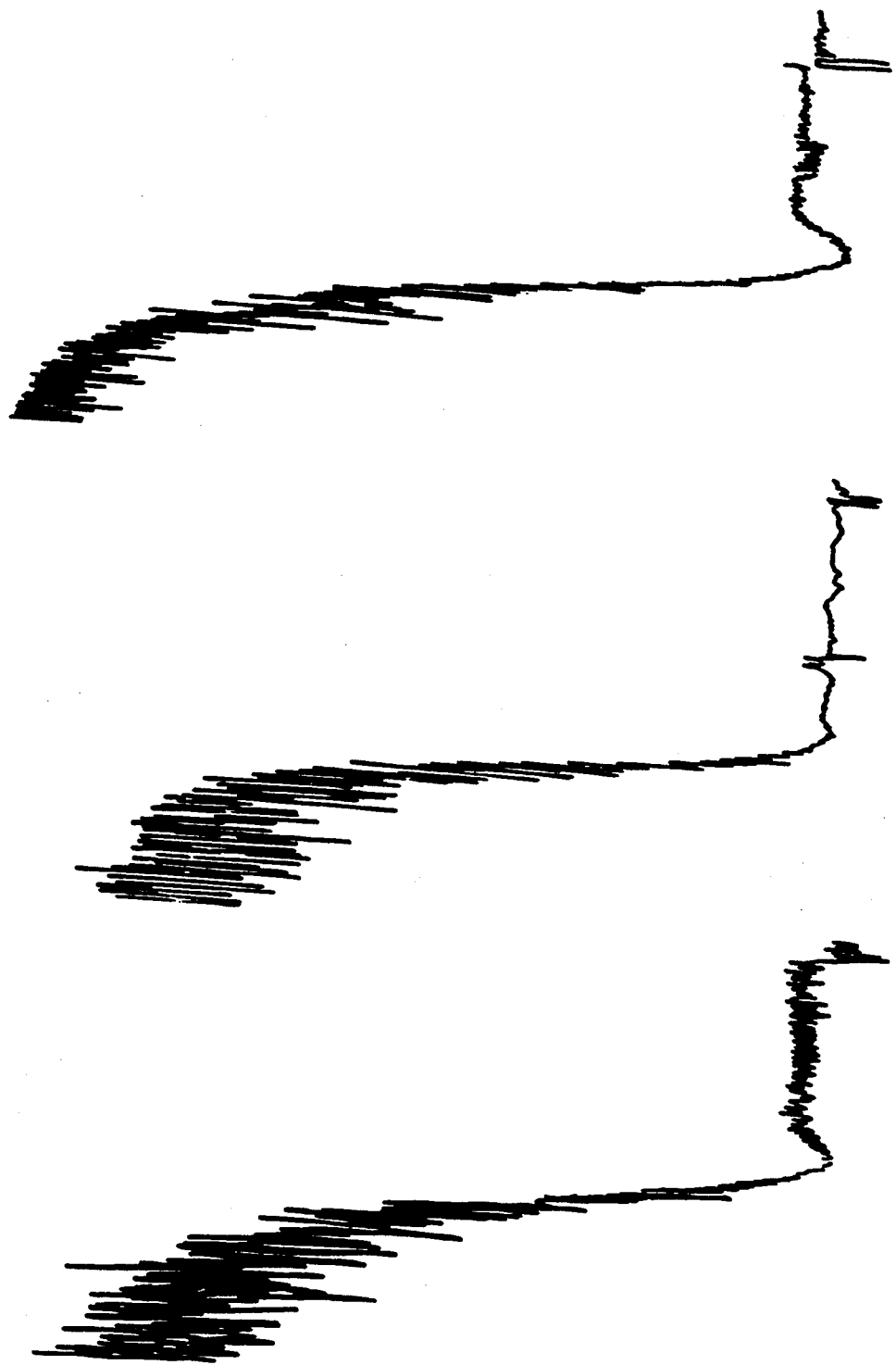

ANTITHROMBOTIC TREATMENT WITH CALIX(N)ARENE COMPOUNDS

This application is a Continuation-in-Part of U.S. patent application for "Anticoagulant Properties of Macrocyclic Compounds and Method of Treatment" Ser. No. 07/792,135, filed Nov. 13, 1991, now abandoned, which is a Continuation-in-Part of U.S. patent applications for "Macrocyclic Anti-Viral Compound and Method" Ser. No 07/647,720, filed Jan. 29, 1991, now U.S. Pat. No. 5,196,452, and for "Method of Treating Herpes Simplex Virus Infection", Ser. No. 647,469 (Allowed), filed Jan. 29, 1991.

FIELD OF THE INVENTION

The present invention relates to methods of inhibiting blood coagulation to prevent venous and arterial thrombosis using calix(n) arene compounds.

References

Almi, M., Arduini, A., Casnati, A., Pochini, A., and Ungaro, R. (1989) Tetrahedron 45, 2177–2182.

Andriuofi, G. et al. (1990) Hemostasis 20 (suppl. 1): 154–158.

Arduini A., Pochini, A., Rizzi, A., Sicuri, A. R., and Ungaro, R. (1990) Tet. Lett. 31, 4653–4656.

Baboir, B. M. and Stossel, T. P. (1984) *Hematology: A Pathophysiological Approach*. Churchill Livingstone, New York, pp.171–189.

Brown, B. A. (1988) *Hematology: Principles and Procedures*. Lea & Febiger, Philadelphia, pp. 204–254.

Cade, J. F. et al. (1884) Thrombosis Research 35: 613–625.

Caramazza, I. et al. (1991) Thrombosis Research 62:785–789.

de Mendoza, J., Nieto, P. M., Prados, P., and Sanchez, C. (1990) Tetrahedron 46, 671–682.

Fareed, J. et al. (1985) Seminar Thromb. Hemostat. 11: 115–175.

Gormer, B., et al. (1990) Makromol. Chem. 191, 81–87.

Gutsche, C. D. (1991) "Single Step Synthesis and Properties of Calixarenes", in Calixaranes—a Versatile Class of Macrocyclic Compounds, Vicens, J., and Bohmer, V. Editors, Kluwer Academic Publishers, Dordrecht, The Netherlands, pp. 1–37.

Gutsche, C. D., and Nam, K. C. (1988) J. Am. Chem. Soc. 110, 6153–6162.

Gutsche, C. D., Dhawan, B., Levine, J. A., No, K. H., and Bauer, L. J. (1983) Tetrahedron 39, 409–426.

Gutsche, C. D., and Lin, L-G. (1986) Tetrahedron 42, 1633–1640.

Gutsche, C. D., Levine, J. A., and Sujeeth, P. K. (1985) J. Org. Chem. 50, 5802–5806.

Hirao, T., Masunaga, T., Yamada, N., Ohshiro, Y., and Agawa, T. (1982) Bull. Chem. Soc. Jpn. 55, 909–913.

Majerus, P. W. et al. (1990) in *Goodman and Gilman's The Pharmaceutical Basis of Therapeutics* (Gilman, A. G. et al., eds.) Pergamon Press, New York, Chap. 55: 1311–1331. Morita et al. (1989) Chem. Lett., p. 1349–.

No et al. (1986) Bull. Kor. Chem. Soc. 7, 442.

Powers, L. W. (1989) *Diagnostic Hematology: Clinical and Technical Principles*. C. V. Mosby Co. St. Louis, pp. 135–143.

Schaefer, J. P., Higgins, J. G., and Shenoy P. K. (1973) Org. Synth., Coll. Vol. V, 249.

Shinkai, S., et al. (1987) J. Chem. Coc. Perkin Trans. I, 2297–2299.

Shinkai, S., et al. (1989) J. Chem. Soc. Perkin Trans. I, 2039–2045.

Weinelt, F., and Schneider, H-J. (1991) J. Org. Chem. 56, 5527–5535.

Yilmaz, M., and Vural, U. S. (1991) Synth. React. Inorg. Met. Org. Chem. 21, 1231–1241.

BACKGROUND OF THE INVENTION

Blood coagulation or clotting is the result of a complex series of biochemical reactions. In the normal course of events, hemostasis and the associated process of blood coagulation prevent undue loss of blood from an injured blood vessel. However, inappropriate coagulation of blood (thrombosis) may occur within the circulatory system in pathological states such as atheroschlerosis or in response to a variety of insults, including surgery and implantation of medical devices. Such inappropriate clotting results in thrombus formation, which may cause occlusion of a vessel and/or thromboembolism, in which all or part of a blood clot breaks loose and becomes lodged as an embolus in another region of the circulatory system. Such emboli are, in some cases, life-threatening, especially when they cause obstruction of the pulmonary or cerebrovascular circulatory system.

Prevention of thrombosis is considered a crucial part of the treatment regimen for patients at risk for developing thrombi. Disease or treatment states in which antithrombotic therapy is indicated include replacement of heart valves, grafting procedures, chronic bedrest, surgery, venous thrombosis and pulmonary embolism, arterial embolism, stroke, presence of abnormal coagulation factors, certain stem cell diseases, and homocystinuria.

In order to understand the various means by which blood coagulation, and, consequently, thrombosis, can be controlled, a basic understanding of the cascade of reactions leading to formation of fibrin and blood clots within the circulatory system is essential. These reactions and their components have been reviewed extensively (Majerus,Baboir) and will be only summarized briefly with reference to FIG. 29 herein.

Coagulation of blood can be stimulated by either of two different, but interconnected pathways—the intrinsic and extrinsic pathways. In both pathways, blood coagulation results from a series of zymogen activation steps involving enzymatic cleavage of the inactive zymogen molecule to an active protease, which, in turn, activates the next enzyme in the pathway. With reference to FIG. 29, the linking point between the intrinsic and extrinsic pathways is activation of the zymogen Factor IX to the active protease, Factor IXa.

The intrinsic pathway is so called, because, following the initial contact stimulus, only factors intrinsic to the blood are involved in its functioning. In this pathway, as studied in vitro, interaction of Factor XII, prekallikrein, and high molecular weight kininogen with a foreign surface, such as glass or kaolin, results in conversion of Factor XII to Factor XIIa, which in turn activates Factor IX to Factor IXa.

Factor IXa is a protease which converts inactive Factor X to active Factor Xa. This conversion is accelerated by the presence of platelets or phospholipids (both designated PL in the figure), cofactor VIIIa, and calcium. The conversion of Factor II (prothrombin) to form Factor IIa (thrombin) is enhanced by the presence of platelets or phospholipids, factor Va, and calcium. Factor Va can be released by stimulated platelets.

Thrombin is a protease which cleaves the high molecular weight fibrinogen to fibrin monomers. These monomers form a gel, to which red blood cells adhere to form a blood clot. The strength of the clot is increased by the fibrin monomer interchain transglutamination reactions, catalyzed by factor XIIIa.

To complete the common pathway shown in FIG. 29, clots are broken down ("dissolved") by an endogenous fibrinolytic system. The active protease plasmin is formed from inactive plasminogen by enzymatic cleavage catalyzed in vivo by one or more of a number of endogenous activators, including tissue plasminogen activator (t-PA). Streptokinase, a bacterial product, or urokinase, isolated from human cells, are also capable of activating plasminogen. Plasmin non-specifically cleaves fibrin and other plasma proteins, including some of the clotting factors.

In the extrinsic pathway, exposure of blood to a tissue factor is the stimulus for conversion of Factor IX to Factor IXa. Tissue Factor is a lipoprotein present on surfaces of non-circulatory cells, such as fibroblasts or smooth muscle cells to which the blood may be exposed in certain pathological states. As shown in FIG. 29, Factor VIIa, in the presence of calcium, effects the conversion of Factor IX to Factor IXa as well as the conversion of Factor X to Factor Xa. Factor VII itself has about 1/100 the proteolytic activity of Factor VIIa, and is therefore able to initiate clotting. Tissue factor increases the activities of both Factor VII and Factor VIIa about 30,000 fold. Formation of Factor Xa, also accelerates the process by converting still more Factor VII to Factor VIIa.

In general, agents which affect blood hemostasis fall into three categories: agents which interfere with portions of the above-described coagulation cascade (anticoagulants), agents which interfere with platelet activation and aggregation (antiplatelet drugs), and agents which promote disintegration of blood clots (thrombolytics). Anticoagulants and antiplatelet drugs are categorized as antithrombotics, used in preventing and arresting thrombus formation in arterial and venous blood vessels, as described above. Antiplatelet agents interfere with the initial stages of platelet aggregation initiated by contact of platelets with collagen, such as occurs during blood vessel damage. These agents are used clinically in prophylaxis of arterial thromboses, such as occur in atheroschlerosis. Anticoagulant compounds, by interfering with the clotting cascade, inhibit those components of clot formation associated with fibrin deposition, and are more generally used in prevention of venous thromboses. Thrombolytic agents are used in dissolution of formed thrombi in both venous and arterial vessels.

Aspirin, dipyridamole and ticlopidine are examples of antiplatelet drugs. These agents are generally used in prophylaxis of arterial thrombus formation as in atherosclerotic disease, repeat myocardial infarction, transient ischemic attack, and alone or in association with anticoagulants in certain cardiac valvular disorders. They are not generally used in the treatment of other abnormal clotting events, such as venous thrombosis, nor is there considered to be a mechanistic basis for their use in such disorders.

Agents which promote disintegration of blood clots (fibrinolytic agents) include tissue plasminogen activator, streptokinase and urokinase. These compounds are used post-myocardial infarction to prevent thromboembolism.

Currently available anticoagulant drugs are limited to the heparin-like compounds, which are active only when given intravenously, and to the oral coumarin anticoagulants. Heparin is an endogenous glycosaminoglycan which serves as a catalyst for the reaction between antithrombin and various activated factors in the coagulation cascade (Factors IXa, Xa, XIa, XIIa, kallikrein and thrombin). This reaction results in inhibition of these factors, and thus inhibition of coagulation. Heparin is not well absorbed orally and has a relatively short half-life in the bloodstream. Side effects of long term heparin therapy can include thrombocytopenia with associated paradoxical arterial thrombosis, and, rarely, osteoporosis. Overdosage with heparin can be antagonized by injection of protamine sulfate.

Oral anticoagulants, including warfarin and other coumarin derivatives, produce their effects on blood coagulation by indirect means. These compounds inhibit regeneration of vitamin K in the liver. Vitamin K is a precursor to several of the coagulation pathway factors, including Factors II (prothrombin), VII, IX, and X; therefore, depletion of vitamin K results in inhibition of coagulation. As might be expected from their mechanism, the coumarin drugs have a relatively long onset of therapeutic activity, since their effectiveness is dependent upon depletion of endogenous depots of active vitamin K. Coumarin therapy requires careful management, due to a number of drug and nutritional interactions which serve increase or decrease effective dosage levels. Treatment with coumarin derivatives is also associated with several serious side effects including bleeding episodes and teratogenicity.

A number of analytical tests have been devised to measure the patency of the above-described coagulation cascade. These tests, which are described in more detail below, are generally carried out on blood plasma. Specific assays have been developed to distinguish the particular sites of activity of the various compounds in the clotting cascade and to distinguish between their overall anticoagulant effects and their antithrombotic activity. For example, the prothrombin time assay (PT) measures the extrinsic system of coagulation and is therefore used to detect deficiencies in factors II, V, VII, and X. PT is also used to monitor therapy in patients receiving coumarin anticoagulants, since factors II and VII are among those which are dependent upon vitamin K. The activated partial thromboplastin time assay (APTT) measures coagulation factors present in the intrinsic system of coagulation and is generally used to monitor heparin therapy. Antiplatelet activity can be measured directly in plasma samples.

As described above, current anticoagulant regimens include treatment with various forms of heparin, or coumarin drugs. Of the two, the heparin drugs are by far the better tolerated and are easier to titrate. However, the usefulness of these compounds is limited by their currently obligatory intravenous route of administration. Although formulations of these compounds have been administered enterally, anticoagulant activity has been observed only after intraduodenal administration (Andriuoli, Caramazza).

Coumarin drugs such as warfarin can be given orally; however, the usefulness of these drugs is limited by their relatively long onset time, difficulty in titration, interactions with other drugs, and side-effects, as described above. In addition, both heparin and coumarin drugs are limited in their usefulness by their hemorrhagic potential, because effective antithrombotic doses of these drugs also concomitantly produce excessive systemic anticoagulation.

It is therefore a general object of the present invention to provide compounds and methods for oral anticoagulant therapy with a shorter onset and duration of action, for improved oral antithrombotic activity. A further object of the invention is to provide antithrombotic agents having reduced hemorrhagic effects, at antithrombotic doses.

SUMMARY OF THE INVENTION

The present invention includes a method of inhibiting thrombus formation in a mammalian subject. The method includes administering to the subject, a therapeutically effective dose of a calix(n)arene compound which is derivatized, at its ring positions meta to the bridge attachments to the ring, with polar substitutents having terminal carboxylate, phosphate, or sulfonate groups.

In one general embodiment, the calix(n)arene has the general structure:

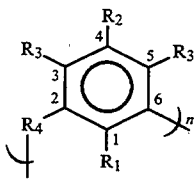

wherein (a) n=4, 6, or 8, (b) $R_2$ is a polar substitutent with a terminal carboxylate, phosphonate, or sulfonate group, including cleavable esters and amides thereof. $R_1$ is preferably OH, or in a partially oxidized form of the compound, a combination of OH and =O. $R_3$ is preferably H, and $R_4$ is preferably $CH_2$, or in the partially oxidized form just mentioned, a combination of $CH_2$ and $\geq CH$.

In a more specific embodiment, $R_2$ has the form: $(CH_2)_m R_2'$, where m=1–3, and $R_2'$ is a sulfonate group, including a sulfonate ester or amide of a lower alkyl group.

In another embodiment, $R_2$ has the form: $(CH_2)_m—R_2'$, where m=0–3, and $R_2'$ is a carboxylate group, including a carboxylate ester or amide of a lower alkyl group.

In yet another embodiment, $R_2$ has the form: $(CH_2)_m—R_2'$, where m=0–3, and $R_2'$ is a phosphonate group, including a phosphonate ester or amide of a lower alkyl group.

In another aspect, the invention contemplates novel calix(n)arene compounds of the type described above, and having sulfonate, phosphonate, and carboxylate terminal groups.

In yet another aspect, the invention contemplates a method of inhibiting thrombus formation using compounds of the type described above, wherein the compounds have minimal hemorrhagic potential.

These and other objects and features of the invention will become more fully apparent when the following detailed description of the invention is read in conjunction with the accompanying drawings.

BRIEF DESCRIPTION OF THE DRAWINGS

FIG. 38 A shows a composite plot of varying concentrations of KY-1 on clotting times measured as PT, TT, APTT, and AT;

FIG. 38B shows a composite plot of varying concentrations of Y-1 on clotting times measured as PT, TT, APTT, and AT;

DETAILED DESCRIPTION OF THE INVENTION

I. Definitions

Figure 1:
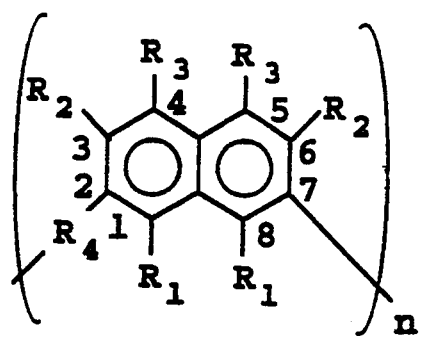
FIG. 1 shows the general structure of a macrocyclic compound composed of naphthalene subunits, for use in the present invention.

The terms defined in this section have the following meanings unless otherwise indicated.

"Anticoagulant activity" refers to the inhibition of the normal blood coagulation or clotting process, exhibited as prolongation of the time required to form a fibrin aggregate or clot, as measured by one or more standard in vitro clotting assay. Phrases which are essentially synonymous with "anticoagulant activity" include "inhibit coagulation" and "prevent coagulation."

"Antithrombotic activity" refers to the inhibition of blood clotting activity and/or platelet aggregation which leads to thrombus formation in the blood vessels under certain pathological conditions. In the context of the present invention, "antithrombotic activity" and synonymous terms such as "inhibition of thrombus formation" encompass maneuvers effective to inhibit thrombus formation.

"Antiplatelet activity" refers to inhibition of platelet aggregation.

An "aryl ring" subunit is a single ring or fused ring structure containing at least one aromatic ring, i.e., a 5- or 6-member ring with 6 pi electrons necessary for aromaticity. Examples include benzene, naphthalene, fused ring structures, such as tetralin, and heterocyclic structures, including fused-ring structures, such as quinoline, isoquinoline, and indole.

A "macrocyclic compound composed of aryl ring subunits" is a cyclic compound formed by linking ring atoms in aryl ring subunits to form a cyclic chain.

A "calix(n)arene" or "calixarene compound" is a macrocyclic compound having a skeletal structure of the form:

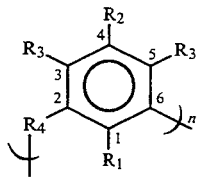

where n is preferably 4–10.

The "positions of bridge attachments to the ring" in a calixarene compound refer to ring positions 2 and 6 in each ring of the compound.

The "non-bridge positions" in a calixarene compound refer to ring positions 1, 3, 4, and 5 in each ring of the compound.

The "ring position meta to the bridge attachments" in a calixarene compound refer to ring position 4 in each ring of the compound.

A "polar substituent" refers to a radical R whose octanol/water partition coefficient is less than 1.

A "polar substitutent having a terminal carboxylate, phosphonate, sulfonate, or sulfinate refers to R having the form $-CO_2^{31}$ or $R'-CO_2^{31}$ (carboxylate), $-PO_3^{31}$ or $R'-PO_3^-$ (phosphonate), $-SO_3^-$ or $R'-SO_3^-$ (sulfonate), $-SO_2^-$ or $R'-SO_{2-}$ (sulfinate), where R' is a linear chain 1–4 atoms in length which is effective to link the associated carboxylate, phosphonate, or sulfonate group to the phenyl ring of calixarene. One preferred R' linear chain is $(CH_2)_m$, where m=1–3.

A "carboxylate" group includes the carboxylic acid group $-CO_2^-$, carboxylate salts, and carboxylic acid esters and amides which are cleavable in vivo. A carboxylic acid ester has the general form $-CO_2-R$, where R is an unsubstituted lower alkyl or a substituted alkyl, and a carboxylic acid amide has the general form $CONR'R''$, where $NR'R''$ is a secondary or tertiary amine, i.e., R' and R' are H or lower substituted or unsubstituted lower alkyl groups. A carboxylic acid ester or amide is cleavable in vivo if it is hydrolysed by serum esterases or amidases, respectively, to the corresponding carboxylic group.

A "phosphonate" group includes the phosphonic acid group $-PO_3^{-2}$, including phosphonate salts, and phosphonic acid esters and amides which are cleavable in vivo. A phosphonic acid ester has the general form $-PO_3-RR'$ where R and R' are lower alkyl groups, or substituted lower alkyl groups, and a phosphonic acid amide has the general form $PO(NRR')_2$, where NRR' is a secondary or tertiary amine, where R and R' are as above. A phosphonic acid ester or amide is cleavable in vivo if it is hydrolysed by serum phosphatases or phosphoamidases, respectively, to the corresponding sulfonic acid group.

A "sulfonate" group includes the sulfonic acid group $-SO_3^-$, including sulfonate salts, and sulfonic acid esters and amides which are cleavable in vivo. A sulfonic acid ester has the general form $-SO_3R$, where R is an unsubstituted lower alkyl or substituted lower alkyl group, and a sulfonic acid amide has the general form $SO_2NR'R''$, where $NR'R''$ is a secondary or tertiary amine. A sulfonic acid ester or amide is cleavable in vivo if it is hydrolysed by serum esterases or sulfoamidases, respectively, to the corresponding sulfonic acid group.

A "lower alkyl group" is a linear or branched alkyl group containing 1-5 carbon atoms.

A "substituted lower alkyl group" is a lower alkyl group having one or more substitutions at its carbon atoms.

II. Preparing Aryl-Subunit Macrocyclic Compounds

This section describes the synthesis of two general types of aryl macrocyclic compounds which are useful in the anti-thrombus treatment method of the invention. The first type is composed of naphthalene subunits with sulfonic acid-derived substituents, and is the subject of earlier filed patent applications Ser. Nos. 07/791,920, 07/647,720, and 647,469. Synthesis of these compounds in described in Section A herein. The second general type, and the one which is the subject of the present application, is a calix(n)arene compound which is derivatized, at its ring positions meta to the bridge attachments to the ring, with polar substitutents having terminal carboxylate, phosphate, or sulfonate groups. Synthesis of these compounds are described in Sections B and C. From the synthetic routes given in the two sections, it will be apparent how macrocycles composed of mixed subunits, e.g., both naphthalene and calix(n)arene phenyl subunits can be prepared. The synthetic methods are also generally applicable to macrocycles composed of heterocyclic subunits with sulfonic acid-derived substituents.

A. Macrocyclic Compounds with Substituted Naphthalene Subunits

Figure 2A:
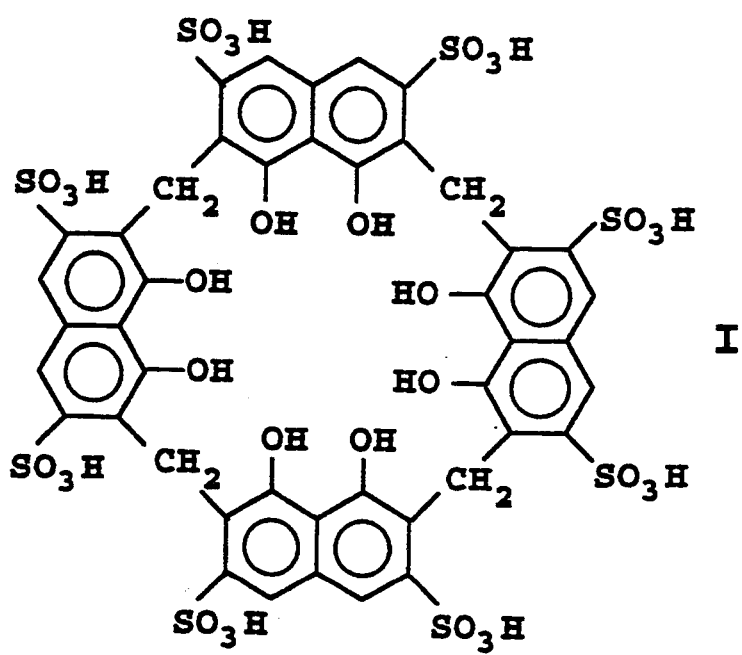
FIGS. 2A and 2B show non-oxidized (2A) and partially oxidized (2B) forms of the FIG. 1 structure, where n=4 and the subunit is chromotropic acid.

FIG. 1 shows the general structural formula of a macrocyclic compound composed of substituted naphthalene subunits, for use in the present invention. One exemplary compound of this type is shown in non-oxidized (I) and partially oxidized (II) form in FIGS. 2A and 2B, respectively. The compound is a tetramer of chromotropic acid (1,8-dihydroxy, 3,6-disulfonic acid naphthalene) subunits linked by methylene or methene ($>CH_2$ or $\geq CH$) bridges ($R_4$). As seen, the methylene bridges and the "interior" ring atoms (ring positions 1, 2, 7, and 8) form a continuous chain having attached $R_1=OH$ or $=O$ groups attached at the 1 and 8 positions. The non-chain atoms (ring positions 3-6 on each substituent) have $R_2$=sulfonic acid substituents on the 3 and 6 ring atoms. The nature of the partially oxidized structure was deduced from $H^1$ and $C^{13}$ NMR studies, and from mass spectroscopy evidence.

Figure 2B:
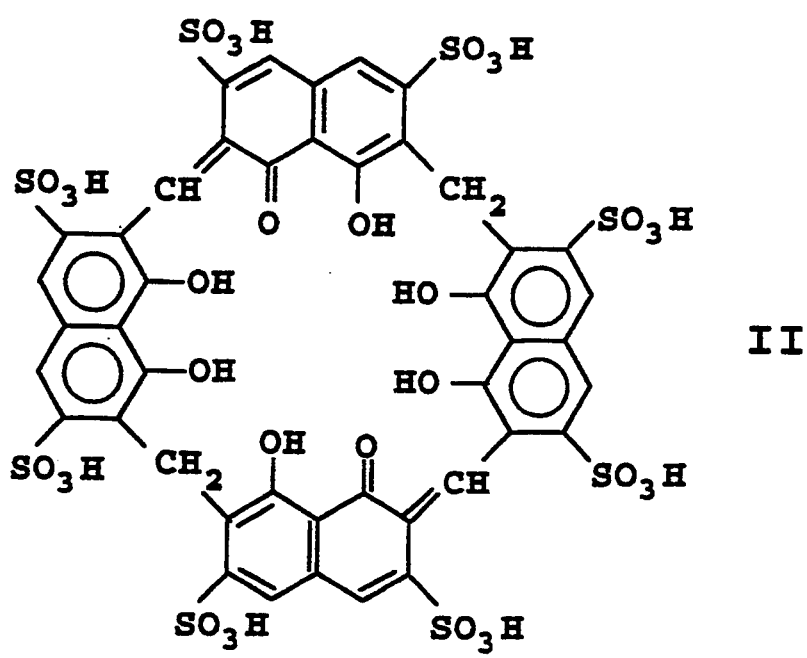

For purposes of the following discussion, and for illustrating synthetic routes, usually only the non-oxidized subunit form of the compound is given. It will be understood that the compound may be partially oxidized, after exposure to air under heat and acidic conditions, i.e., contain one or more $R_1$ ketone ($=O$) groups, and a double bond between the ring and the associated bridge methylene group, as indicated in FIG. 2B. It will also be understood that the same reaction mechanisms will apply generally to the partially oxidized form of the compound, i.e., the structure shown in FIG. 2B, or similar structures containing additional $R_1=O$ groups, except that $R_1$ modification reactions will typically selectively modify an $R_1$ $-OH$ group, and leave the corresponding $R_1 = O$ group intact. As will be seen below, the compound preferably includes the chromotropic acid derivatives in which $R_1$ is a polar substituent, such as OH, $=O$, $CO_2H$ or an ether, thioether, ester, or thioester linked alkyl or aryl group, and combinations of these group, e.g., where only the OH groups in the partially oxidized structure are substituted by one of the above groups.

$R_2$, as noted, is a sulfonic acid-derived substituent which may be sulfonic acid, as shown in FIG. 2, a sulfonate salt, sulfinic acid ($-SO_2H$), and sulfinate salts, a sulfinate or sulfonate ester, or sulfonamides. $R_3$ is H or Br or other halogen. Also as will be seen below, the $R_4$ bridge linking the chromotropic acid derivative subunits is preferably of the form $>CHR$ or $\geq CR$ (indicating unsaturated bridges in the partially oxidized form), where R is H or a small carbon-containing group, such as lower alkyl, alkenyl, ketone, or carboxylic acid group, or aryl group. The bridge may also be of the form $-CH_2NR'CH_2-$, where R' is similarly H or a small carbon containing group, such as a lower alkyl group.

Alternatively, the bridges in the macrocycle may be ring structures, including aryl ring structures, such as in the dimeric macrocycle shown in FIG. 4, or analogous structures formed by bridging through heterocyclic rings, such as pyrole or furan rings.

The number of subunits may vary from 4 to 8, with macrocycles containing 4, 6, and 8 subunits being preferred. In the reaction schemes described below, the macrocycle formed may include mixtures of compounds with different subunit numbers (n) values, e.g., a dominant n=4 structure (4 subunits) with additional structures containing 6 and 8 subunits.

Representative macrocyclic compounds which have been synthesized and tested for antithrombotic activity are identified by their $R_1$, $R_2$, $R_3$, and $R_4$ substituents in Table 1 below. The KY and Y number in the lefthand column in the table refers to the analog designation of the corresponding compound. For example, the compound in which $R_1$ is OH, $R_2$ is $SO_2NH_2$, $R_3$ is H, and $R_4$ is —$CH_2$— is designated KY-3. Although not shown in the table, the compounds may exist in a partially oxidized state in which one of more $R_1$ groups are =O, and adjacent bridges contain a double-bond carbon linkage to the ring.

acrolein; and KY-110, in the presence of pyruvic aldehyde. It will be appreciated that a variety of other RCHO aldehydes having small alkyl, alkenyl, acid and other hydrocarbon R groups would be suitable. Further, the R bridge group may be further modified after

TABLE 1

| KY | $R_1$ | $R_2$ | R3 | $R_4$ |
|---|---|---|---|---|
| KY-1 | OH | $SO_3Na$ | H | >$CH_2$ |
| KY-3 | OH | $SO_2NH_2$ | H | >$CH_2$ |
| KY-42 | OH | $SO_3Na$ | H | >$CHCO_2H$ |
| KY-48 | OH | $SO_3Na$ | H | >$CHCHOHCH_2OH$ |
| KY-85 | OH | $SO_3Na$ | OH | >$CHC_6H_6$ |
| KY-97 | OH | $SO_3Na$ | H | >$CH_2CH=CH_2$ |
| KY-110 | OH | $SO_3Na$ | H | >$CHC(O)CH_3$ |
| KY-121 | OH | $SO_2C_6H_3(OH)_2$ | H | >$CH_2$ |
| KY-123 | OH | $SO_3Na$ | H | >$CH_2$ |
| KY-143 | OH | $SO_3Na$ | OH | >$CH_2$ |
| KY-147 | OH | $SO_2NHCH_3$ | H | >$CH_2$ |
| KY-148 | OH | $SO_2NHEt$ | H | >$CH_2$ |
| KY-151 | $OCH_3$ | $SO_3Na$ | H | >$CH_2$ |
| KY-158 | OH | $SO_2CH_3$ | H | >$CH_2$ |
| KY-171 | OH | SH | H | >$CH_2$ |
| KY-175 | OH | $SO_3CH_3$ | H | >$CH_2$ |
| KY-176 | OH | $SO_2NHC_6H_5$ | H | >$CH_2$ |
| KY-193 | OH | $SO_3Na$ | Br | >$CHBrCH_{2Br}$ |
| KY-194 | OH | $SO_3Na$ | Br | >$CH_2$ |
| KY-270 | $OCOCH_3$ | $SO_3Na$ | H | >$CH_2$ |
| KY-272 | $OCOCH_3$ | $SO_3Na$ | H | >$CHCO_2H$ |
| KY-276 | OCOEt | $SO_3Na$ | H | >$CH_2$ |
| KY-277 | COEtCl | $SO_3Na$ | H | >$CH_2$ |
| KY-280 | $OCH_3$ | $SO_3Na$ | H | >$CH_2$ |
| KY-281 | $OCOC_3H_7$ | $SO_3Na$ | H | >$H_2$ |
| KY-284 | $OCH_3$ | $SO_3Na$ | H | >$CHCO_2H$ |
| KY-285 | $OCOCH_3$ | $SO_3Na$ | H | >$CH_2$ |
| KY-288 | OCOPr | $SO_3Na$ | H | >$CH_2$ |
| KY-289 | $OCOC_4H_9$ | $SO_3NH_4$ | H | >$CH_2$ |
| KY-290 | OCOBu | $SO_3Na$ | H | >$H_2$ |
| KY-291 | $OCOC_5H_{11}$ | $SO_3NH_4$ | H | >$CH_2$ |
| KY-293 | $OCOCH=CHCH_3$ | $SO_3NH_4$ | H | >$CH_2$ |
| KY-294 | $OCO(CH_2)_6CO_2H$ | $SO_3NH_4$ | H | >$CH_2$ |
| KY-307 | $O(CH_2)_5CO_2H$ | $SO_3NH_4$ | H | >$CH_2$ |
| KY-346 | OH | $SO_3Na$ | H | —$CH_2N(CH_3)CH_2$— |
| KY-352 | OH | $SO_3NHC_6H_{11}O_5$ | H | >$CH_2$ |
| KY-357 | OH | $SO_2NHCH_2CO_2Na$ | H | >$CH_2$ |
| KY-359 | OH | $SO_2NHOH$ | H | >$CH_2$ |
| KY-395 | $OCH_3$ | $SO_3Na$ | H | —$CH_2N(CH_3)CH_2$— |
| KY-397 | $OCH_3$ | $SO_2NH_2$ | H | >$CH_2$ |
| KY-398 | $OCH_3$ | $SO_2NHCH_2CO_2H$ | H | >$CH_2$ |
| KY-399 | $OCH_3$ | $SO_2NHCH_2CO_2H$ | H | —$CH_2N(CH_3)CH_2$— |
| Y-20 | OH | $SO_3Na$ | H | —$CH_2C_4H_2OCH_2$— |
| Y-34 | OH | $SO_3Na$ | H | —$CH_2C_6H_4CH_2$— |
| Y-66 | OH | $SO_3Na$ | H | >$CHCO_2H$— |
| KYY-19 | OH | $SO_2NHCH(CH2CO_2H)_2$ | H | >$CH_2$ |

Figure 3A:
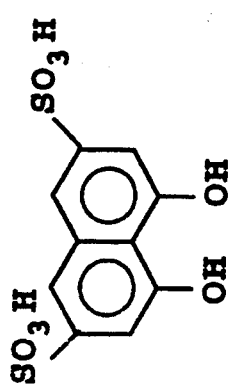
FIGS. 3A and 3B illustrate two general methods of synthesis of a macrocyclic compound like the one shown in FIG. 2A.
Figure 3A:
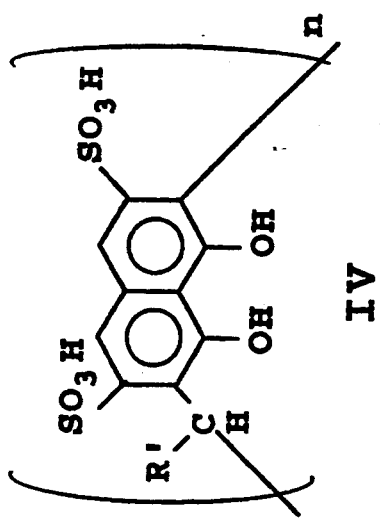
Figure 3B:
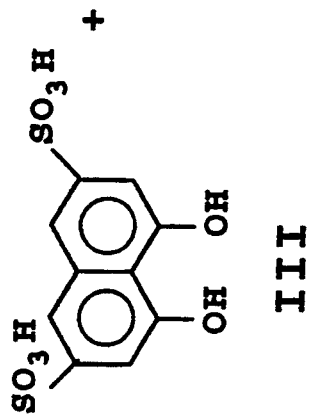
Figure 3B:
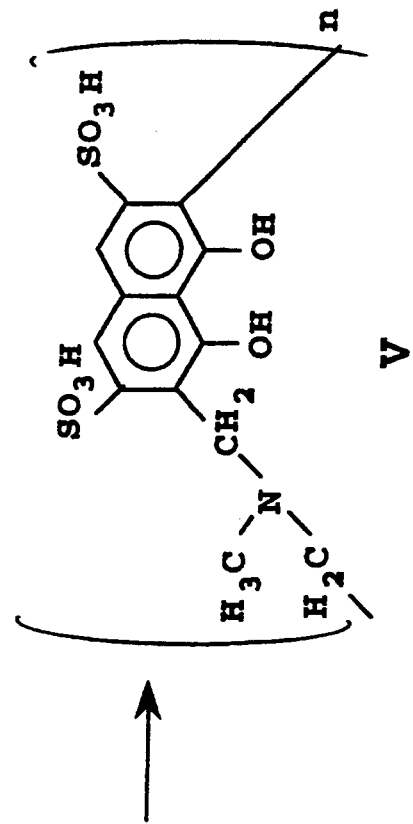

FIGS. 3A and 3B illustrate two preferred synthetic methods for preparing macrocyclic chromotropic acid compounds. The method illustrated in FIG. 3A involves cyclization of a chromotropic acid derivative (including chromotropic acid itself) with an aldehyde (RCHO) to form a macrocyclic compound, such as the tetramer shown FIG. 2, in which the chromotropic acid subunits are linked by R-substituted methylene groups, i.e., in which $R_4$ is >CHR (including ≧CR). This synthetic scheme provides a convenient method for constructing macrocyclic compounds having a variety of different bridge-methylene R groups, by carrying out the cyclization reaction in the presence of an aldehyde of the form RCHO.

For example, to construct a macrocyclic compound with a >$CH_2$ bridge, such as the KY-1 compound (IV), chromotropic acid (III) is reacted with formaldehyde. Typical reaction conditions are given in Example 1A for the synthesis of KY-1. Similarly, KY-42 is prepared by cyclization with glyoxylic acid (Example 1C); KY-48, in the presence of glyceraldehyde; KY-85, in the presence of benzaldehyde; KY-97, in the presence of the cyclization reaction. For example, KY-193 may be prepared by bromination of the KY-97 compound.

In the method illustrated in FIG. 3B, cyclization of the chromotropic acid derivatives (III) is carried out by reaction with hexamethylenetetramine, to form a 3-atom chain bridge of the type —$CH_2N(CH_3)CH_2$— (V). The cyclization reaction for the synthesis of KY-346 is given in Example 1J. The —$CH_2N(CH_3)CH_2$— bridge may be modified, after the cyclization reaction, to form a variety of N-substituted bridges of the —$CH_2N(R')CH_2$—, where R' is one of a variety of small carbon-containing groups, according to known synthetic methods. Some of the bridges in the partially oxidized structure will have the form =$CHN(R')CH_213$.

Figure 4A:
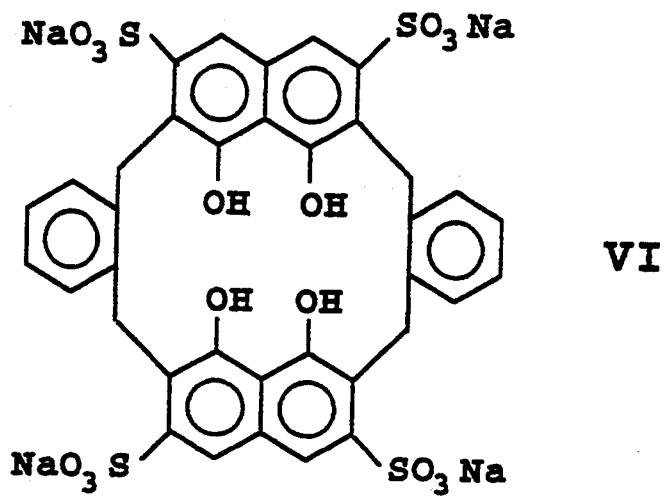
FIGS. 4A and 4B show an unoxidized (4A) and partially oxidized (4B) macrocycle with mixed phenyl and sulfonated naphthalene subunits.
Figure 4B:
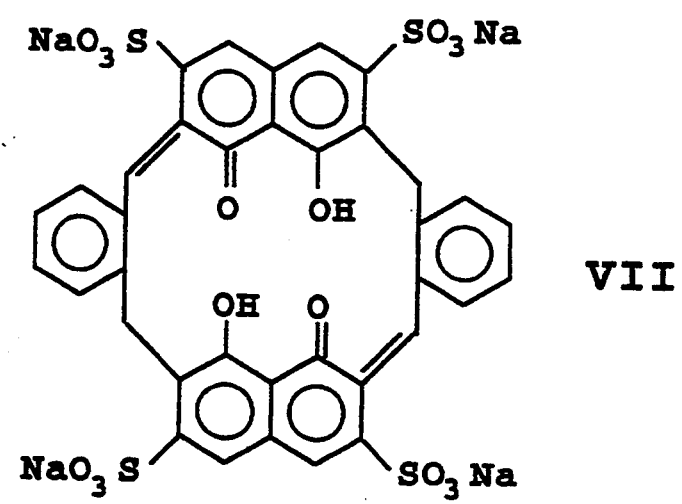

As noted above, the FIG. 4A compound (VI) is representative of macrocyclic naphthalene having a cyclic bridge, in this case a phenyl bridge. The compound is formed by reacting chromotropic acid, in the presence of hydrochloric acid with 1,2-benzenedimethanol in acetic acid, as detailed in Example 3. Similar methods can be employed to linked chromotropic acid subunits by other cyclic bridges, such as furan, pyrrole, thiophene, and the like. FIGS. 4A and 4B show the non-oxidized (VI) and partially oxidized (VIII) forms of the compound.

Figure 5:
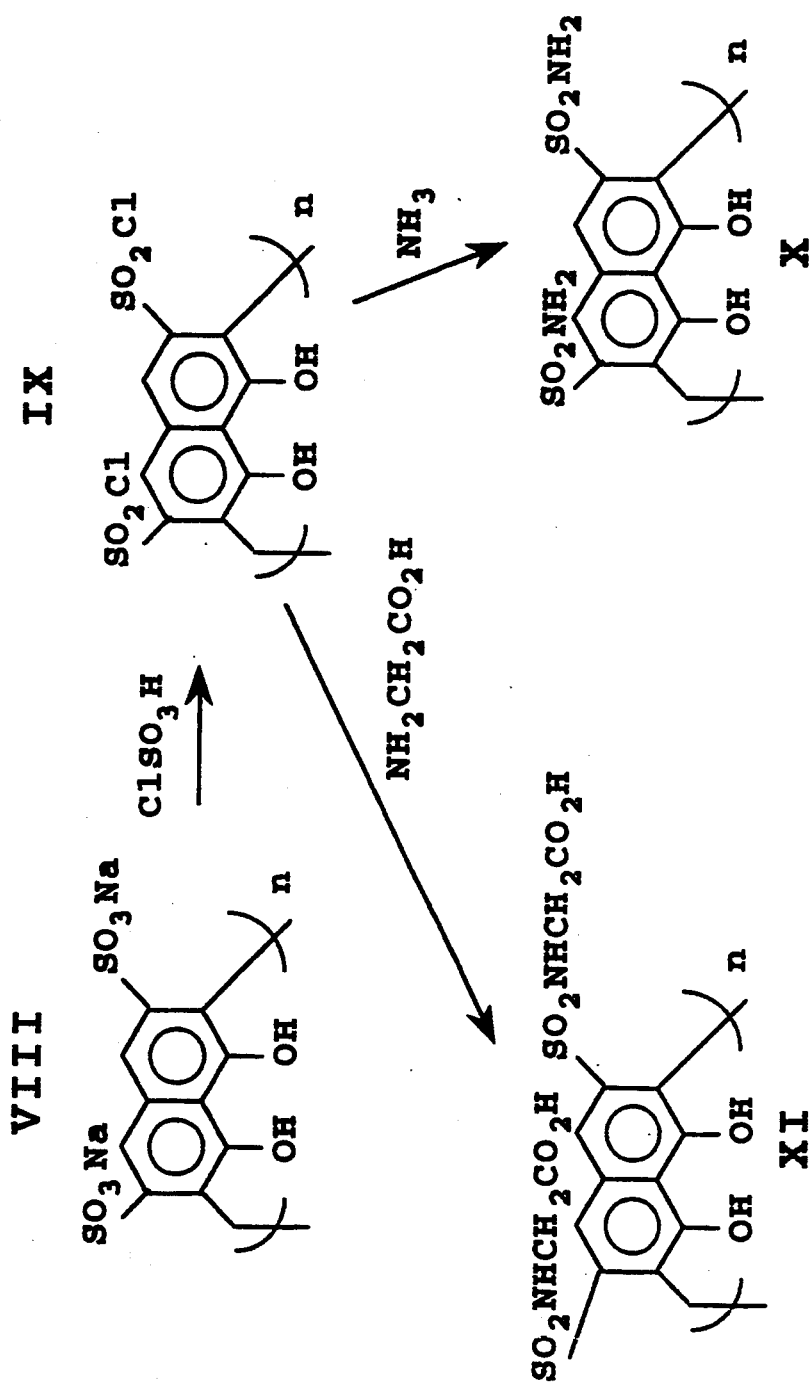
FIG. 5 illustrates reaction methods for converting the sulfonic acid substituents of macrocyclic chromotropic acid to glycyl sulfonamide and sulfonamide groups.

For synthesis of macrocyclic compounds with selected $R_1$, $R_2$, and $R_3$ substituents, two general approaches are available. In one approach, the chromotropic acid derivative is modified after cyclization so that the cyclized product will either contain the selected $R_1$, $R_2$, $R_3$ and $R_4$ substituent, or contain a substituent which can be readily modified to the selected substituent. This approach is illustrated by the synthesis of KY-3, which has an $SO_2NH_2$ $R_2$ substituent, as detailed in Example 1B. Here cyclized chromotropic acid (VIII) is reacted first with chlorosulfonic acid, to form the corresponding $R_2=SO_2Cl$ derivative (IX, FIG. 5). The macrocyclic compound is then reacted with ammonia water to form the desired $R_2=SO_2NH_2$ derivative (X, FIG. 5), as described in Example 1B.

A similar strategy was employed for the synthesis of KY-357 ($R_2=SO_2NHCH_2CO_2H$) by final subunit reaction with glycine (XI, FIG. 5), at basic pH.

Figure 6:
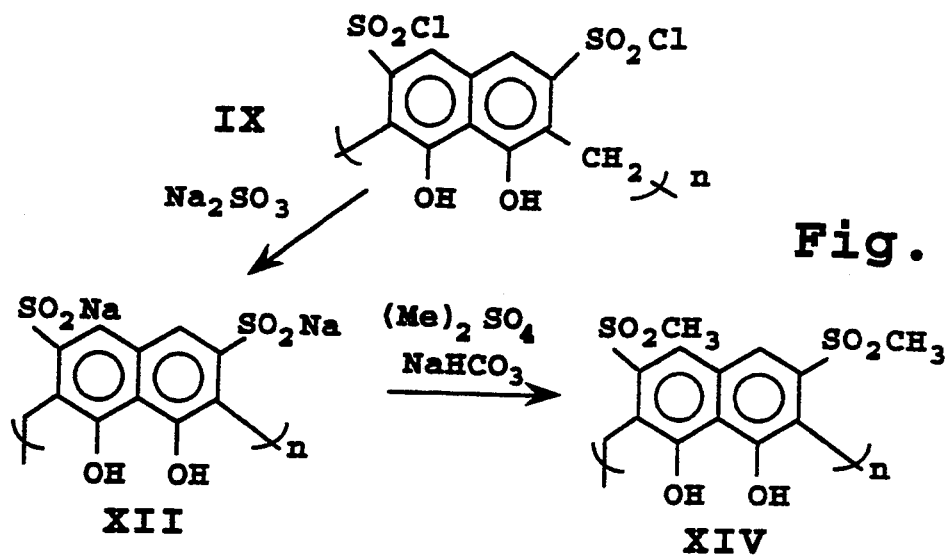
FIG. 6 illustrates a reaction method for converting the sulfonic acid (sodium salt) residues of macrocyclic chromotropic acid to sulfinic acid or its methyl (aryl) ester.

FIG. 6 illustrates the conversion of sulfonyl groups of cyclized chromotropic acid to sulfinate sodium salt (XII) and alkyl sulfinate ester (XIV). The first stage of the reaction involves the formation of the corresponding sulfonyl chloride derivative (IX), as outlined above. This compound is then treated with sodium sulfite, to form the corresponding a sulfinate salt (XII). Reaction with dimethyl sulfate in the presence of sodium bicarbonate produces the corresponding methyl sulfonate ester (XIV, KY-158, n=4).

Similarly, macrocyclic compounds with a variety of $R_1$ substituents may be prepared by modification of chromotropic acid after cyclization. In synthesizing KY-151, for example, ($R_1=OCH_3$) cyclized chromotropic acid is reacted with dimethylsulfate under basic conditions, as detailed in Example 1F, to form the methylether of cyclized chromotropic acid. Similarly, in preparing KY-307 ($R_1=O(CH_2)_5CO_2H$), cyclized chromotropic acid is first converted to the diether of hexanoic acid by initial reaction of cyclized chromotropic acid with 6-bromohexanoic acid under basic reaction conditions.

As further examples, in preparing compounds such as KY-272 and KY-294, in which $R_1$ has the form OCOR, the macrocyclic compound formed by cyclization of chromotropic acid is reacted with an acid chloride of the form RCOCl, under basic conditions, as detailed in Example 1I for the synthesis of KY-270.

In a second general approach, the selected substituent is formed on the subunit naphthalene rings by derivatization of the naphthalene subunit, with subsequent subunit cyclization to form the desired macrocycle. For the synthesis of KY-175 ($R_2=SO_3CH_3$), chromotropic acid is reacted with thionylchloride, as above, to produce the corresponding $R_1=SO_2Cl$ substituents. Further reaction with $NaOCH_3$ and cyclization leads to the desired $R_2$ substituent. Reaction details are given in Example 1H. Among other examples of this approach are KY-123 (Example 1G) and KY-147 (Example 1E).

It will be appreciated that the synthetic method for forming selected-substituent macrocyclic compounds may include both prior derivatization of chromotropic acid and subsequent derivatization of the subunits after cyclization. For example, in forming KY-397 ($R_1=OCH_3$, $R_2=SO_2NH_2$), chromotropic acid subunits are first reacted at the $R_1$ positions, to form the methyl ether derivative as described above. After cyclization with formaldehyde, the compound is further derivatized at the $R_2$ position, also as described above, to convert the $SO_3Na$ group to the desired $SO_2NH_2$ substituent.

The KY compounds described above can be converted readily to a variety of sulfonic acid or sulfonate salts, by reaction in acid or in the presence of a suitable salt, according to well known methods. Thus, for example, several of the KY compounds shown in Table 1 are ammonium salts formed by cation exchange of protons in the presence of an ammonium salt, such as ammonium chloride. In addition, exposure of the macrocyclic compound to a variety of metal cations, such as the cations of Ca, Ba, Pt, Cu, Bi, Ge, Zn, La, Nd, Ni, Hf, or Pb, may produce both a metal salt and a metal chelate of the macrocyclic compound in which the metal is chelated at an interior polar pocket in the compound.

The physical properties of several macrocyclic compounds prepared in accordance with the invention have been studied by absorption and mass spectrometry and by nuclear resonance spectroscopy (NMR), as detailed in Examples 1A, 1B, 1C, and 1J. These compounds include tetrameric macrocyclic compounds, such as indicated in FIG. 2, or mixtures with predominantly tetrameric forms.

B. Calix(n)arene Compounds

Figure 7:
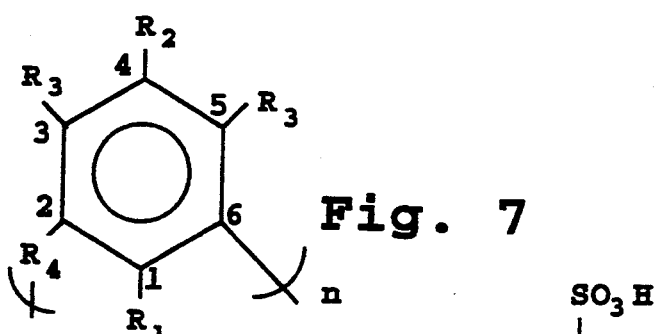
FIG. 7 shows the general structure of a macrocyclic compound composed of phenyl groups with para-position sulfonic acid-derived substitutents, for use in the present invention.
Figure 8:
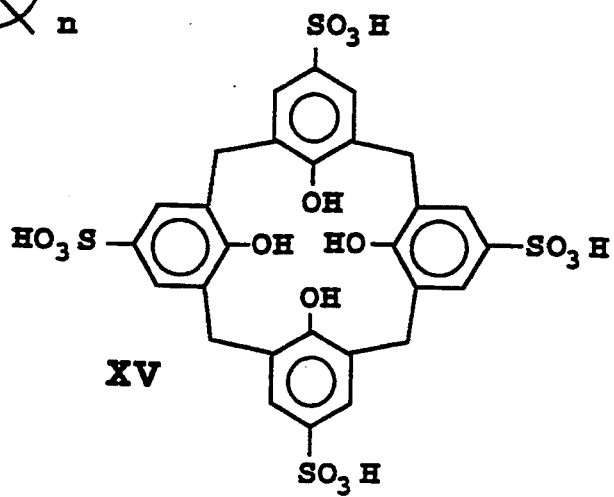
FIG. 8 shows a non-oxidized form of the FIG. 7 structure, where n=4 and the subunit is parasulfonic acid.

FIG. 7 shows the general structural formula of a calix(n)arene compound of the type used in the method of the present invention. One exemplary compound of this type is shown in FIG. 8, which is a tetramer of phenol parasulfonic acid subunits linked by methylene bridges (XV). As seen, the methylene bridges and the "interior" ring atoms (ring positions 2, 1, and 6) form a continuous chain having $R_I=OH$ groups attached at the 1 ring positions. The non-chain atoms (ring positions 3-5 on each substituent) have $R_2=$ sulfonic acid substituents on the 4 ring atoms.

Figure 9A:
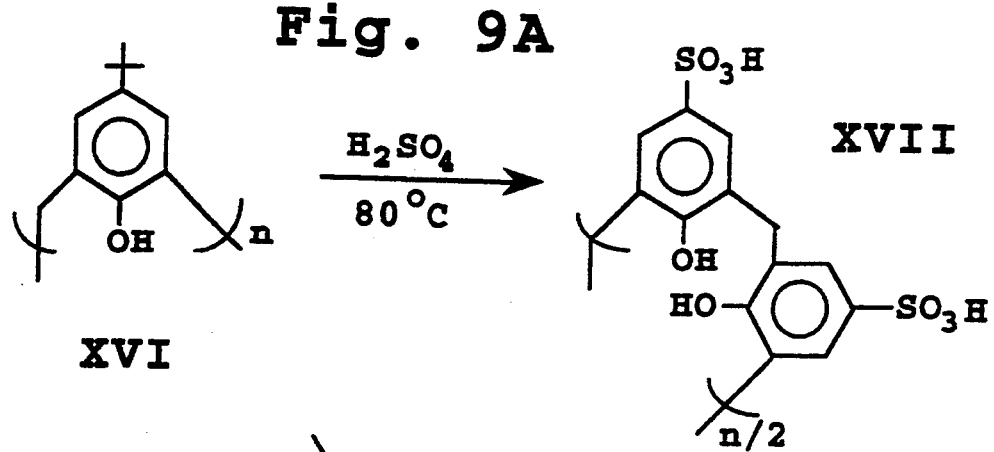
FIGS. 9A and 9B illustrate general methods of synthesis of non-oxidized and partially oxidized forms of the FIG. 8 compound.

FIG. 9A illustrates a general method for forming calix(n)arene compounds. The precursor shown at the left (XVI) is a tert-butyl calix(n)arenes, where n is the number of phenolic subunits (with para-position t-butyl substituents) in the macrocycle, and the bridge connections are methylene groups. t-butyl calixarenes with 4, 6, and 8, subunits are commercially available, and larger and uneven-numbered subunit calix(n)arenes can be prepared by standard purification methods.

In the sulfonation reaction shown in FIG. 9A, a t-butyl calixarene with a selected subunit number is treated with concentrated sulfuric acid, typically for about 4 to 5 hours at 75°–85° C. to effect substantially complete displacement of the 4-position t-butyl group by a sulfonic acid group. Details of the sulfonation reaction are given in Example 2A. The method has been used to produce the n=4 macrocycle compound shown in FIG. 8, and related macrocycles with 6 and 8 phenol subunits.

Figure 9B:
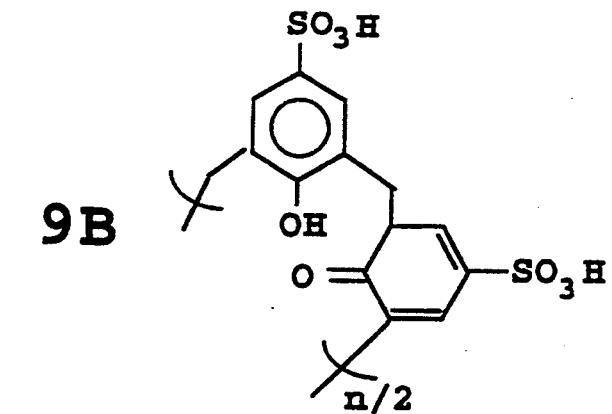

A similar method is used for preparing a sulfonated calixarene with partially oxidized 1-position OH groups, as shown at 9B. Here the t-butyl calixarene starting material is treated with conc. sulfuric acid at a temperature above 100° C., preferably between 150°–170° C. The reaction is effective to sulfonate the subunit rings and to partially oxidize the interior OH groups. As indicated in FIG. 9B, partial oxidation can lead to a conjugated calix(n)arene structure (XVIII) in which bridge contributes delocalized electrons. This conjugated structure is colored, and the development of a colored product can be used to monitor the course of the oxidation reaction. Details of the reaction are given in Example 2B.

Figure 10:
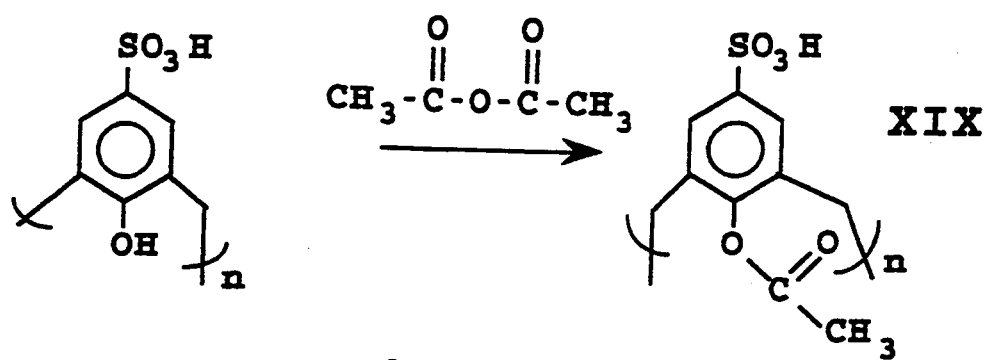
FIG. 10 shows a reaction scheme for replacing the ring hydroxyl groups in the FIG. 8 compound with acetyl groups.
Figure 11:
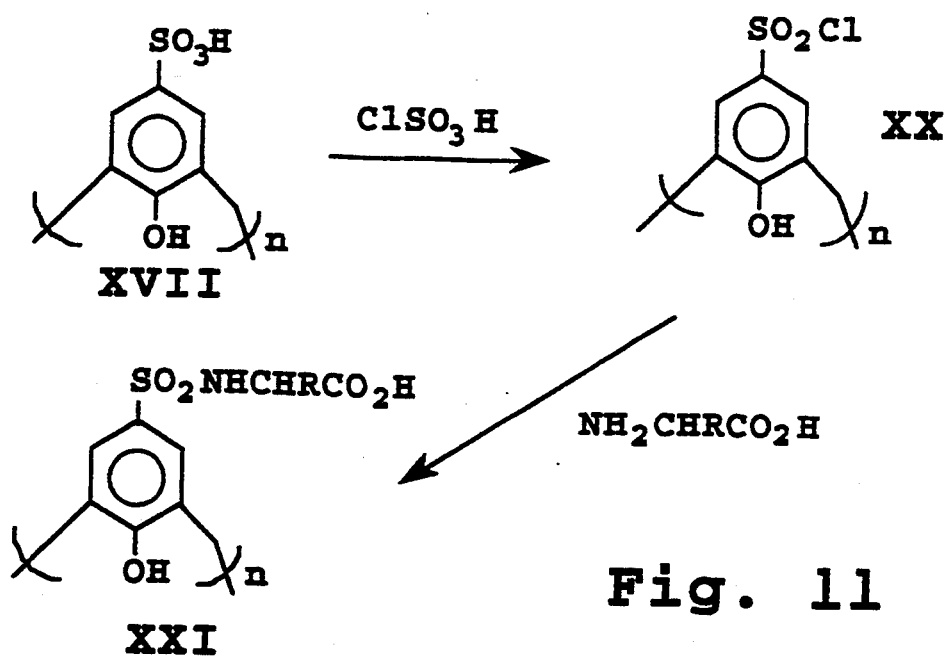
FIG. 11 shows a reaction for converting sulfonic acid substituents to a glycyl sulfonamide group in a phenyl-subunit macrocyclic compound.
Figure 12:
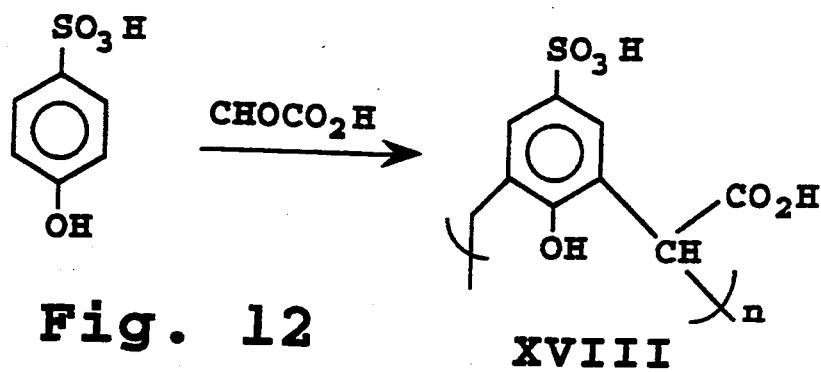
FIG. 12 shows a reaction scheme for producing a macrocyclic compound like that shown in FIG. 8 but with carboxylic acid-containing bridge linkages.
Figure 13:
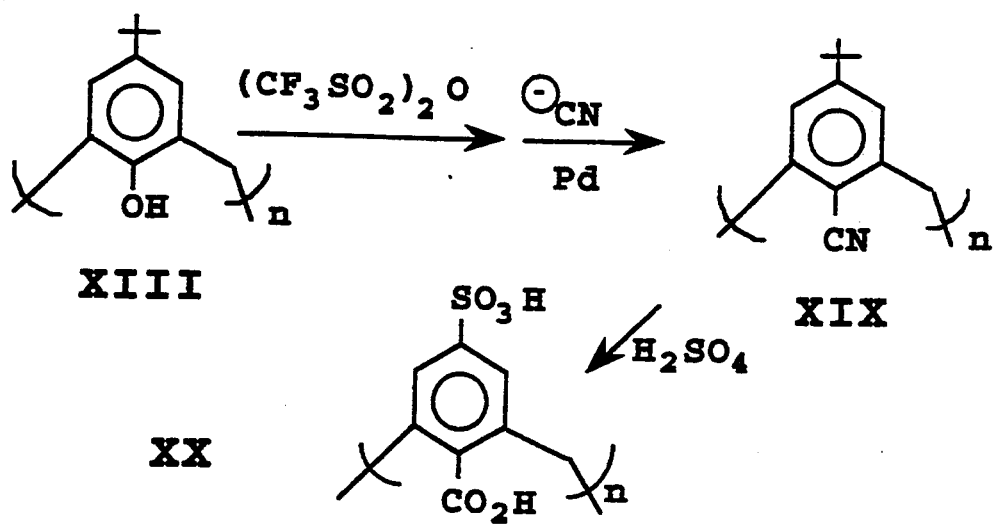
FIG. 13 shows a reaction scheme for replacing hydroxyl groups in the FIG. 8 compound with carboxylic acid groups.

It will be appreciated that the desired macrocycle can also be formed directly by reacting parasulfonic acid phenol (or precursors thereof) under suitable bridging conditions, such as described above for producing naphthalene-subunit macrocycles. This is illustrated by the reaction shown in FIG. 12, for production of a macrocycle having carboxylic acid-containing bridge groups. In this method, phenol parasulfonic acid is reacted with glyoxylic acid, under conditions similar to those described in Example 1C, to form the cyclized structure shown (XXII). The calix(n)arene compounds formed as above can be modified, according to general procedures outlined in Section IIA above, to achieve selected $R_1$ groups, modified sulfonyl groups, and/or addition of $R_2$ groups. The range of $R_1$ and $R_2$ substituents is substantially the same as that discussed above. FIG. 10, 11 and 13 illustrate various reaction methods for modifying the $R_1$ group of an already formed macrocycle. In FIG. 10, the sulfonated structure shown in FIG. 8 is treated with acetic anhydride, to form an O-acetyl $R_1$ group. Details of the reaction are given in Example 2C. Since this structure would be expected to undergo hydrolysis in the presence of serum esterases, differences in the activity of the ester compound and the free OH compound would be expected to occur after intravenous (IV) administration. Example 2G describes a similar reaction scheme for forming a toluene sulfonic acid ester at the $R_1$ position.

FIG. 11 illustrates a general method for forming sulfonamides, such as glycylsulfonamide (XXI) of the FIG. 8 compound. Analogous to the reactions described with respect to FIG. 5, the sulfonated phenyl calix(n)arene compound (XVII) is treated with chlorosulfonic acid, to form the corresponding sulfonyl chloride analog (XX). Further reaction with a selected amine, in this case glycine, gives the desired sulfonamide. Reaction details are given in Example 2D for the synthesis of the $R_2=SO_2NH_2$ compound and in Example 2E, for the synthesis of the glycyl sulfonamide compound.

FIG. 13 depicts a general non-exclusive synthetic method for a net substitution of $R_1=OH$ by $R_1=$carbon moieties. In Example 2H, the reactions detail a process from which a substrate ($R_1=OH$, $R_2=$tert-butyl, $R_4=CH_2$, n=4) affords an intermediate ($R_1=CN$, $R_2=$tert-butyl, $R_4=CH_2$, n=4). Further modification then provides the product ($R_1=CO_2H$, $R_2=SO_3H$, $R_4=CH_2$, n=4).

It will be appreciated that substituent modifications at the $R_1$ site can be selectively carried out at OH sites in the partially oxidized macrocycle, such as the structure shown at FIG. 9B. That is, reactions which are specific for ring OH groups will leave the =O group intact, thus providing a mixed $R_1$ group containing =O groups.

The $R_3$ is generally H, but may be an uncharged or negatively charged substituent, similar to the $R_3$ group described in Section IIA above.

The $R_4$ bridge linking the chromotropic acid derivative subunits is preferably of the form >CHR or ≧CR, where R is H or a small carbon-containing group, such as lower alkyl, alkenyl, ketone, or carboxylic acid group, or aryl group, as noted above, or of the form —$CH_2NR'CH_2$—, where R' is similarly H or a small carbon containing group, such as a lower alkyl group. Alternatively, the bridges in the macrocycle may be ring structures, including aryl ring structures, analogous to the dimeric macrocycle shown in FIG. 4.

Also as above, the number of subunits may vary from 4 (e.g., FIG. 4 structure) to 8 with macrocycles containing 4, 6 and 8 subunits being preferred. In the reaction schemes described below, the macrocycle formed may include mixtures of compounds with different subunit numbers (n) values, e.g., a dominant n=4 structure (4 subunits) plus additional structures containing 5–8 subunits.

Representative calix(n)arene compounds which have been synthesized and tested for activity are identified by their $R_1$, $R_2$, and $R_4$ substituents in Table 2 below. The KY and Y number in the lefthand column in the table refers to the analog designation of the corresponding compound, as in Table 1. Compounds which are partially oxidized at the $R_1$ position, and have which may have both saturated and unsaturated bridge methylene carbon groups are indicated as in Table 1.

TABLE 2

| Compound | $R_1$ | $R_3$ | $R_4$ | n |
|---|---|---|---|---|
| Y-1 | OH | $SO_3$ | —$CH_2$— | 8 |
| KY-226 | O/OH | $SO_3$ | —$CH_2$/=CH— | 8 |
| Y-49 | OH | $SO_3$ | —$CH_2$— | 4 |
| KY-225 | O/OH | $SO_3$ | —$CH_2$/=CH— | 4 |
| Y-77 | OH | $SO_3$ | —$CH_2$ | 6 |
| Y-48 | O/OH | $SO_3$ | —$CH_2$/=CH— | 6 |
| KY-268 | O/OH | $SO_3$ | —$CH_2$/=CH— | 3 |
| KY-269 | O/$CO_2CH_3$ | $SO_3$ | —$CH_2$/=CH— | 4 |
| KY-271 | O/$CO_2CH_3$ | $SO_3$ | —$CH_2$/=CH— | 3 |
| Y-78 | O/OH | $SO_2NH_2$ | —$CH_2$— | 8 |
| Y-100 | O/OH | $SO_2OCH_3$ | —$CH_2$— | 8 |

The compounds shown in Table 2, and R-group combinations thereof, described above can be converted readily to a variety of sulfonic acid or sulfonate salts, by reaction in acid or in the presence of a suitable salt, according to well known methods, as described above.

C. Calix(n)arene Compounds with Sulfonate, Phosphonate, and Carboxylate Groups

One general class of calix(n)arene compounds which are useful in anti-thrombus therapy, in accordance with the present invention, are calix(n)arene compounds in which the ring position meta to the bridge attachments, i.e., 4-position carrying substituent $R_2$ in FIG. 7, is substituted with a polar substituent having a terminal sulfonic acid, phosphonic acid or carboxylic acid group. Included are polar substituents which terminate in a sulfonic acid ester or amide, a phosphonic acid ester or amide, or a carboxylic acid ester or amide, as defined above, where the ester and amide groups are cleavable, in vivo to form the corresponding acid group.

Methods for preparing calix(n)arene compounds in which a sulfonic acid is carried at the ring 4 position are given in Examples 2A, 2B, and 2C, including compounds with different substitutions at the ring 1 position. Compounds having sulfonamide group, including a group which terminates with an end terminal carboxyl group are given in Examples 2D and 2E, respectively.

Figure 15:
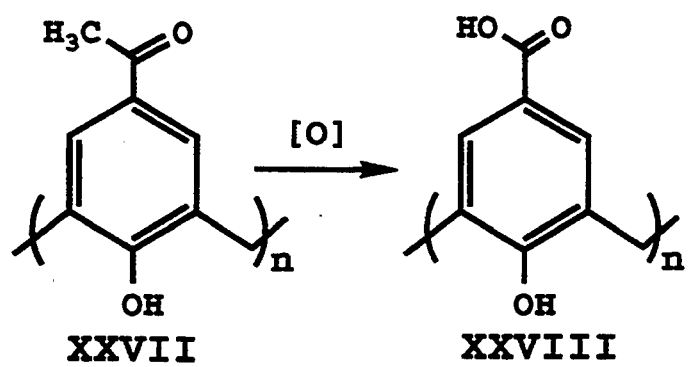
FIG. 15 shows a reaction scheme for preparing a calixarene having para-carboxyl substituents.

FIG. 15 shows the conversion of a calix(n)arene (XXVII) carrying a p-acetyl group to the corresponding calix(n)arene with a p-carboxyl group (XXVIII). Details are given in Example 2K.

Figure 14:
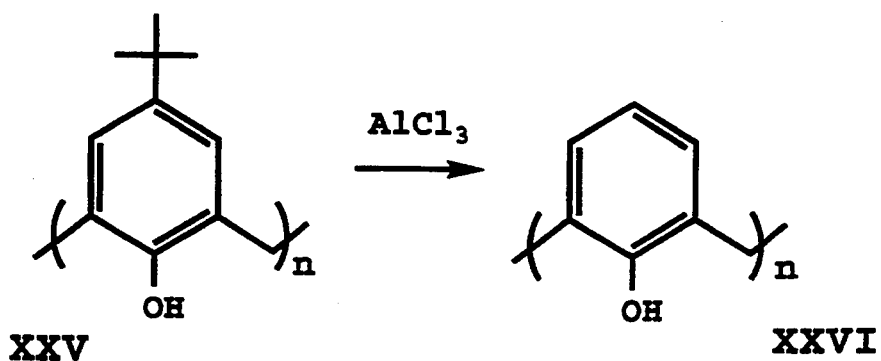
FIG. 14 shows a reaction scheme for producing calix-(n)arene from a para-tert-butyl-precursor.

FIG. 14 illustrates a method for converting a t-butyl calix(n)arene (XXV) to the unsubstituted compound (XXVI), which can be used as a starting material for some of the syntheses described below. Details of the reaction are given in Example 2J.

Figure 16:
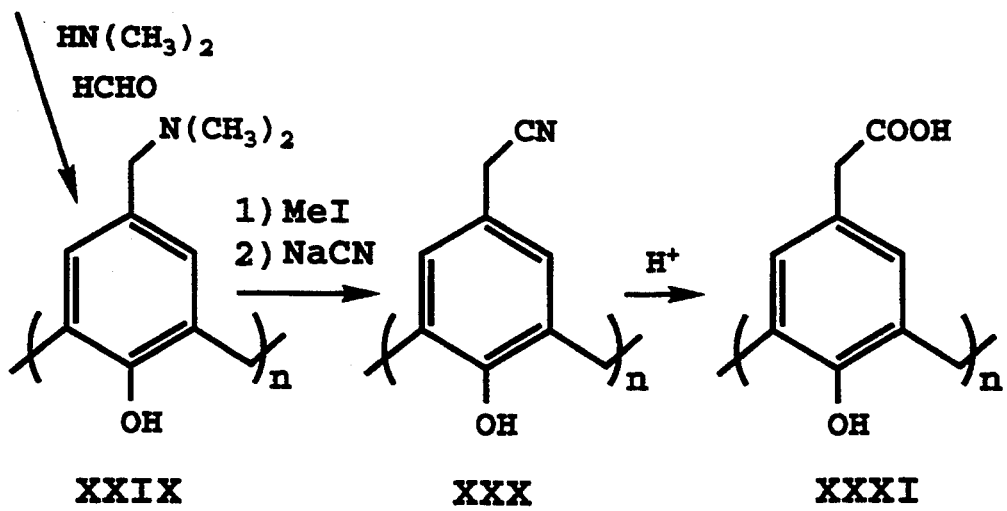
FIG. 16 shows a reaction scheme for preparing a calixarene having carboxyl substituents linked to the para position by a methylene linker.
Figure 17:
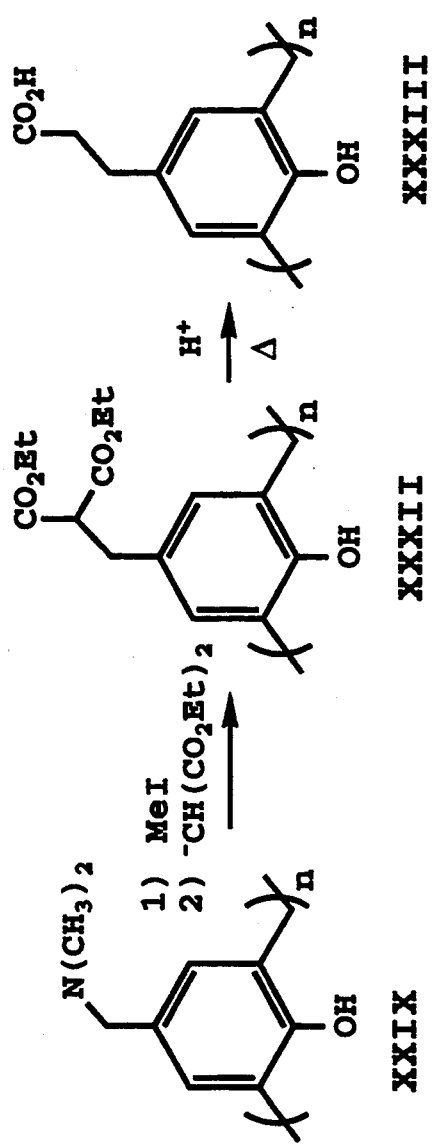
FIG. 17 shows a reaction scheme for preparing a calixarene like that of FIG. 16 but where the carboxyl substituents are linked to the para position by an ethylene linker.

To form the p-carboxyethyl compound shown at XXXI in FIG. 16, compound XXVIII produced above is converted to the corresponding (dimethylaminio)-methyl compound (XXIX) by reaction with dimethyl amine and formaldehyde. This compound is then taken to the corresponding cyanomethyl compound (XXX), which when heated in acid, is converted to the desired carboxymethyl compound (XXXI). Details are given in Example 2L FIG. 17 illustrates the synthesis of a carboxyethyl calix(n)arene (XXXIII). Here the intermediate (XXIX) from above (FIG. 16) is treated sequentially with MeI and the odium salt of diethylmalonate to give the diethylmalonylmethyl compound (XXXII). Heating in acid gives the desired compound XXXIII. Details are given in Example 2M.

Figure 18:
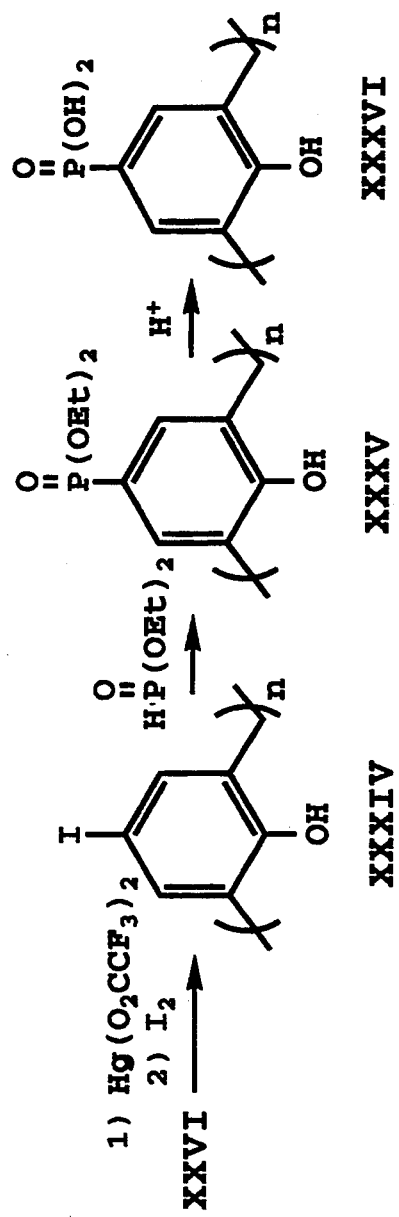
FIG. 18 shows a reaction scheme for preparing a calixarene having para-phosphonate substituents.

FIG. 18 illustrates the synthesis of a p-phosphonate calix(n)arene (XXXVI). In this synthesis, compound XXVI from above is iodinated and then reacted with diethylphosphite to give the diethylphosphonate compound (XXXV). Refluxing in acid gives the desired compound XXXVI. Details are given in Example 2N.

Figure 19:
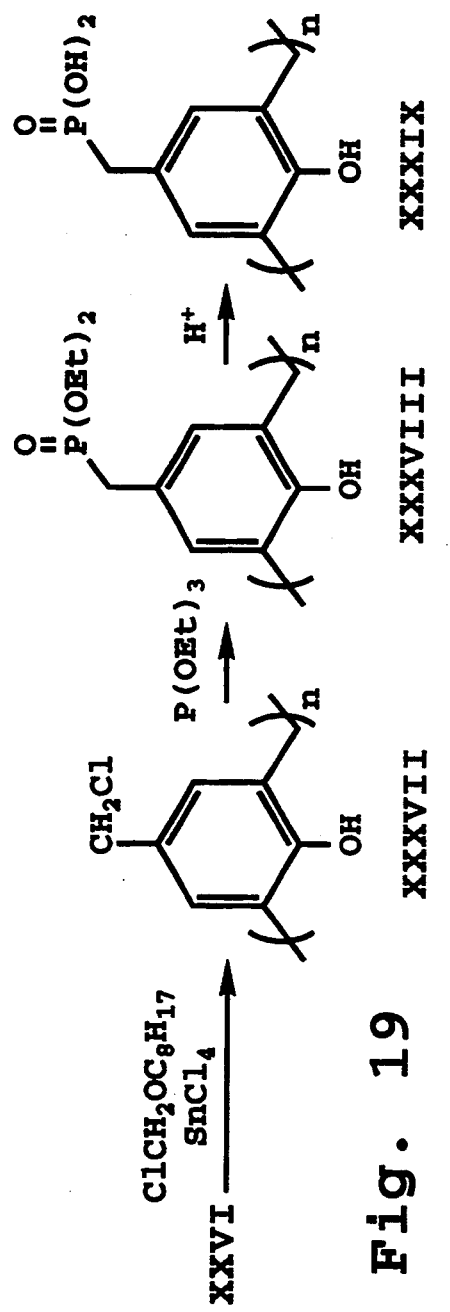
FIG. 19 shows a reaction scheme for preparing a calixarene having phosphonate substituents linked to the para position by a methylene linker.

The synthesis of a calix(n)arene phosphonomethyl compound (XXXIX) is shown in FIG. 19. As seen, compound XXVI from above is chloromethylated (compound XXXVII), and further reaction with triethylphosphite gives a diethylphosphonyl ester compound (XXXVIII). Heating in acid gives the desired phosphonomethyl compound. Details are given in Example 2O. Note that the chloromethyl intermediate is also useful in synthesis of the sulfonomethyl calix(n)arene analog.

Figure 20:
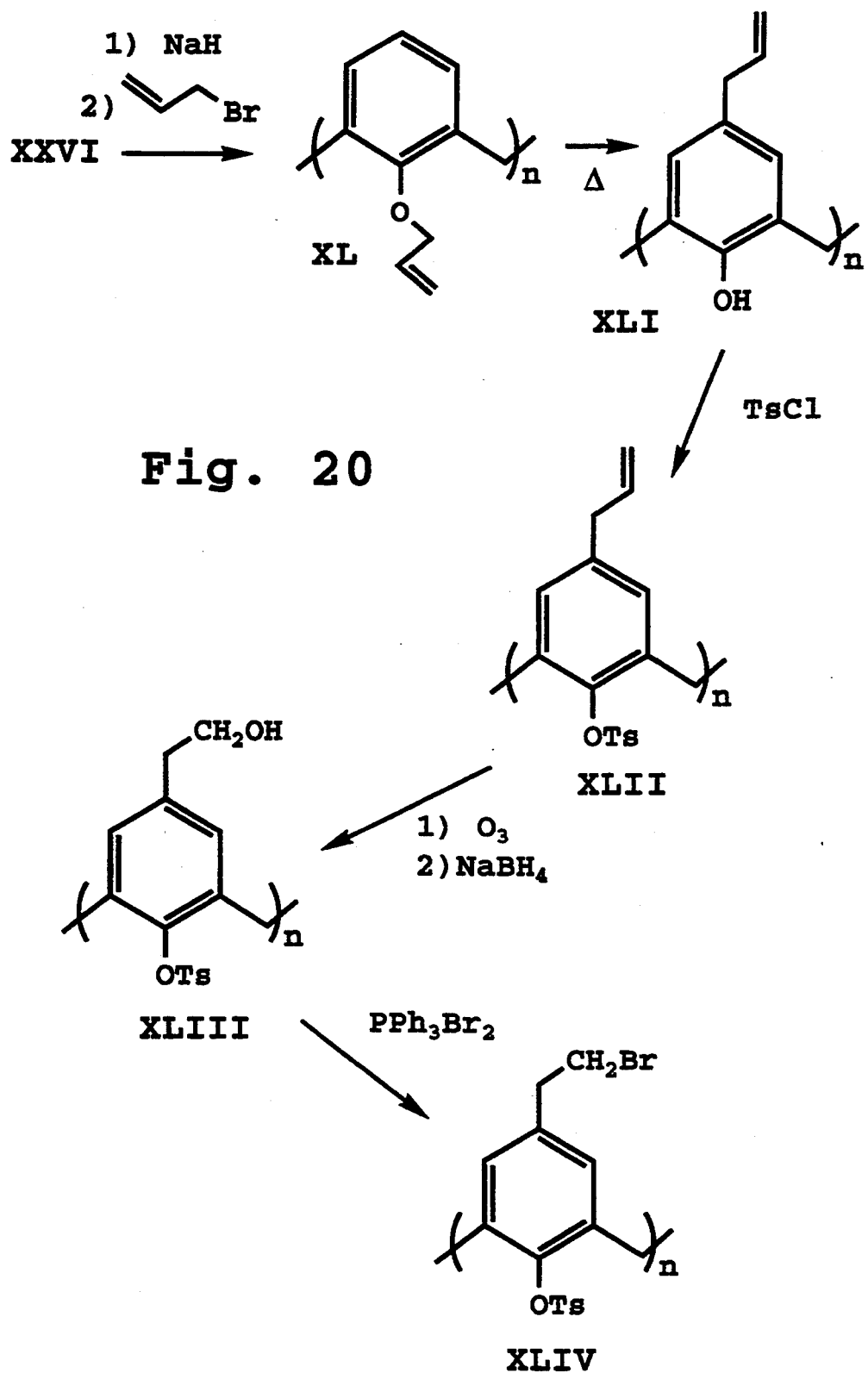
FIG. 20 shows a reaction scheme for preparing a p-2-bromoethyl-O-tosyl-calixarene as a precursor for preparing other calixarene derivatives.
Figure 22:
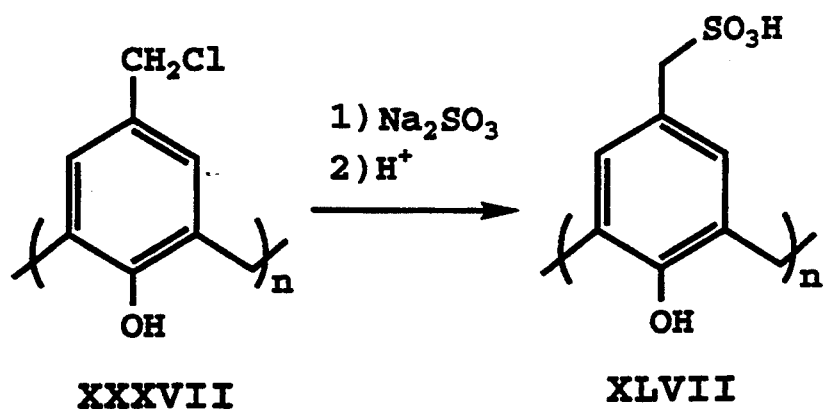
FIG. 22 shows a reaction scheme for preparing a calixarene derivative like that of FIG. 19, but with a sulfonate group instead of a phosphonate group.

The synthesis of a p-2-bromoethyl compound useful in the synthesis of a phosphonoethyl or sulfonoethyl calix(n)arene is outlined in FIG. 20, with details given in Example 2P. With reference to the figure, compound XXVI from above is alkylated at the phenol hydroxyl (compound XL), and heated to give the rearrangement product XLI. Tosylation serves to protect the phenyl hydroxyl position (compound XLII), allowing conversion to the p-hydroxyethyl derivative (XLIII). Further reaction with triphenylphosphine dibromide gives the desired p-bromoethyl XLIV compound.

Figure 21:
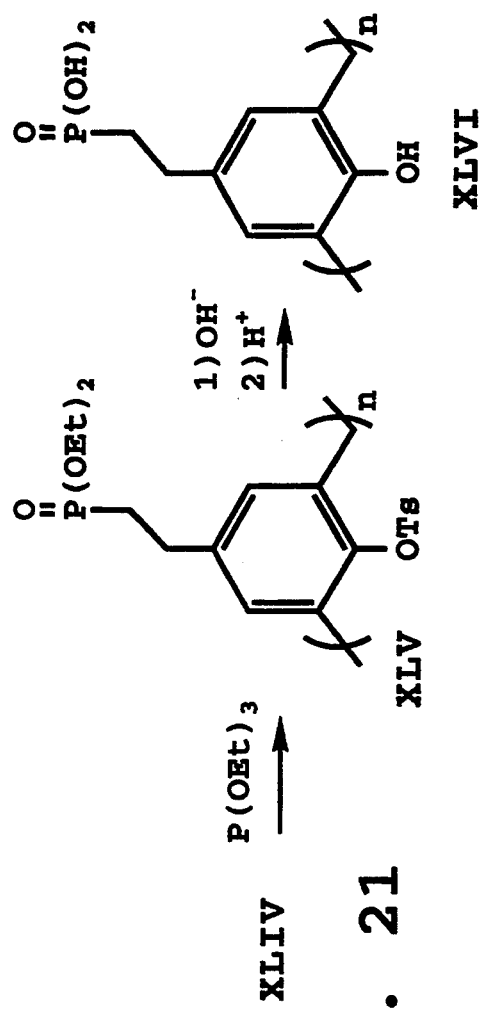
FIG. 21 shows a reaction scheme for using the bromoethyl-calixarene of FIG. 20 to prepare a calixarene like that of FIG. 19, but where the phosphonate substituents are linked to the para position by an ethylene linker.

The p-bromoethyl calix(n)arene (XLIV) is used in the synthesis of the p-phosphonoethyl compound (XLVI), by a reaction sequence which is analogous to that shown in FIG. 19. described above. Details of the reaction scheme shown in FIG. 21 are given in Example 2Q.

The intermediate p-chloromethyl calix(n)arene (compound XXXVIII) used above can also be used in the synthesis of a p-sulfonomethyl calix(n)arene (XLVII), as shown in FIG. 2, with details provided in Example 2R.

Figure 23:
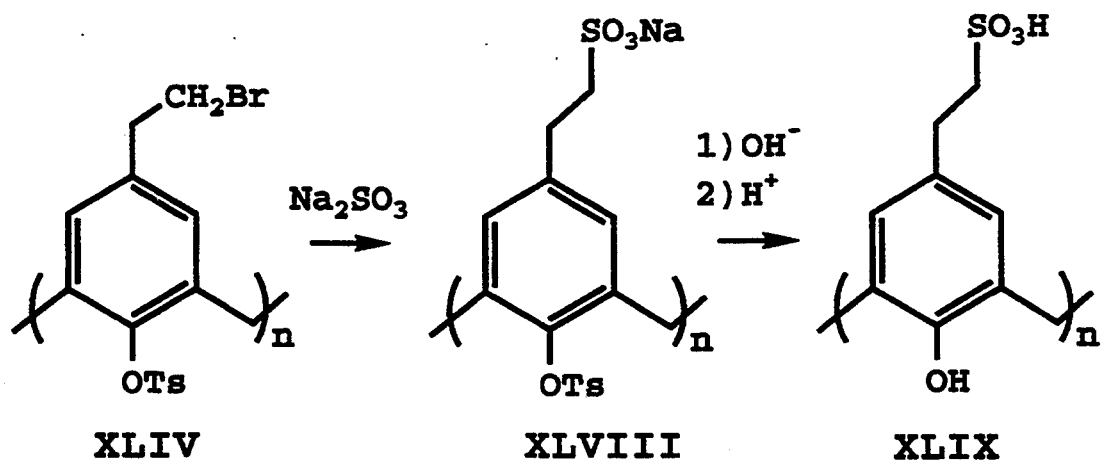
FIG. 23 shows a reaction scheme for preparing a calixarene derivative like that of FIG. 21, but with a sulfonate group instead of a phosphonate group.

Similarly, the p-2-bromoethyl intermediate (XLIV) described above can be used in the synthesis of the p-sulfonoethyl calix(n)arene (XLIX) as shown in FIG. 23, with details given in Example 2S.

The foregoing synthetic methods can be used to produce calix(n)arene compound having at the position meta to the bridge positions (the C4 ring positions), polar substituents which terminate with sulfonic acid, phosphonic acid, and carboxylic acid. The syntheses outlined show both direct acid-group attachment to the rings, or attachment through alkyl linkages, such as methyl and ethyl linkages. It will be appreciated from the discussion below, how acid groups linked to the rings through longer alkyl groups can be prepared. Also, as detailed above, the acid groups can be converted to the corresponding salts.

It will also be appreciated how a variety of esters and amides of the terminal acid groups in the calix(n)arene compounds can be prepared. Generally, the acid esters of carboxylic acid and sulfonic acid can be prepared by standard esterification reactions in which the acid is converted to, for example, an acid chloride, then reacted with an alcohol, such as an alkyl alcohol. The amides of carboxylic and sulfonic acid can similarly be formed by reaction of the acid chloride with an amine, such as an alkyl amine. Preferred esters include aryl and lower alkyl carbonate esters, such as n-butyl alkyl group. Preferred amides include amides of lower alkyl groups.

The conversion of a phosphonic acid calix(n)arene to a corresponding ester or amide likewise follows conventional phosphate esterification or amidation reaction methods. One method for generating the diethyl phosphonyl ester has been described above with reference to FIG. 21.

In addition to the polar substituents at the C4 position in the calix(n)arene rings, the present invention contemplates, for use in anti-thrombus treatment, calix(n)arene compounds which are substituted at other ring positions and at the bridge positions in the macrocycle. For example, the C3 and/or C5 ring positions may be substituted with halogens such as F of Cl. Also as described above with respect to several of the naphthyl-ring macrocycles, substitutions at the "inner" ring positions (the C1 ring positions in calix(n)arene) are compatible with anti-thrombus activity. Also as described above, substitutions at the bridge positions in naphthyl-ring macrocycles is compatible with activity.

Figure 24:
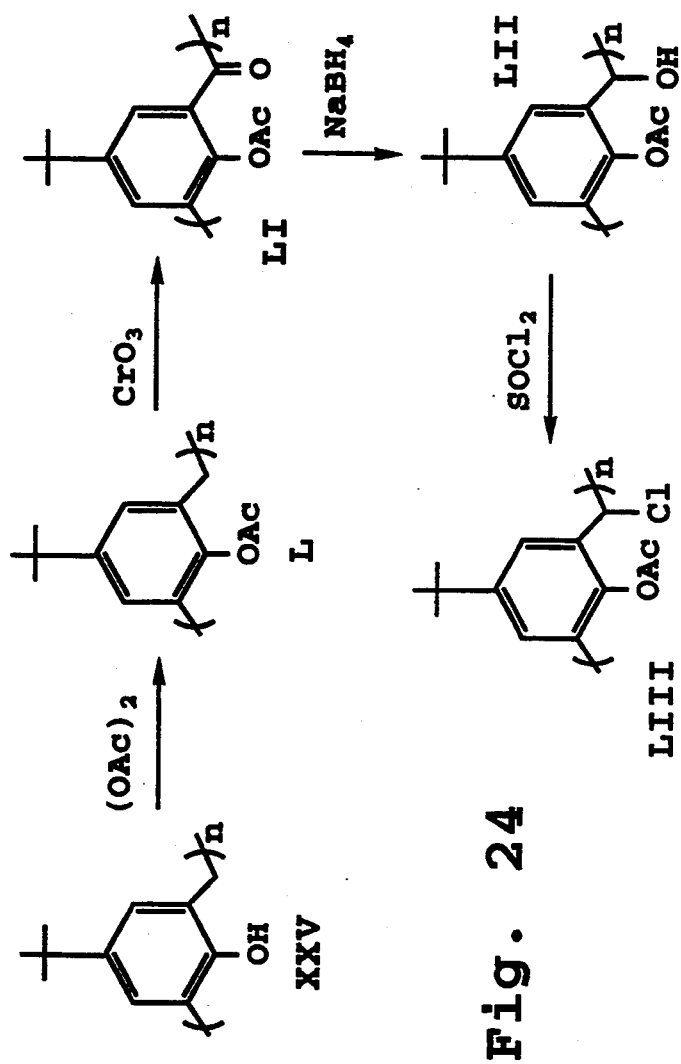
FIG. 24 shows a reaction scheme for preparing a calixarene having a chlorine atom at the methylene bridge for further introduction of other substituents at the methylene bridge.
Figure 25:
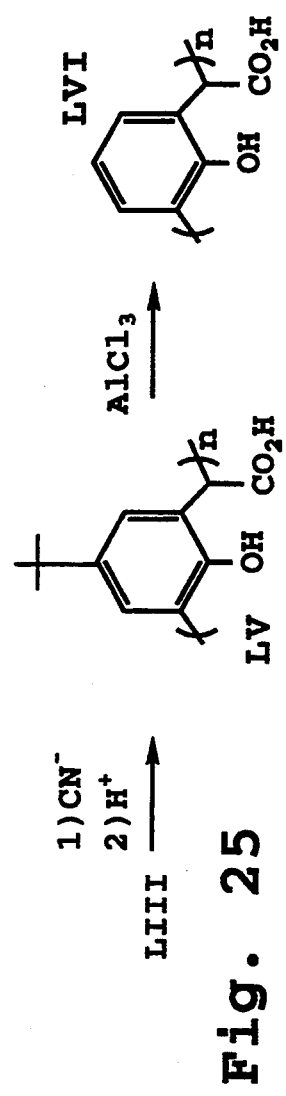
FIG. 25 shows a reaction scheme for preparing calixarenes like that of FIG. 12, but starting from the cyclized precursor from FIG. 24.

FIGS. 24 and 25 illustrate one method of attaching carboxyl groups to the bridge methylene in calix(n)arene. In this method, the hydroxyl group of p-t-butyl calix(n)arene (XXV) is acetylated (L), and the product is oxidized at the bridge methylene, to give the bridge ketone (LI). Reduction with sodium borohydride, and subsequent reaction with thionyl chloride yield the compound LIII which is chlorinated at the methylene bridge. Details are given in Examples 2T and 2U.

With reference to FIG. 25, the compound LIII is cyanylated, then treated with acid to form the carboxylic acid group at the bridge methylene. The resulting compound LV can be de t-butylated by treatment with aluminum chloride to give the bridge-carboxylated calix(n)arene shown at LVI. Alternatively, compound LV may be sulfonated, at the C4 ring position, by treatment with sulfuric acid, as above. It will be appreciated that similar methods, but involving initial protection of the bridge carboxyl and ring hydroxyl groups, can be used to form corresponding p-phosphonic acid or p-carboxylic acid calix(n)arenes.

Figure 26:
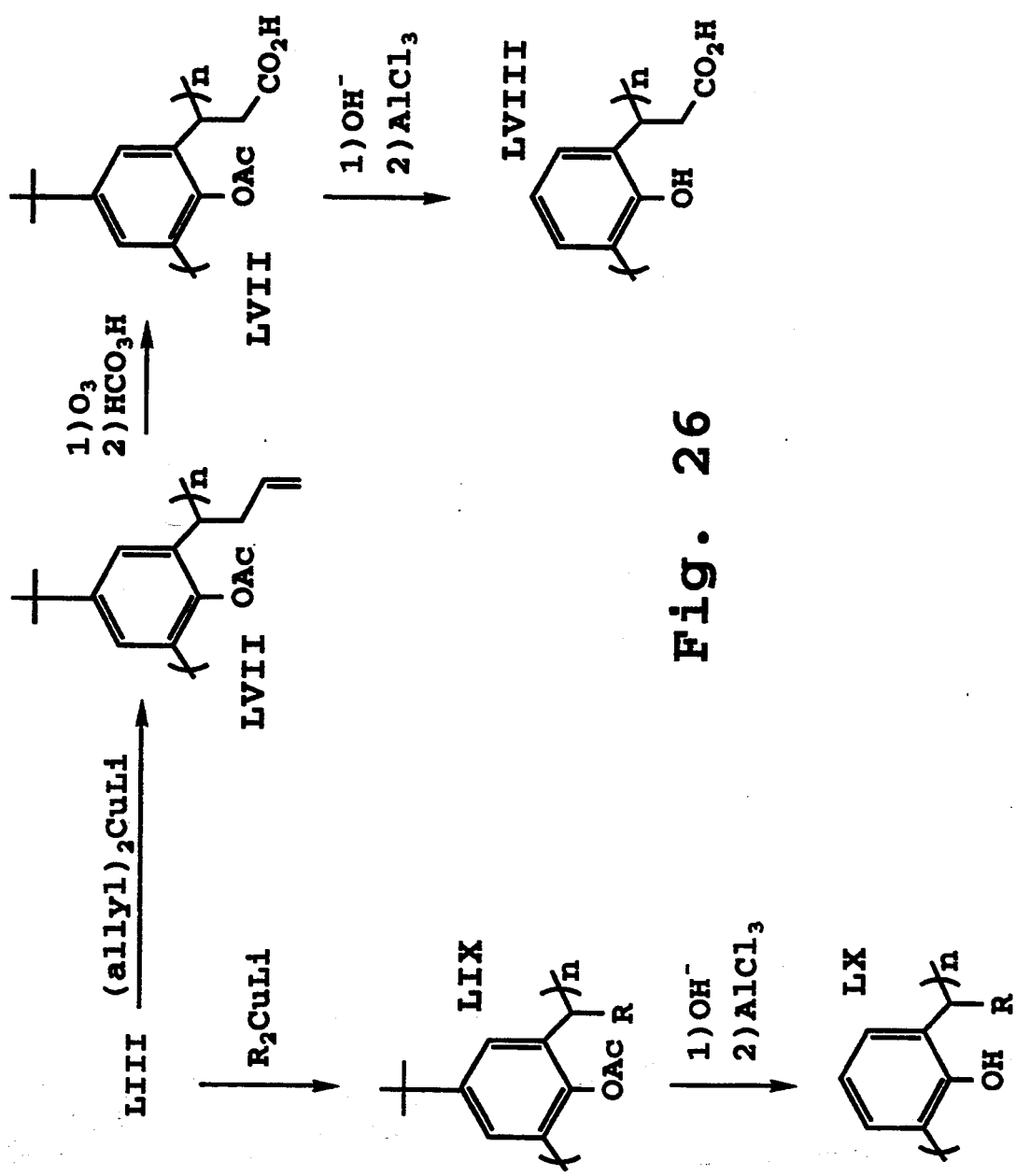
FIG. 26 shows a reaction scheme for preparing a calixarene having a carboxymethyl group attached to the bridging methylene, as well as a general approach for preparing a variety of calixarenes having selected R groups at the methylene bridge, using organocuprate reagents.

Using compound LIII from above, a variety of bridge substitutions can be produced, by the method outlined in FIG. 26, using a suitable cuprate reagent as illustrated at the left in the figure. The reaction at the right in the figure shows how a calix(n)arene LIII can be converted to a compound having a carboxymethyl attached to the bridge methylene group. Details of this reaction sequence are given in Examples 2W and 2X. The final reaction product (LVIII) can be p-sulfonated or derivatized with other acid groups at the para position as above.

Figure 27:
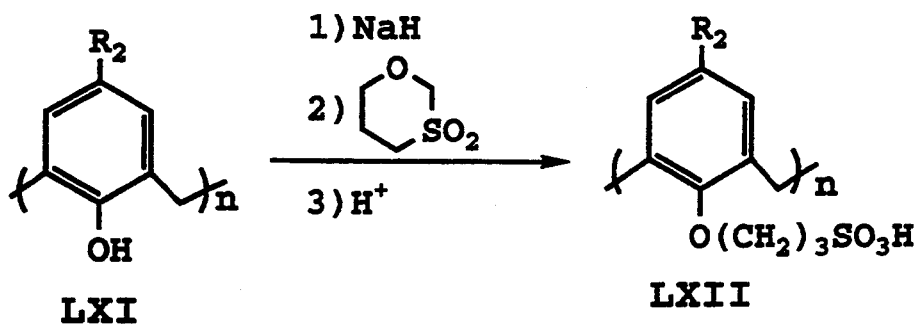
FIG. 27 shows reaction schemes for preparing a number of calixarenes having 3-sulfonlypropyloxy groups attached to the calixarene rings.
Figure 27:
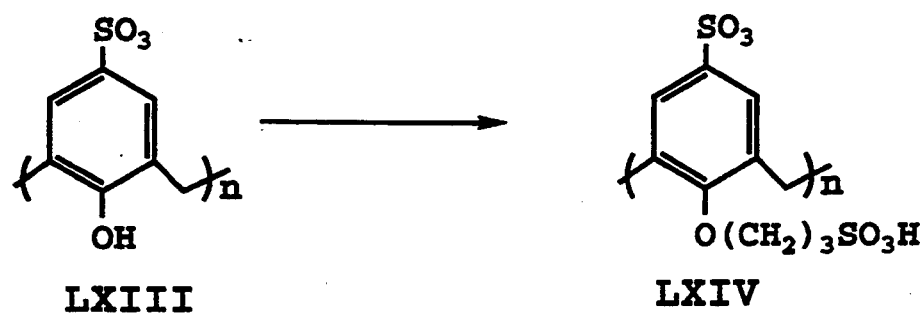
Figure 27:
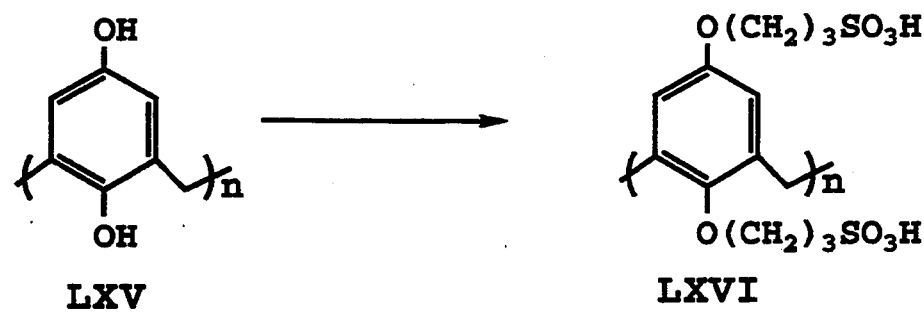
Figure 27:
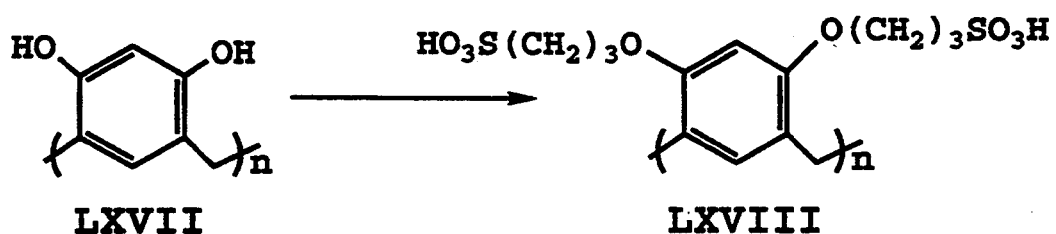
Figure 27:
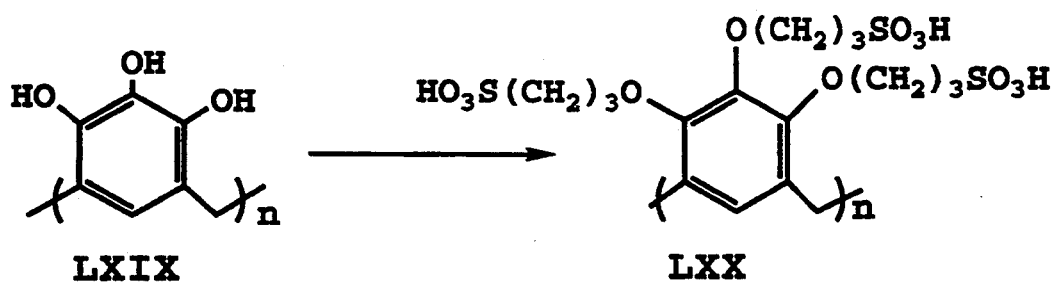

FIG. 27 shows a variety of derivatization reactions involving calix(n)arenes and propane-1,3-sulfone. The reactions are effective to add alkylsulfonate groups at ring hydroxyl positions, as shown. This method provides an alternative approach for producing a calix(n)arenes with ring-attached sulfonic acid groups. Reaction details are given in Examples 2Y and 2Z.

Figure 28:
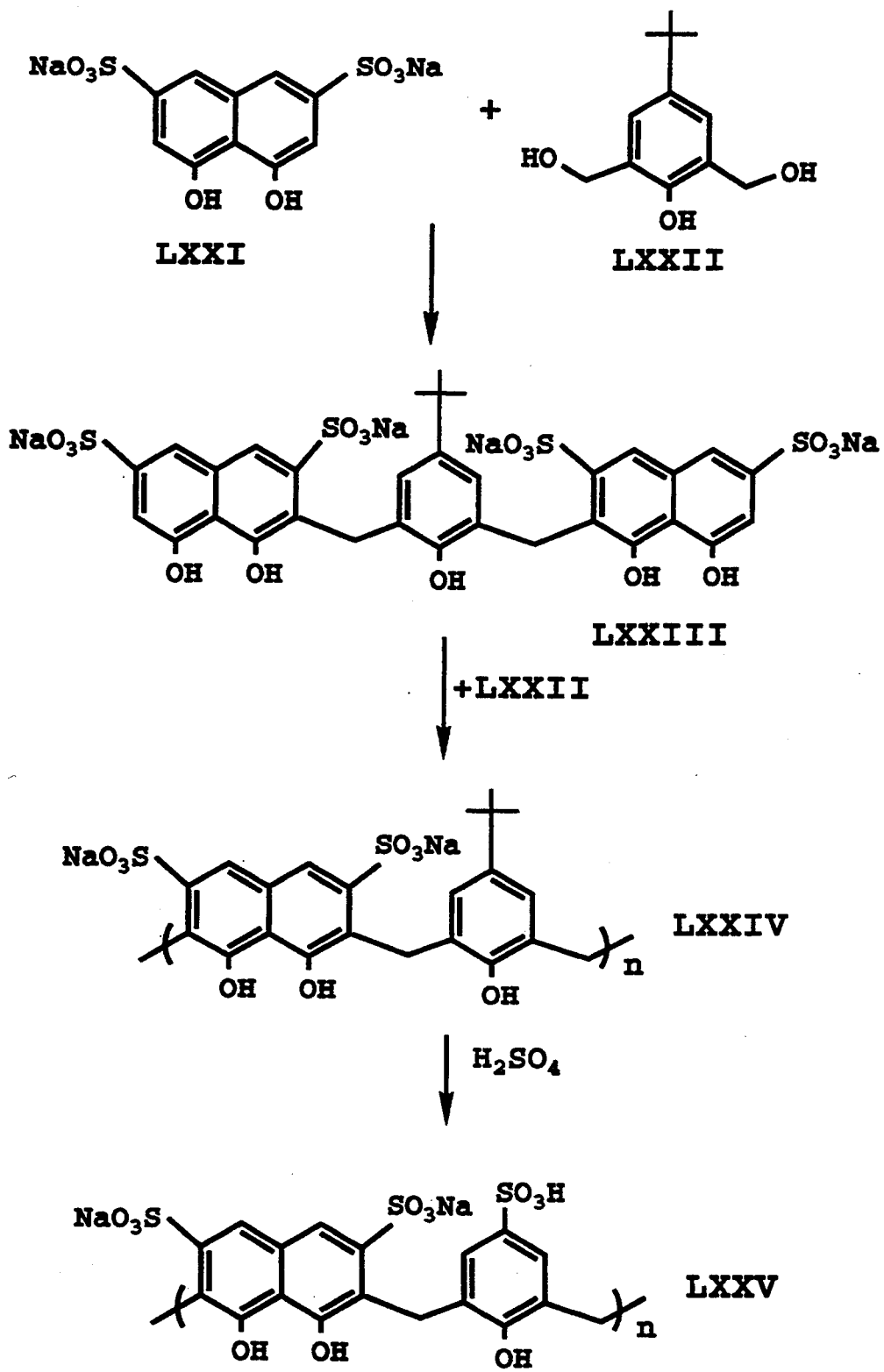
FIG. 28 shows a reaction scheme for preparing a macrocyclic compound having alternating phenyl and napthyl rings.

Finally, FIG. 28 shows the preparation of a mixed macrocycle containing alternating phenyl and naphthyl groups. The reaction method is described in Example 3B.

III. Antithrombotic properties of macrocyclic compounds

This section describes the ability of compounds useful in the invention to inhibit coagulation of blood, as shown in one or more standard blood coagulation assays, and, by such inhibition of coagulation, to prevent thrombus formation in vivo. As described in the section entitled Background of the Invention, anti-thrombotic activity is exhibited by drugs having anti-coagulant as well as those having anti-platelet activities. That is, by interfering with natural hemostatic mechanisms, both types of drugs are effective in preventing thrombus formation.

Assays which are used in assessing anticoagulant activity and, to some degree, mechanism of anticoagulant activity, include, but are not limited to, the activated partial thromboplastin time (APTT) assay, the prothrombin time (PT) assay, the thrombin time (TT) assay, the fibrinogen assay, the reptilase (atroxin time, AT) assay, and the plasma clotting (recalcification) time assay. Such assays and specific methods for carrying them out are known generally in the art and are described by Brown (1988).

The blood used to test compounds in such assays may be from a variety of vertebrate sources, although mammalian, and particularly human sources are preferred. In carrying out such assays, venous blood samples are obtained using clean venipuncture procedures, in order to prevent contamination of the sample by exogenous cells. Blood samples employed in the screening compounds useful in the method of the invention may be collected in any of a number of standard collection tubes holding a calcium binding or chelating agent. Plastic tubes are preferred; however, glass-walled VACUTAINER TM tubes containing sodium citrate as a calcium binding agent are adequate in practicing most experiments supporting the invention. Freshly drawn samples are stored at ice temperature for up to 2–4 hours prior to further processing, and are checked for the presence of clots or hemolysis; any tubes containing clots are discarded. Plasma is obtained from the samples, using centrifugation procedures described in Example 4A. Plasma samples showing evidence of hemolysis are discarded, since hemolysis is known to shorten clotting time. Ideally, plasma samples are stored on ice and tested within 8 hours of collection. Alternatively, the samples may be frozen at −20° for testing within 1 week of collection. General methods used in collecting and processing blood samples for experiments in support of the invention are found in Example 4A.

Tests for anticoagulant activity may be carried out in vitro, wherein compound is added to an isolated plasma or blood sample, and effects on clotting time are measured. Anticoagulant activity may also be measured following administration of a compound to a whole animal. Such in vivo assessment of compound effects indicates the degree to which a drug is absorbed, distributed or biotransformed in the whole animal, and gives a measure of bioavailability.

A. Testing of Macrocyclic Compounds in Anticoagulant Assays

1. Plasma Clotting (Recalcification) Time

Plasma clotting or recalcification time measures the integrity of intrinsic coagulation system. A deficiency or inhibition of any of the factors of the intrinsic system results in prolongation of plasma clotting time. Both heparin and coumarin anticoagulants prolong plasma clotting time. In this assay, as described in Example 4D, plasma is mixed with calcium chloride at 37°, mixed and observed for clot formation.

Effects of compounds on clotting time in vitro

Results of studies in which various macrocyclic compounds were tested at three concentrations for effects on plasma clotting time in vitro, as described in Example 5 are shown in Table 3. Phenylic macrocyclic compounds KY225 and Y-47 exhibited the highest anticoagulant activity in this assay. Concentrations of 12.5 μg of each of these compounds produced anticoagulant activity equivalent to 7.54 and 5.68 μg of heparin, respectively. Phenylic derivatives Y-48, Y-77, Y-78, Y-100 and Y-1 and napthylic derivatives Y-20, KY-42, KY-1, KY-357 and KYY-19 were approximately equipotent in the assay, exhibiting activities about 1/10–1/20 that of heparin on a mass basis.

TABLE 3

| COMPOUND | CONCENTRATION (μg/ml) | | |
| --- | --- | --- | --- |
| | 12.5 | 25 | 50 |
| Phenyl derivatives | | | |
| KY-384 | 0.4 | 1.38 | 3.31 |
| Y-48 | 1.2 | 2.94 | 5.29 |
| KY-225 | 7.54 | >>[a] | >> |
| Y-47 | 5.68 | 15.27 | >> |
| KY-226 | — | — | 1.10 |
| Y-1 | 1.10 | 1.68 | 3.68 |
| Y-77 | 1.10 | 1.27 | 3.22 |
| Y-49 | — | — | 0.46 |
| Y-78 | 1.40 | 2.45 | 4.03 |
| Y-100 | 1.40 | 1.93 | 2.19 |
| Napthyl derivatives | | | |
| KY-3 | —[b] | 1.5[c] | 3.68 |
| KY-42 | 1.1 | 2.94 | 4.16 |
| Y-20 | 1.1 | 2.94 | 4.88 |
| KY-332 | — | — | 1.66 |
| KY-274 | 0.46 | 0.92 | 2.67 |
| KY-1 | 1.10 | 1.38 | 3.96 |
| Y-36 | 0.4 | 1.30 | 3.50 |
| KY-357 | 1.40 | 2.28 | 3.5 |
| KYY-19 | 1.40 | 2.28 | 4.03 |

[a]Anticoagulation activity is too high to be measured in the assay.
[b]Not detectable in anticoagulant activity.
[c]Values are expressed as heparin microgram equivalents; i.e., 25 μg KY-3 produces anticoagulant activity equivalent to 1.5 μg heparin.

Effects of Y-1 on clotting in vivo

The effects of Y-1 on clotting time following oral administration were studied in mice, as described in Example 13. Table 4 shows the results of a study in which two doses of 500 or 625 mg/kg each of Y-1 were administered to female Swiss-Webster mice at 30 minute intervals by gastric gavage. Blood samples were collected 2.5 hours following the initial dosing. Blood plasma was assayed for plasma clotting time. Compared to control (PBS-treated) animals, Y-1-treated animals showed increased clotting time, at both doses tested. For purposes of comparison, Y-1 (12 or 20 μg/ml) was also added directly to plasma samples from control animals, and plasma clotting times obtained were within the range of the times reported after oral administration of the compound.

Also shown in Table 4 is protamine reversal of the effects of Y-1 on plasma clotting time. This will be described in further detail in Part 4, below.

TABLE 4

Effect of Oral Y-1 on Recalcification Clotting Time and Reversal by Protamine Sulfate

| Y-1 Treatment (mg/kg) | Nutritional Status[1] | Clotting Time | |
|---|---|---|---|
| | | No Addition | + Protamine Sulfate (10.4 μg/ml) |
| 0[2] | N | 2.2 | n.d. |
| 2 × 500 | F | 4.5 | 2.4 |
| 2 × 625 | N | 3.1 | 2.3 |
| 2 × 625 | F | 3.4 | 2.4 |

[1]N, not fasted; F, fasted 24 hours prior to test
[2]Addition of Y-1 directly to control plasma gave clotting times of 3.2 min (12 μg/ml Y-1) and 4.1 min (20 μg/ml Y-1).

2. Prothrombin Time (PT) Assay

Prothrombin time assesses the patency of the extrinsic coagulation pathway, and measures the presence of factors II, V, VII, and X. This assay also serves as an indicator of levels of fibrinogen less than about 80 mg/dL. Prothrombin time is therefore useful in assessing therapy by coumarin anticoagulants, which inhibit production of factors II, VII, IX, and X. The presence of relatively high concentrations of heparin in blood samples also prolongs prothrombin time measurements.

Methods used in determining PT can be found in Example 4B. Briefly, the assay involves the addition of a tissue factor, such as thromboplastin-calcium reagent (Dade® Thromboplastin•C, Becton Dickinson) to a plasma sample. The duration of time for the time of addition until visible clot formation is observed is the PT.

a. Effects of In vitro Administration of Macrocyclic Compounds on Prothrombin Time Macrocyclic compounds KY-1, Y-1 and Y-49 were tested in a PT assay using human blood, as described in Example 6. Human plasma samples containing varying amounts of test compound (0–250 μg/ml, final concentrations) were tested clotting time subsequent to mixing with thromboplastin-calcium reagent.

Figure 30:
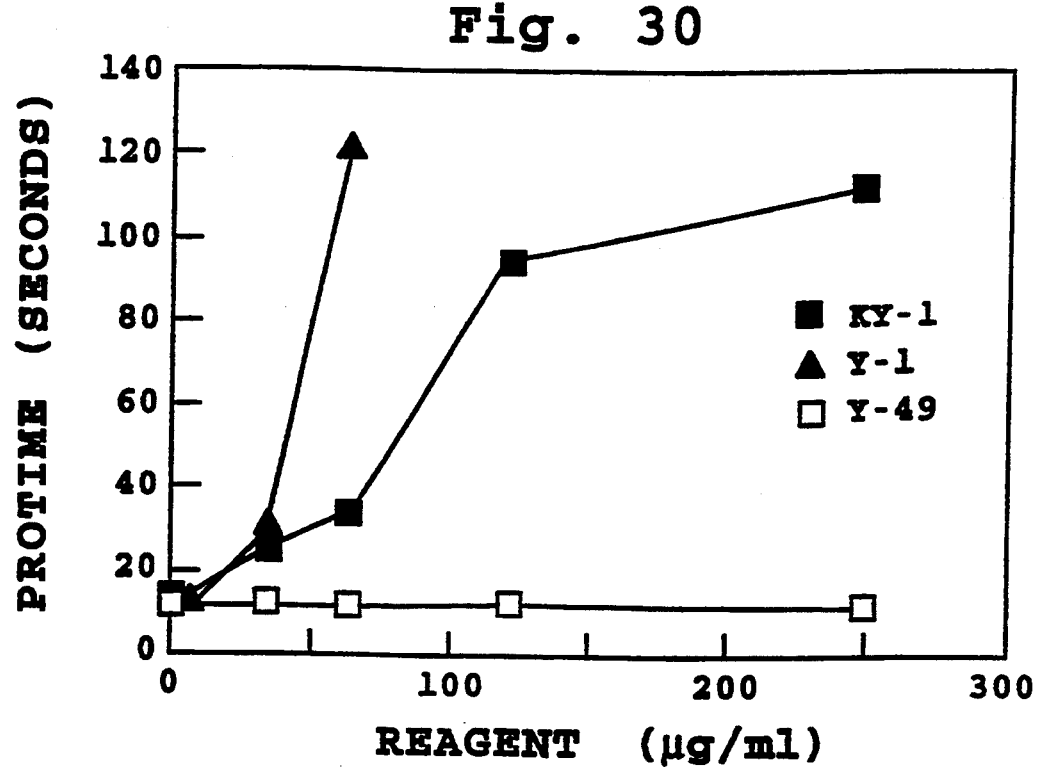
FIG. 30 shows a plot of prothrombin time in seconds (PT) as a function of concentration of KY-1, Y-1, and Y-49.

Of the several macrocyclic compounds tested in this assay, KY-1 exhibited highest activity (FIG. 30), exhibiting prolongation of prothrombin time at concentrations as low as 30 μg/ml. Y-1 showed intermediate activity. Y-49 was inactive at concentrations as high as 900 μg/ml (not shown in graph; but in raw data).

b. In vivo administration of macrocyclic compounds

Macrocyclic compounds of the invention were given intravenously to rats at doses of 5 and 10 mg/kg (2 rats/dose). Subsequently (5 hours following administration) venous blood samples were tested for PT, APTT, and fibrinogen. Table 5 shows the percent change in PT observed, as compared to the PT of blood plasma from saline-treated controls. Moderate increases in PT were observed for several of the compounds tested, most notably KY-225 and KY-226, partially oxidized macrocyclic compounds having 4 and 8 phenyl subunits, respectively.

TABLE 5

Effect of i.v. Administration of Macrycyclic Compounds on PT, APTT and Fibrinogen

| | Dose (mg/kg) | PT | APTT | Fibrinogen |
|---|---|---|---|---|
| Phenyl Derivatives | | | | |
| KY225 | 5 | 21 | 81 | N[1] |
| | 10 | 35 | >500 | −40 |
| KY226 | 5 | 25 | 93 | N |
| | 10 | 30 | >500 | −26 |
| Y1 | 5 | 12 | (67)[2] | 7 |
| | 10 | 28 | 66 | N |
| Y48 | 5 | 12 | 23 | −14 |
| | 10 | 11 | 138 | −17 |
| Y49 | 5 | N | 6 | N |
| | 10 | 7 | 27 | N |
| Y47 (SA) | 5 | 26 | (54) | N |
| | 10 | 16 | 90 | −17 |
| KY-384 (SA) | 5 | N | 70 | N |
| | 10 | 6 | 151 | −12 |
| Napthyl Derivatives | | | | |
| KY-1 | 5 | 20 | >500 | −21 |
| | 10 | 88 | >500 | −59 |
| Y20 | 5 | N | (82)[3] | N |
| | 10 | 10 | 29 | N |
| KY3 | 5 | N | N | N |
| | 10 | 10 | 38 | 13 |
| KY42 | 5 | 11 | 6 | N |
| | 10 | 19 | 61 | N |

[1]N, no effect
[2](3 and 131%)
[3](21 and 142%)

In a separate series of studies, Y-1 was administered at oral (p.o.) doses of 300 and 450 mg/kg to rats. Blood samples were taken and PT determinations made at times from 0.5 to 24 hours following administration, as described in Example 14. Results of these experiments are shown in Table 6, wherein significant increase (18%) in PT was observed 4 hours post-administration of 450 mg/kg Y-1 by gastric gavage. Reproducibility of this effect was tested by administering additional compound to some of the animals at 23 hours and testing PT at 24 hours. Once again, a significant (19%) prolongation of PT was observed. APTT prolongation was also observed at both doses of Y-1, as described below.

TABLE 6

Time Course of Effect of Oral Y-1 on Plasma PT and APTT

| Time after Administration (h) | PT[1] | APTT[2] |
|---|---|---|
| I. 300 mg/kg p.o. | | |
| 0[1] | 16.2 ± 0.2 | 13.0 ± 0.1 |
| 1 | 15.7 ± 0.2 | 20.3 ± 0.96 |
| 2 | 15.8 ± 0.1 | 19.7 ± 0.6 |
| 4 | 16.0 ± 0.3 | 18.5 ± 1.3 |
| 8 | 16.6 ± 0.1 | 19.5 ± 0.8 |
| 12 | 16.7 ± 0.2 | 15.4 ± 0.5 |
| 24 | 16.6 ± 0.2 | 14.3 ± 0.2 |
| II. 450 mg/kg p.o. | | |
| 0[1] | 14.8 ± 0.32 | 18.9 ± 1.3 |
| 0.5 | 15.4 ± 0.45 | 32.4 ± 1.8 |
| 4 | 17.5 ± 0.56 | 53.2 ± 9.1 |
| 8 | 15.1 ± 0.2 | 24.7 ± 0.7 |
| 16 | 15.5 ± 23.2 | 23.2 ± 1.5 |
| 24 | 15.0 ± 0.2 | 21.5 ± 0.5 |
| 24, repeat @ 23[3] | 17.6 ± 0.14 | 48.4 ± 5 |

[1]Zero time control animals given saline
[2]PT and APTT in seconds, mean of 4 animals ± SE.
[3]Animals previously treated with 450 mg/kg p.o. were given an additional oral dose of 225 mg/kg at 23 h.

3. Activated Partial Thromboplastin Time (APTT) Assay

The APTT assay is employed as a measure of the integrity of the intrinsic blood coagulation pathway, described above. It measure the presence of all coagulation factors in the intrinsic system except platelets and factor XIII, and is commonly used to monitor heparin therapy, since heparin binds to several of the factors of the intrinsic pathway (XIa, IXa, Xa, thrombin).

Detailed methods used in carrying out this assay can be found in Example 4C. Briefly, the plasma sample is mixed with activated thromboplastin, such as Actin® Activated Cephaloplastin Reagent (Becton Dickinson). The tube containing the mixture is placed in a 37° water bath for 3 minutes, prior to addition of calcium chloride. The sample is then observed for fibrin web formation.

a. Effects of macrocyclic compounds on APTT, in vitro

Figure 31:
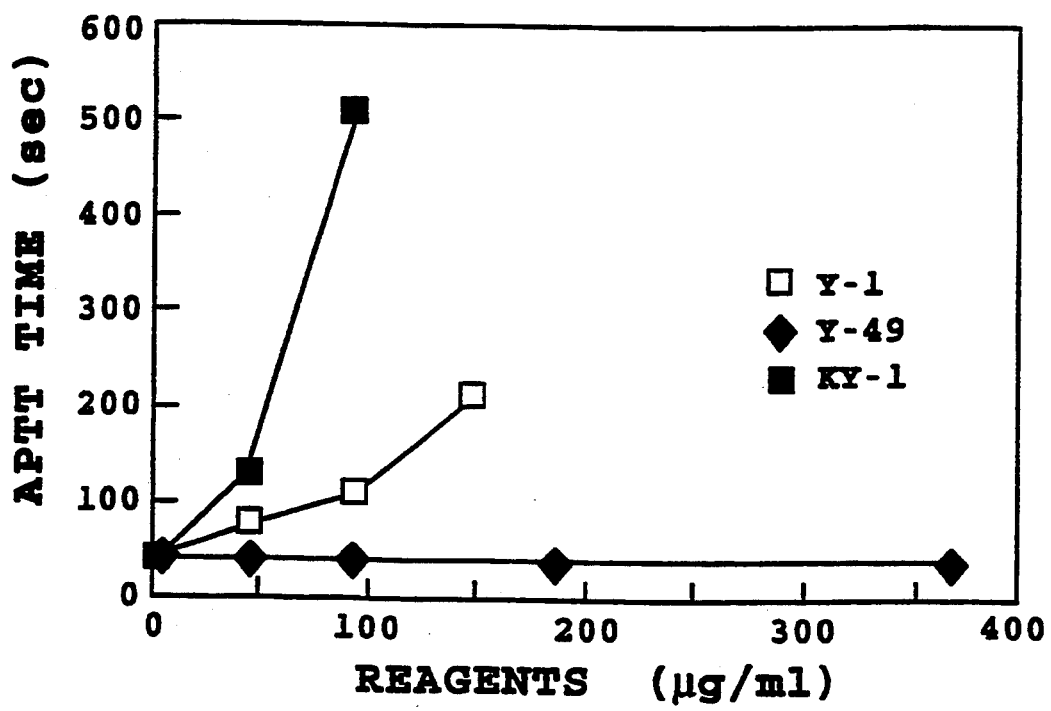
FIG. 31 shows a plot of activated partial thromboplastin time in seconds (APPT) as a function of concentration of KY-1, Y-1, and Y-49.

Platelet poor plasma (human) was used to test the effects of KY-1, Y-1 and Y-49 on APTT, as described in Example 7. FIG. 31 shows the results of these experiments, in which varying concentrations of each compound were tested, to yield concentration-effect plots. Of the three compounds tested, KY-1 produced the highest activity in this assay, and Y-1 exhibited less activity. Y-49 was inactive at the highest concentration tested.

In separate experiments, compound KY-1 was added to a human blood sample at a concentration of 50 $\mu$g/ml, and tested in a battery of standard clinical tests, one of which was APTT. A significant prolongation of APTT was observed, as shown in Table 12, part 9 of this section.

b. Effects of in vivo administration of macrocyclic compounds on APTT

Results from experiments in which rats were given macrocyclic polysulfonated compounds intravenously are shown in Table 5, above. Percent change in APTTs was determined, in comparison to untreated animals. With few exceptions, compounds described in the method of the invention exhibited a dose-dependent prolongation of APTT. Specifically, partially oxidized phenylic derivatives KY-225 and KY-226 exhibited the highest activities in this assay, while Y-48 and Y-42 followed, in descending order of activity. Compounds Y-49, Y-20 and KY-3 showed slight activity.

The observation that macrolcyclic polysulfonated compound treatment of whole animals resulted in prolongation of APTT was further examined, using rats as test animals. In this case, illustrated in FIG. 32, compound Y-1, was given intravenously to animals at a doses of 2.5 and 5 mg/kg, and blood samples were drawn from four different animals at various times following administration. APTT induced an immediate prolongation of APTT to approximately 300% of normal or higher, with the anticoagulant effect persisting up to 4–6 hours after the 2.5 mg/kg dose and remaining approximately 20% above normal at 12 hours after the 5 mg/kg dose. Data are expressed as percent of control values for each set of animals to normalize values obtained in different experiments.

Figure 33:
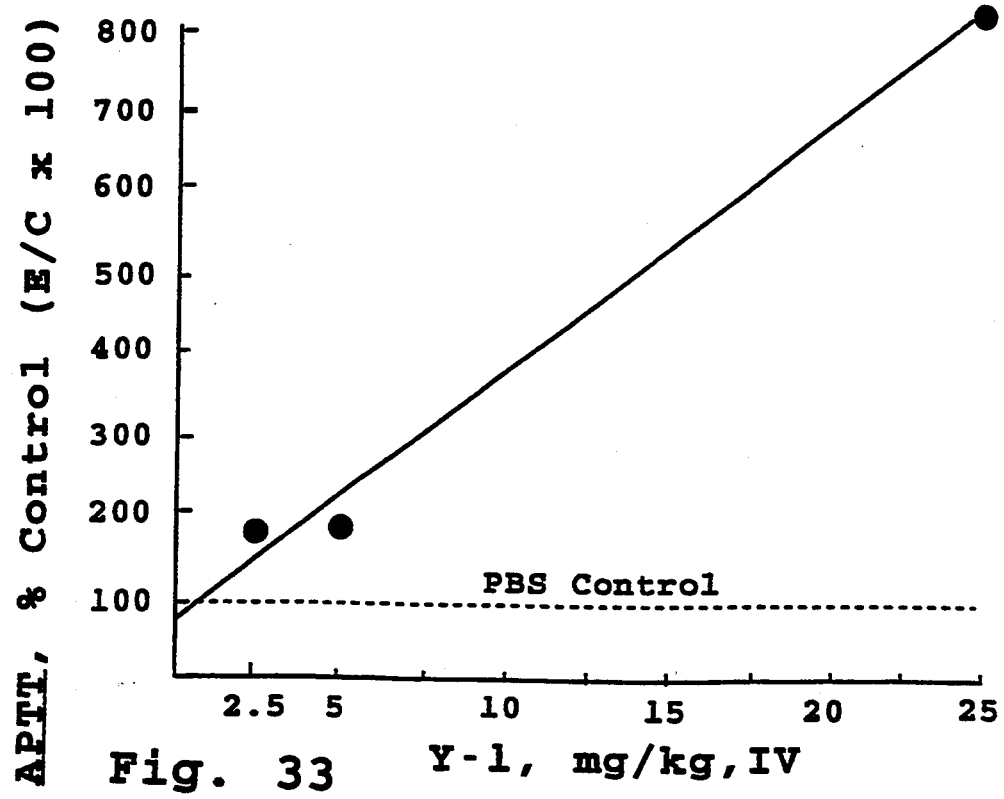
FIG. 33 shows a plot of percent control APTT as a function of i.v. injected dose of Y-1 in rats, where APTT is expressed as percent untreated control value run in parallel.

FIG. 33 illustrates the APTT dose-response relationship of Y-1 by plotting the 30-minute values of separate experiments in which 2.5, 5 and 25 mg/kg of Y-1 were administered intravenously to rats. High doses of Y-1 exerted profound effects on APTT, and the linearity of the dose-response curve demonstrates a high degree of predictability for the anticoagulant effect of Y-1.

The effects of oral administration of Y-1 were also tested, in assays described above for PT. As shown above in Table 6, a prolongation of APTT was observed at both 300 and 450 mg/kg Y-1. At the 450 mg/kg dose, this effect peaked at about 4 hours post-administration but was still apparent 16 hours post-administration. These studies confirmed that macrocyclic compounds of the invention are active when administered orally, and that their effects are relatively long-lasting.

4. Reversal by Protamine Sulfate of Anticoagulant Effects of Macrocyclic Compounds Blood or plasma samples treated with macrocyclic compounds of the invention were treated with protamines, to determine their effect on compound-induced anticoagulant activity, as assessed by several of the test assays used in experiments in support of the present invention. Murine plasma was tested for clotting time subsequent to oral administration of compound Y-1, as described in Example 13, and shown above in Table 4. In these studies, protamine sulfate was added to plasma samples from Y-1 treated animals at a concentration of 10.4 $\mu$g/ml. Addition of protamine sulfate to the samples resulted in reversal of the Y-1-induced prolongation of clotting times.

The efficacy of protamine sulfate in reversing the effects of Y-1 was further tested in rats, using the protocol described in Example 14, except that animals were given 25 mg/kg Y-1 intravenously. Twenty-six to twenty-eight minutes later, protamine sulfate was administered, also intravenously, at a dose of 25 mg/kg. Blood samples were collected 30 minutes after initial drug injection. Results of these studies are shown in Table 7. Treatment of rats with Y-1 resulted in elevation of PT and APTT to 161% and 831% of PBS control values, respectively. Protamine sulfate treatment resulted in a total reversal of the effects of Y-1 administration on PT and an almost total reversal of the effects on APTT.

TABLE 7

Effect of Intravenous Y-1 and Protamine Sulfate on PT and APTT in vivo[1]

| Treatment | N | PT (sec) | APTT (sec) |
| --- | --- | --- | --- |
| Saline | 4 | 14.8 ± 0.3 | 18.9 ± 1.3 |
| Y-1 (25 mg/kg) | 4 | 23.9 ± 0.7 | 157.1 ± 11.5 |
| Y-1 (25 mg/kg) + protamine sulfate (25 mg/kg) | 4 | 13.9 ± 0.1 | 27.6 ± 2.8 |

[1]Values expressed as mean ± std. error 4.5. Fibrinogen Assay

Figure 29:
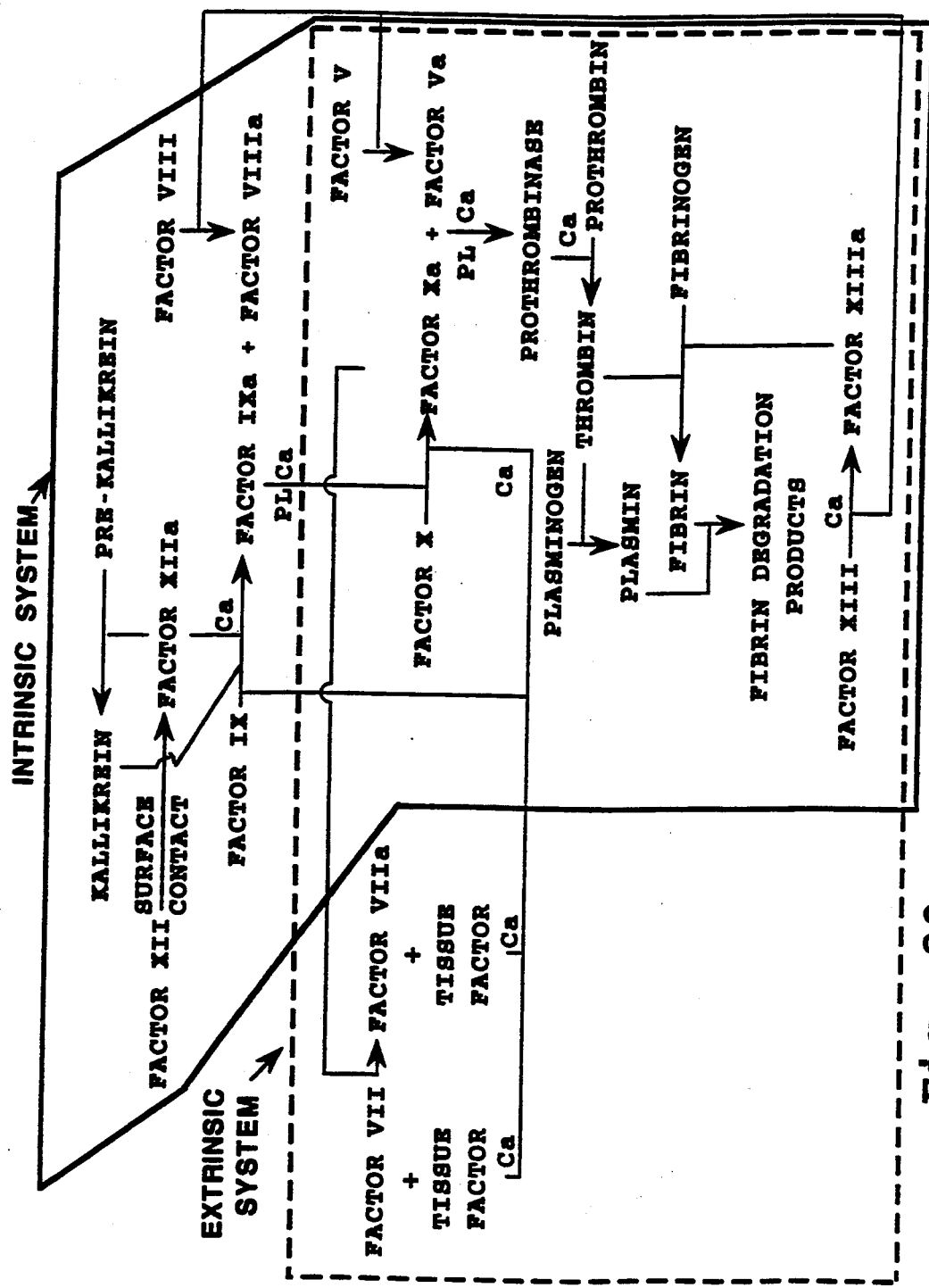
FIG. 29 shows a schematic of the cascade of biochemical events which occur in the coagulation process in mammalian blood.

Fibrinogen is the polymerize precursor of fibrin monomers, which spontaneously polymerize to initiate clot formation. In the coagulation cascade, as illustrated in FIG. 29, fibrinogen is converted to fibrin by the proteolytic action of thrombin. Fibrinogen content of blood may be effected by a number of insults. Lack of fibrinogen reduces clot formation. The presence of relatively high concentrations of heparin in samples can result in an artificially low value for fibrinogen content as determined by the thrombin time assay (see following section), due to inhibition by heparin of endogenous and added thrombin.

Fibrinogen content of blood can be measured by adding an excess of thrombin to a dilute plasma sample and recording clotting time, as described in Example 4E. Fibrinogen contents of plasma samples taken from rats previously given intravenous doses of various macrocyclic compounds are shown in Table 5, above. At higher doses, it is apparent that KY225, KY226, and to a lesser degree, Y-48 treatment resulted in a decrease in fibrinogen content of the blood. In addition, in a study in which KY-1 was added directly to human blood at a concentration of 75 µg/ml prior to assaying the blood plasma in a standard battery of clinical tests, a profound decrease in fibrinogen content was observed (shown in Table 12, below).

6. Thrombin Time

Thrombin time is another measure of the conversion of fibrinogen to fibrin, catalyzed in the blood by the enzyme thrombin. Prolonged thrombin times can be caused by a number of factors, including low fibrinogen levels, heparin, and other thrombin inhibitors such as fibrin degradation products.

The assay is carried out by adding a stock quantity of purified thrombin to platelet poor plasma samples, as described in Example 4G and recording the amount of time required for clot formation in the plasma.

Figure 34:
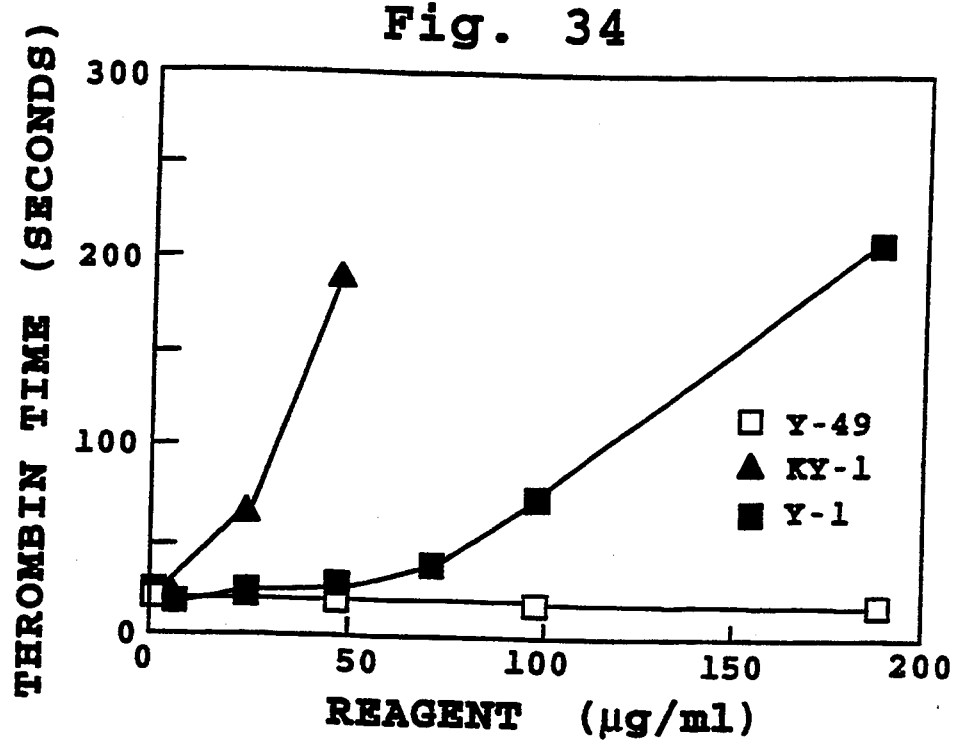
FIG. 34 shows a plot of thrombin time (TT) as a function of concentration of KY-1, Y-1, and Y-49.

Results of studies in which the compounds KY-1, Y-1 and Y-49 were tested for effects on TT, as described in Example 8, are shown in FIG. 34, where it is seen that the presence of KY-1 in the plasma sample markedly increased thrombin time, whereas Y-49 showed no activity at the concentrations tested.

7. Reptilase Assay (Atroxin Time)

Reptilase, an enzyme isolated from snake (*Bothrops atrox*) venom, which converts fibrinogen to fibrin, is not affected by heparin. It is therefore useful in testing for fibrinogen content of the blood of patients receiving heparin therapy. Blood from patients receiving a fibrinogen agent, such as streptokinase, exhibits prolonged atroxin and thrombin times. General procedures for carrying out reptilase assays are described in Example 4F.

Figure 35:
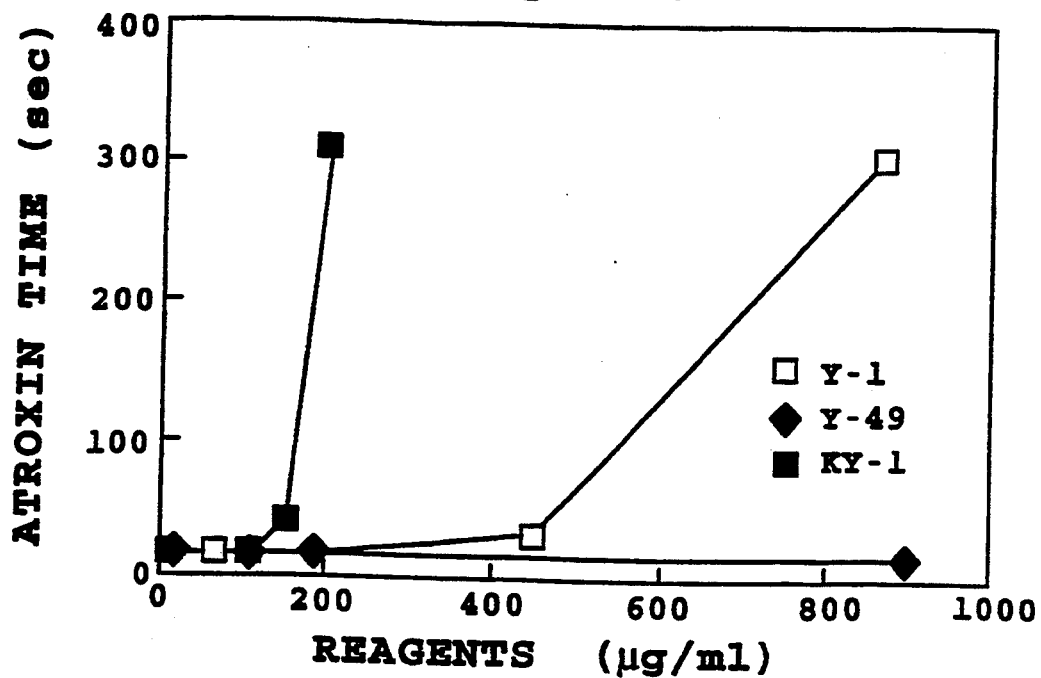
FIG. 35 shows a plot of atroxin time (AT) as a function of concentration of KY-1, Y-1, and Y-49.
Figure 36D:
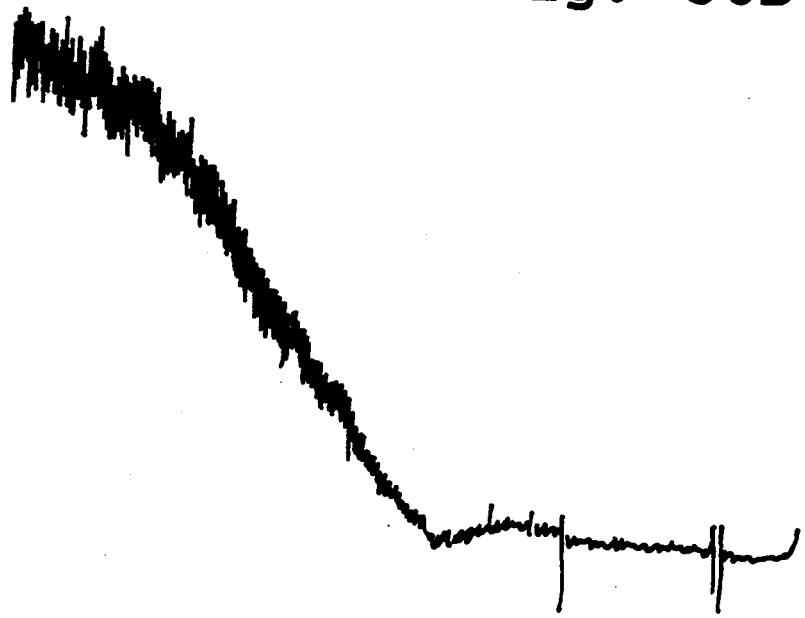
FIGS. 36 (A-G) show traces of change in optical density as a function of time in a platelet aggregation assay in which platelet aggregation was measured in the presence of collagen (A), collagen plus 24 (B) or 48 μg/ml (C) Y-49, collagen plus 24 (D) or 48 (E) μg/ml Y-1, collagen plus 24 (F) or 48 (G) μg/ml KY-1.
Figure 36E:
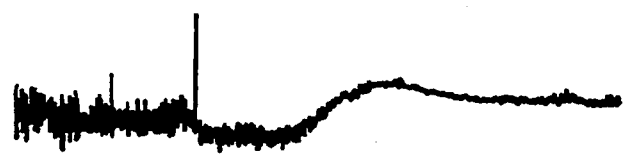
Figure 36F:
Figure 36G:
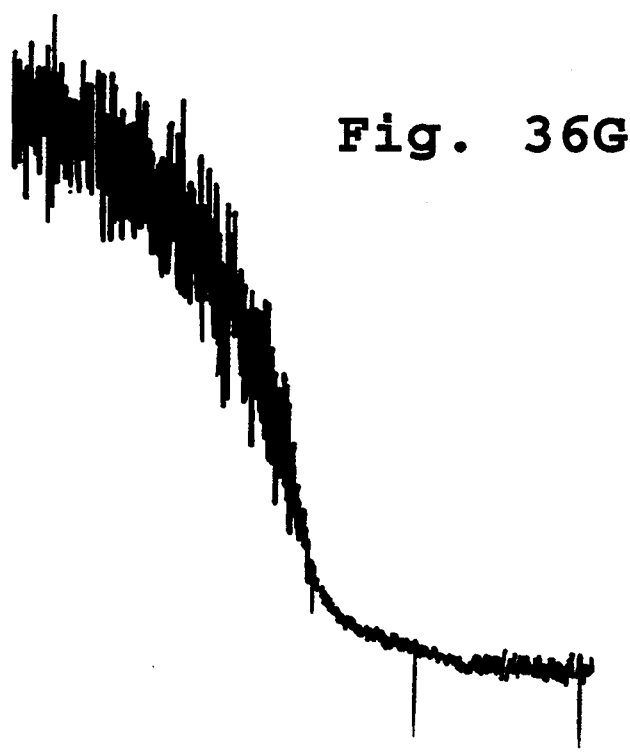

FIG. 35 shows the effects of increasing concentrations of KY-1, Y-1, and Y48 on atroxin time of human plasma in vitro. KY-1 prolongation of atroxin time only occured at concentrations approaching 150 µg/ml, a concentration much higher than that (25 µg/ml) required to significantly prolong thrombin time, as illustrated in FIG. 34. These results are similar to those observed with heparin, wherein high concentrations can be shown to prolong reptilase time, and indicate that the effect of KY-1 on fibrinogen content, reported in Part 4, above, can be explained at least in part by an indirect, heparin-like effect on the thrombin present in the assay.

8. Platelet Aggregation

Compounds, such as aspirin, which interfere with platelet aggregation result in prolonged bleeding time. Integrity of platelet aggregation in a blood sample can be measured by a characteristic change in optical density of a platelet rich plasma sample in response to platelet aggregation promoting factors, such as ADP or collagen as described in Example 4H. In studies on collagen activated platelet aggregation, carried out as described in Example 16, KY-1 and Y-49 at 24 µg/ml and 48 µg/ml concentrations had no measureable effect on collagen-induced aggregation (FIGS. 36, B, C, F, G). Y-1 at 24 µg/ml and 48 µg/ml showed significant inhibition of collagen induced platelet aggregation (FIG. 21 D, E).

9. Plasmin Activity

Figure 37A:
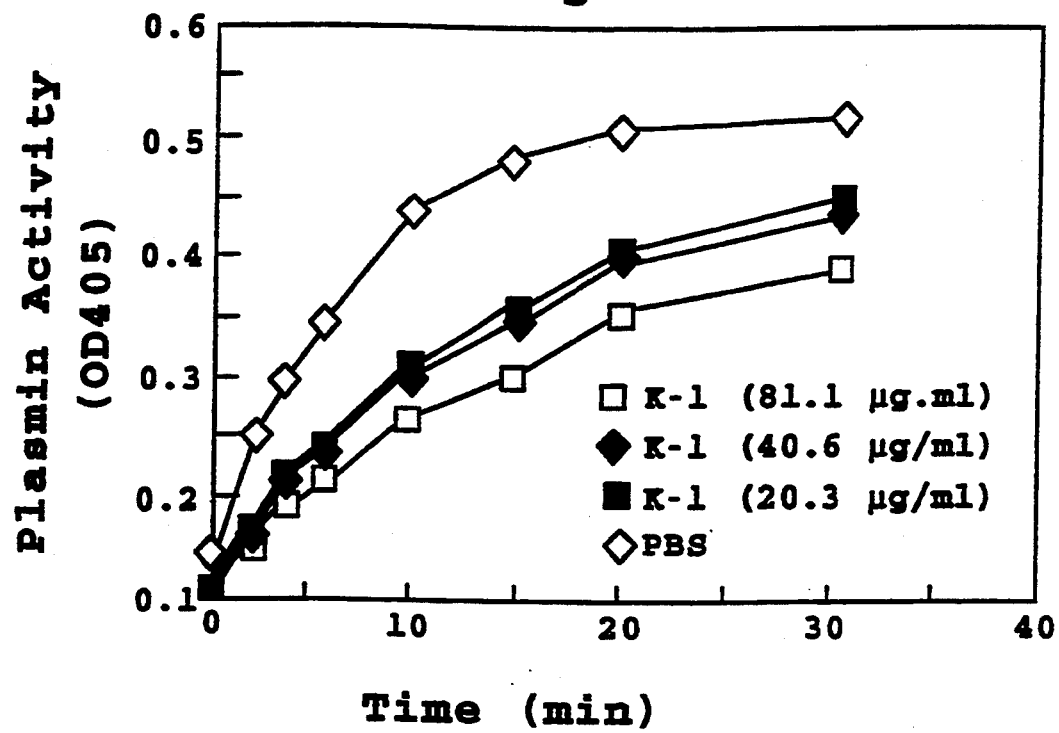
FIGS. 37 (A-B) show plots of effects of varying concentrations of Y-1 (A), KY-1 and heparin (B) on plasmin activity.
FIG. 37C is a bar graph summarizing the data of FIGS. 37A and 37B (C8=Y-1)
Figure 37B:
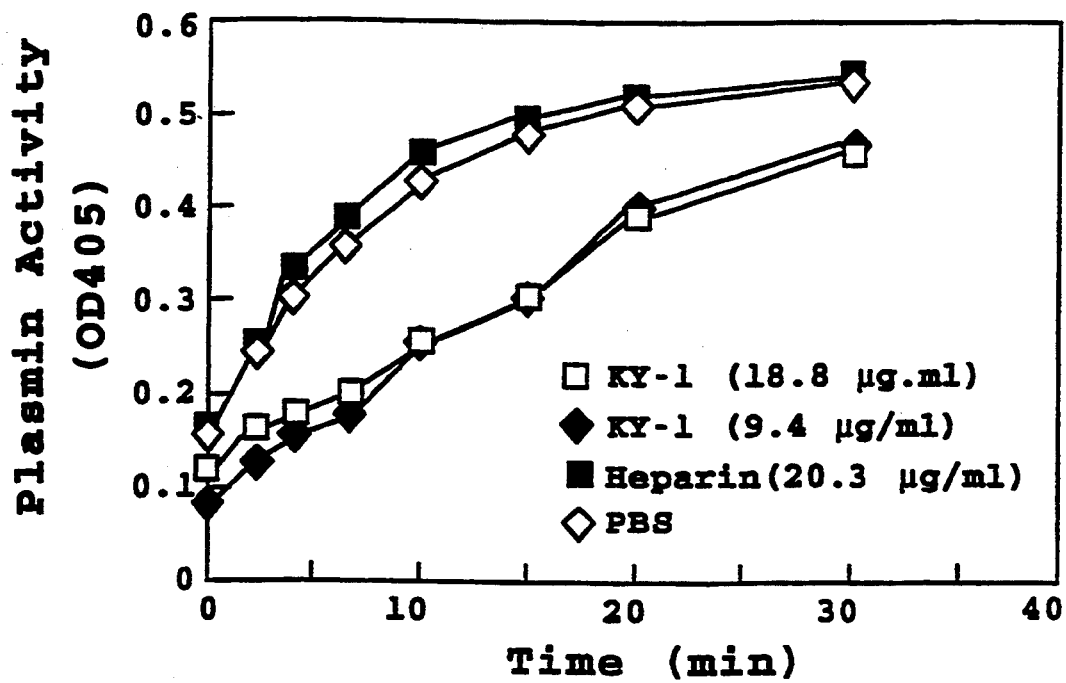

Compounds KY-1, Y-1 and Y-49 were tested for plasmin chromogenic effects, as described in Example 4I. FIGS. 37A and 37B show the results of these studies. Both KY-1 and Y-1 exhibited concentration dependent effects on plasmin chromogenic activity. In terms of enzymatic activity, measured as change in absorbance units per minute, the inhibitory effect of Y-1 at 20, 40, and 80 µg/ml were 15%, 28%, and 31% of control plasmin activity respectively (FIG. 37A); for KY-1 at 9 and 19 µg/ml, 35% and 52% of control activity. At higher doses of KY-1 and C8, the inhibition was still modest, KY-1 (64 µg/ml) caused 35% inhibition and Y-1 (233 µg/ml) 34% inhibition. Heparin at an equivalent anticoagulant dose in terms of TT had no inhibitory effect (FIG. 37B)

10. Effect of Y-1 on Venous Stasis Thrombosis in Rabbit

Antithrombotic activities of macrocyclic compounds of the invention are examined in a modified venous stasis thrombosis model (Fareed, et al., 1985) in which right and left jugular vein segments are isolated. Test macrocyclic compound is injected intravenously immediately after isolation of the segments. Alternatively, test compounds can be given orally or subcutaneously 3 hours prior to surgery. In experiments carried out in support of the present invention, compound Y-1 was administered intravenously at 0.5, 1, 2.5, 5, and 10 mg/kg following isolation of the veins, as detailed in Example 17. After compound Y-1 has been allowed to circulate for a prescribed period of time, a thrombogenic challenge consisting of prothrombin complex concentrate (PCC; KONYNE ®) is given, and Russel's viper venom (RVV) in cephalin is given. These compounds are allowed to circulated for 20 seconds, then the isolated jugular vein segments are ligated and stasis produced. After a pre-determined stasis time (as indicated in Table 8 and Table 9), the isolated segments are removed and examined for blood clots (thrombi). In studies examining the effects of oral or subcutaneous administration of compound, the surgical procedure was initiated 3 hours post administration. Oral administration is performed via an infant feeding tube, placed in the stomach. Subcutaneous injections are performed at the fat tissue of the lower abdomen. During the whole absorption and circulation time the rabbits are kept under anesthesia. Clot formation is visually graded using a ± system. In this system, "−" represents blood only with no evidence of clotting, "+" indicates some small clots but mostly blood, "++" indicates mostly small but some medium clots, "+++" indicates a large clot with some blood, while "++++" indicates a fully formed, casted clot with no blood. In order to analyze the data, the ± grades are transformed into numerical values using the following scale:

```
   −  = 0
   +  = 1.25
  ++  = 2.5
 +++  = 5.0
++++  = 10.0
```

After transformation, mean values were determined from the average of the left and right stasis scores. Results of experiments using intravenous administration of Y-1 are shown in Table 8 and Table 9, in which stasis times of 10 and 20 minutes were examined. As shown in Table 8, using a stasis time of 10 minutes, reduction of thrombus formation was observed at a dose of 0.5 mg/kg, Y-1, with no thrombi observed at doses of 2.5 and 5 mg/kg, when stasis was produced 5 minutes after Y-1 administration. Slightly higher doses were required for reduction of thrombi, when either stasis time of Y-1 circulation time was increased, as seen in Table 9. Here, even one hour after Y-1 administration, significant and dose dependent reductions in thrombus formation were observed. In the 10 minutes stasis protocol, no clots were observed at a dose of 10 mg/kg Y-1.

TABLE 8

Intravenous Antithrombotic Action of Y-1 In a Rabbit model of Stasis Thrombosis[a]

| Dose mg/kg | Clot Score |
| --- | --- |
| 0 | 8.25 |
| 0.5 | 3.75 |
| 1.0 | 1.25 |
| 2.5 | 0 |
| 5.0 | 0 |

[a]Experiments carried out 5 minutes after the administration of Y-1.

TABLE 9

Intravenous Antithrombotic Actions of Y-1[a]

| Dosage mg/kg | Jugular Vein Thrombosis | |
| --- | --- | --- |
| | 10 min. statis | 20 min. statis |
| 0 | 7.5 | 8.75 |
| 0.5 | 6.8 | 7.5 |
| 1.0 | 5.7 | 6.5 |
| 2.5 | 3.8 | 4.8 |
| 5.0 | 2.5 | 3.0 |
| 10 | 0 | 2.5 |

[a]All studies were carried out 60 minutes after the administration of Y-1.

Table 10 shows a comparison of antithrombotic activity of compound Y-1 and those of other anticoagulant compounds similar activities in in vitro assays as reported above, where all compounds were administered orally at 10 mg/kg, two hours prior to thrombus induction. LMW heparin indicates low molecular weight heparin. Compound LW 10082 is aprosulate, a sulfated lactobionic acid (Luitpold-Werk, Germany) which, like Y-1, activates heparin cofactor II (HC-II) mediated inhibition of thrombin, as evidenced by an assay using commercially available dermatan sulfate kit.

TABLE 10

A Comparison of the Oral Antithrombotic Actions of Heparin, LMW Heparin, LW 10082 and GL Y-1[a]

| Agent | Clot Score |
| --- | --- |
| Heparin | 8.25 |
| LMW Heparin | 8.75 |
| LW 10082 | 8.0 |
| GL 522-Y-1 | 2.5 |
| Saline | 8.25 |

[a]Two hours after oral administration of each agent at a dose of 10 mg/kg.

11. Effect of Y-1 on Hemorrhage

This section describes a method for determining the activity of a compound in prolonging bleeding in an animal model. Prolongation of bleeding is considered an indicator of the hemorrhagic potential of an agent (Cade, et al., 1984). Commonly used antithrombotic agents such as heparin and coumarin anticoagulants have a tendency to produce hemmorrhage as a side effect of therapy.

A rabbit bleeding model used in determining bleeding prolongation due to drug is detailed in Example 18. Briefly, a rabbit is anesthetized, and the ear is immersed in a saline bath at 37° C. An area of the ear is selected that is free of major blood vessels, and incisions of full thickness are made. The rabbit's ear is then immersed in the saline is collected in a bottle and the total red cells were counted using a Coulter cell counter. Results are reported as the number of red blood cells present per liter of saline.

Table 11 shows a comparison of bleeding with clot score in rabbits subjected to the venous stasis thrombosis procedure two hours following oral administration of compound Y-1. At a dose (10 mg/kg) effective to significantly reduce clot size in the venous stasis thrombus model, bleeding was increased only about 1.5 fold.

TABLE 11

Effect of Oral Y-1 on Bleeding and Antithrombotic Activity in Rabbits[a]

| Dosage (mg/kg) | RBC 10$^9$/L Bleeding | Clot Score |
| --- | --- | --- |
| 0 | 0.12 | 8.25 |
| 2.5 | 0.10 | 7.0 |
| 5.0 | 0.13 | 5.2 |
| 10 | 0.18 | 2.5 |

[a]Experiments carried out two hours after oral administration of Y-1 at the dosages indicated.

12. Profiles of KY-1 in Clinical assays on Human blood samples

A human blood sample was drawn, and KY-1 was added to a final concentration (75 μg/ml), prior to transport of the sample to a licensed clinical testing lab for a battery of standard clinical assays. Results of these tests are shown in Table 12. It is apparent that at the concentration of compound used, all standard assays registered abnormal coagulation parameters.

TABLE 12

Effect of KY-1 75 μg/ml) on Coagulation of Human Plasma: Comparison of Clinical Assays

| Assay | KY-1 Treated | Normal Range |
| --- | --- | --- |
| Prothrombin Time (PT) | 26.8 sec | 11–13 sec. |
| APPT | >300 sec | 24–34 sec |
| Fibrinogen | <30 mg/dl | 160–350 mg/dL |
| Thrombin Time | >100 sec | 13–17 sec |
| Reptilase Time | 48.1 sec | 9.6–14.0 sec |

Table 13 shows a clinical test profile of KY-1 at concentrations ranging from 2–1000 μg/ml in human plasma samples. Tests used included protrombin time (PT), APTT, and thromin time (TT), as described above, as well as the HEPTEST (detailed in Example 4J) and the tissue factor clotting time (TFCT).

TABLE 13

In Vitro Laboratory Profile of KY-1

| Drug Concentration (μg/ml) | PT (Sec) | APTT (Sec) | HEPTEST (Sec) | TFCT 5 OU (Sec) | TT 1 OU (Sec) |
| --- | --- | --- | --- | --- | --- |
| 1000 | >300 | >300 | >300 | >300 | >300 |
| 500 | >300 | >300 | >300 | >300 | >300 |
| 250 | >300 | >300 | >300 | >300 | >300 |
| 125 | 28.7 | >300 | 34.9 | 152.9 | 137.8 |
| 62 | 17.3 | >300 | 23.3 | 64.8 | 33.9 |

TABLE 13-continued

| | In Vitro Laboratory Profile of KY-1 | | | | |
|---|---|---|---|---|---|
| Drug Concentration (μg/ml) | PT (Sec) | APTT (Sec) | HEPTEST (Sec) | TFCT 5 OU (Sec) | TT 1 OU (Sec) |
| 31 | 13.1 | 104.4 | 22.0 | 44.2 | 18.4 |
| 16 | 18.4 | 60.9 | 21.3 | 35.3 | 16.3 |
| 8 | 11.2 | 44.3 | 20.9 | 32.4 | 12.4 |
| 4 | — | 35.9 | 20.3 | 30.4 | 10.9 |
| 2 | — | 31.3 | 20.7 | 30.7 | 10.7 |
| 0 | 11.6 | 31.9 | 17.9 | 31.9 | 10.4 |

Stock drug was prepared in saline. Drug was supplemented to NRP in a 1:10 dilution than then serially diluted with plasma to obtain the above concentrations and immediately assayed.

13. Clinical test profiles of Y-1 in human and non-human blood samples

Blood from several non-human species was collected, processed and tested in test assays described above for the clinical assay of Y-1 in human blood samples. The assays used are as described in the previous section. Additionally, Y-1 treated plasma was tested in the chromogenic anti-Xa assay (AXa) detailed in Example 4L and in the chromogenic anti-IIa assay described in Example 4K. Results of these assays are shown below.

TABLE 14

Hemostatic Profile of Compound "Y" After In Vitro Supplementation of Human, Monkey, Dog, Rabbit and Rat Plasmas

| C "Y" Concentration | PT | APTT | HEPTEST | TT (5 U) | CaTT (5 U) | AXa | AIIa |
|---|---|---|---|---|---|---|---|
| HUMAN PLASMA | | | | | | | |
| 500.0 μg/ml | 208.8 | 300.0 | 300.0 | 300.0 | 300.0 | 3.3 | 44.3 |
| 250.0 μg/ml | 44.8 | 245.6 | 140.3 | 47.7 | 19.3 | 7.2 | 40.2 |
| 125.0 μg/ml | 24.3 | 128.2 | 54.2 | 24.3 | 13.2 | 13.6 | 29.4 |
| 62.5 μg/ml | 17.2 | 88.8 | 30.7 | 21.3 | 12.0 | 21.4 | 25.3 |
| 31.2 μg/ml | 14.0 | 64.0 | 21.5 | 19.7 | 11.6 | 1.1 | 17.2 |
| 0.0 μg/ml | 10.5 | 32.9 | 18.5 | 19.0 | 11.9 | 0.0 | 0.0 |
| MONKEY PLASMA | | | | | | | |
| 500.0 μg/ml | 44.3 | 186.1 | 300.0 | 300.0 | 74.8 | 17.9 | 40.8 |
| 250.0 μg/ml | 17.8 | 39.8 | 63.9 | 45.8 | 19.4 | 0.5 | 21.8 |
| 125.0 μg/ml | 13.3 | 27.8 | 25.3 | 33.2 | 18.3 | 0.5 | 17.6 |
| 62.5 μg/ml | 11.7 | 24.8 | 21.7 | 30.8 | 18.8 | 1.3 | 9.2 |
| 31.2 μg/ml | 10.0 | 22.5 | 19.5 | 28.5 | 16.5 | 5.3 | 3.4 |
| 0.0 μg/ml | 9.5 | 20.0 | 19.4 | 26.5 | 15.4 | 0.0 | 0.0 |
| DOG PLASMA | | | | | | | |
| 500.0 μg/ml | 24.1 | 60.1 | 300.0 | 300.0 | 43.8 | 39.9 | 53.1 |
| 250.0 μg/ml | 10.8 | 18.3 | 65.3 | 54.9 | 15.8 | 5.7 | 49.6 |
| 125.0 μg/ml | 9.4 | 15.0 | 42.2 | 34.3 | 14.8 | 12.7 | 29.1 |
| 62.5 μg/ml | 8.8 | 14.8 | 31.7 | 29.7 | 12.8 | 7.1 | 18.3 |
| 31.2 μg/ml | 7.5 | 13.8 | 28.5 | 24.5 | 11.5 | 9.4 | 17.5 |
| 0.0 μg/ml | 6.9 | 13.9 | 24.5 | 20.5 | 9.9 | 0.0 | 0.0 |
| RABBIT PLASMA | | | | | | | |
| 500.0 μg/ml | 7.3 | 45.4 | 50.3 | 75.2 | 18.3 | 6.2 | 43.4 |
| 250.0 μg/ml | 5.9 | 29.8 | 33.5 | 36.7 | 15.2 | 0.0 | 37.7 |
| 125.0 μg/ml | 5.8 | 27.3 | 32.7 | 35.7 | 14.3 | 3.8 | 9.1 |
| 62.5 μg/ml | 5.7 | 26.0 | 31.7 | 32.3 | 13.5 | 8.4 | 4.2 |
| 31.2 μg/ml | 5.7 | 28.5 | 32.2 | 34.0 | 13.0 | 4.4 | 2.0 |
| 0.0 μg/ml | 4.8 | 41.4 | 32.1 | 30.9 | 11.9 | 0.0 | 0.0 |
| RAT PLASMA | | | | | | | |
| 500.0 μg/ml | 88.8 | 300.0 | 300.0 | 300.0 | 300.0 | 2.4 | 55.2 |
| 250.0 μg/ml | 27.6 | 81.3 | 300.0 | 300.0 | 300.0 | 0.9 | |
| 125.0 μg/ml | 19.3 | 42.8 | 189.0 | 300.0 | 171.2 | 14.0 | 49.1 |
| 62.5 μg/ml | 17.0 | 29.5 | 71.6 | 300.0 | 96.5 | 0.0 | 43.0 |
| 31.2 μg/ml | | | | | | | |
| 0.0 μg/ml | 14.7 | 17.2 | 54.5 | 116.0 | 24.0 | 0.0 | 0.0 |

14. Summary of Effects of Macrocyclic Compounds on Blood Coagulation

KY-1 and Y-1 serve as prototype napthyl and phenyl macrocyclic compounds in analyzing the effects of these classes of compounds on blood coagulation. Both compounds were observed to prolong overall clotting time, with approximately equivalent potencies (Table 3); as described above, and summarized below, these compounds may have slightly different predominant mechanisms of action.

Figure 38A:
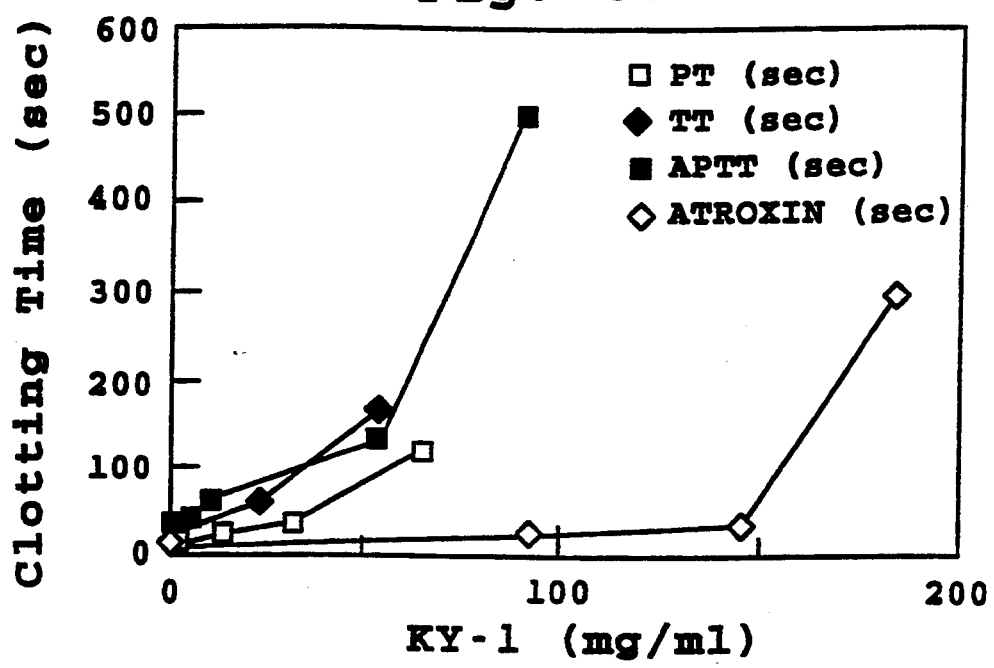
Figure 38B:
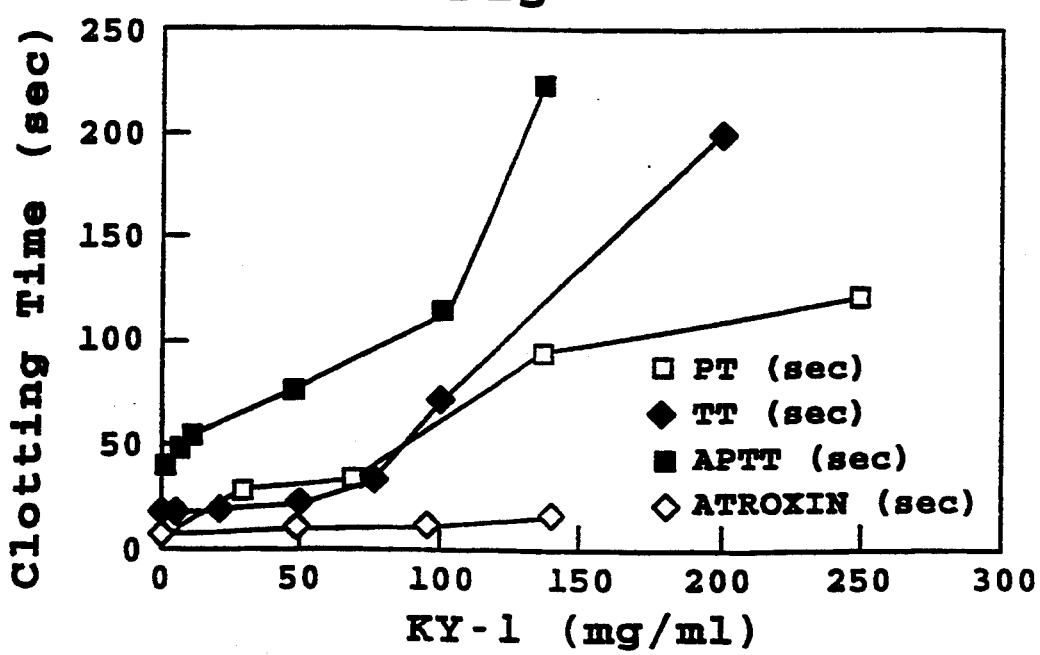
Figure 39A:
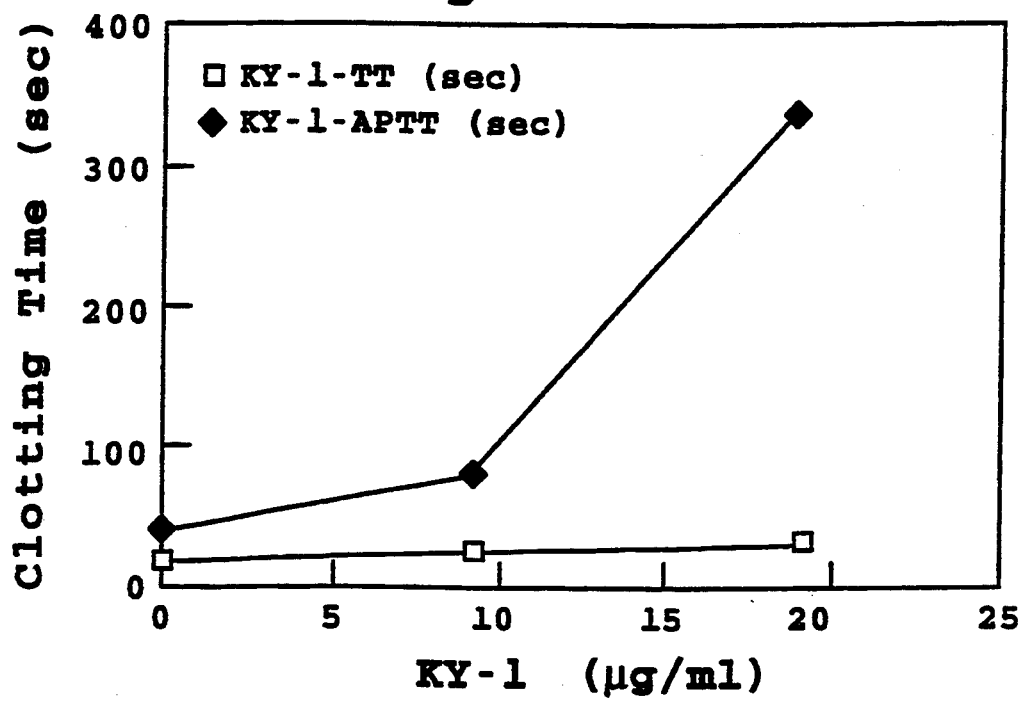
FIGS. 39A and 39B show plots of TT and APTT as a function of concentration of KY-1 (39A) or heparin (39B) concentration in plasma.
Figure 39B:
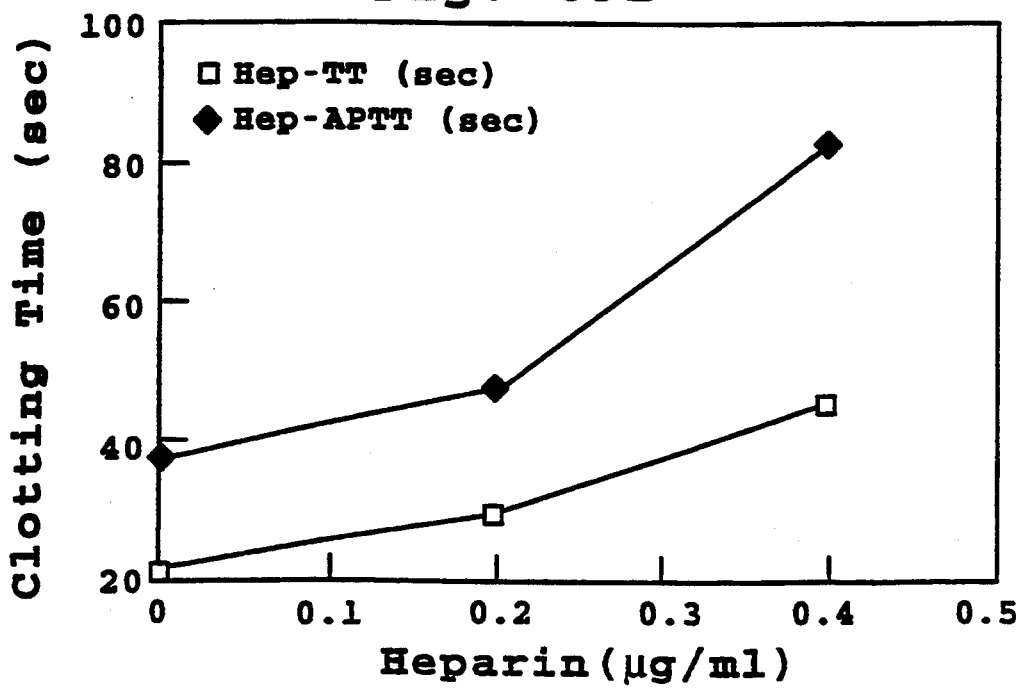

KY-1 significantly prolonged PT, APTT, TT and AT in vitro (FIG. 38). However, concentration-effect studies (0.6–180 μg/ml) clearly showed that the KY-1 prolongation of AT only occurred at concentrations approaching 150 μg/ml, similar to a heparin-like effect. To determine if this was entirely due to a heparin-like effect, a further experiment was done in which heparin and KY-1 were tested at concentrations that gave similar prolongation in thrombin times (FIG. 39 A–B). KY-1 at 19 μg/ml which gave TT of 38 sec showed marked prolongation of APTT to >300 sec, while heparin at 0.41 μg/ml with TT of 49 sec gave APTT of 81 sec. These data suggest that the KY-1 anticoagulant effect is not entirely due to a heparin-like effect.

Figure 40:
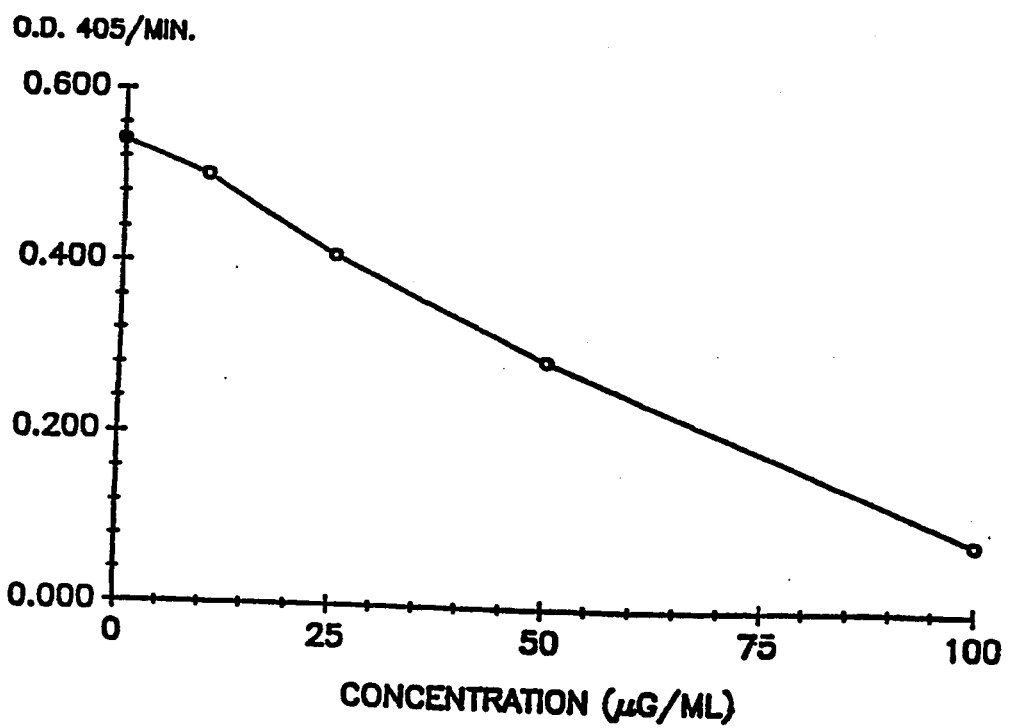
FIG. 40 shows activation of heparin cofactor II activity in the dermatan sulfate kit assay.

Y-1 also prolonged PT, APTT, TT and AT. In contrast to KY-1, the effect of Y-1 on AT was minimal, with no prolongation at 400 μg/ml (FIG. 35). Concentration-effect studies showed significant prolongation of both PT and PTT ($\approx 2\times$baseline) at 20 μg/ml with no significant prolongation in TT at this concentration. TT prolongation was only seen at $\geq 75$ μg/ml (FIG. 34). These data suggest that the anticoagulant effect of Y-1, at $\approx 20$ μg/ml range, is most likely not due to a heparin-like effect. The simultaneous prolongation of PT and aPTT suggests that Y-1 may be directed against the common pathway. Potential targets include Factor X, Factor V, prothrombin (Factor II) or phospholipids. Additionally, Y-1 inhibited collagen-induced platelet aggregation (FIGS. 36D and 36E), and was found to activate heparin cofactor-II activity in the dermatan sulfate kit assay (FIG. 40). Activity of compound Y-1 in the chromogenic anti-IIa and chromogenic anti-Xa assays (Table 14) serves as evidence that Y-1 serves to effectively decrease activity of these factors, directly and/or by decreasing production of the factors.

Compound Y-1 was also evaluated in rabbit models of venous thrombus formation and bleeding, as detailed in Examples 17 and 18, respectively. This compound was notable for its ability to inhibit thrombus formation at an oral dose which increased bleeding less than two fold over control values, as described above.

The activity profiles of Y-1 and KY-1, which are taken to be representative of the macrocyclic phenyl- and macrocyclic napthyl derivatives respectively, suggest that the compounds may be preferred in different indications requiring anticoagulant therapy. For example, in those cases, such as in certain forms of valvular heart disease, in which concurrent antiplatelet and anticoagulant therapy is indicated, compounds exhibiting the Y-1 activity will be indicated.

Figure 32:
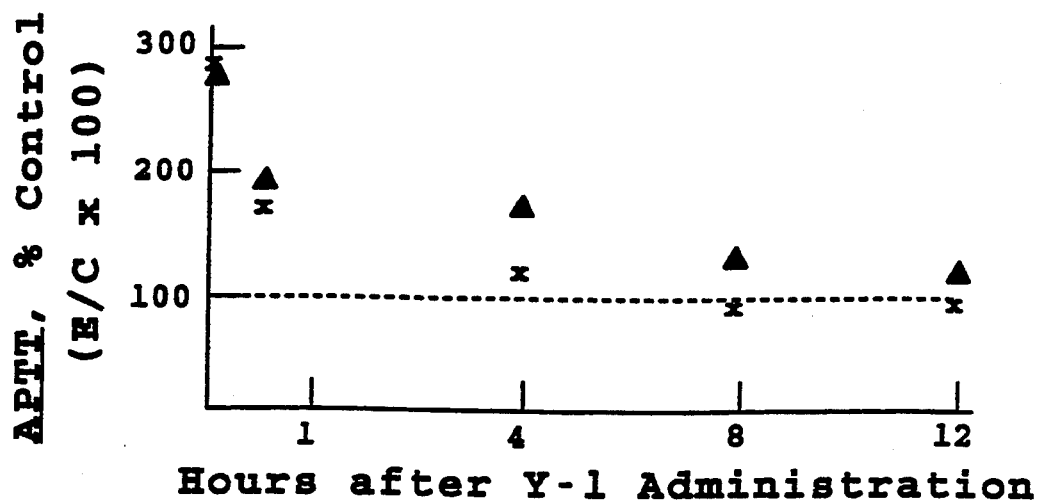
FIG. 32 shows a plot of APTT determined at various times after intravenous injection of 2.5 mg/kg (X) or 5.0 mg/kg ▲ Y-1 in mice, where APTT is expressed as percent untreated control sample value run in parallel.

Both Y-1 and KY-1 were shown to be active in vivo, when administered either parenterally or orally. Peak effects after oral administration were dose dependent and were observed between about 0.5 and 4 hours following oral administration of 450 mg/kg Y-1, as assessed by APTT (Table 6). The apparent distribution half-life of this compound, following intravenous administration of 2.5 and 5 mg/kg, as assessed by APTT, is less than an hour, and elimination half-life about 3–4 hours with APTT remaining above control levels for at least 4 hours in a dose-related manner (FIG. 32).

Studies using Y-1 demonstrated that, although as stated above, the compound does not appear to have a heparin-like mechanism of action, its effects can be antagonized by protamine sulfate. This finding suggests relatively convenient, approved antidote to accidental overdosage with the compound.

IV. Method of Treatment

In the method of treatment of the invention, an aryl macrocyclic compound of the type described in Section II is administered to the bloodstream of a patient at risk for developing a thrombus. As described above, the compounds of the invention appear to have direct effects on a factor or factors present in the coagulation cascade, by which they produce their anticoagulant and anti-thrombotic effects. Additionally, compound Y-1, exemplifying calixarene compounds of the invention, was found to exhibit anti-platelet activity.

The main routes of drug delivery are intravenous and oral, with the preferred route being oral. Other drug-administration methods, such as intra-arterial, subcutaneous, or nasal insufflation, which are effective to deliver the drug into the bloodstream, are also contemplated by the invention.

The dosage which is administered is a pharmaceutically effective dose, defined as a dose effective to prolong coagulation time of blood in a patient. As seen above, compound concentrations in the plasma in the range of 10–100 μg/ml are generally effective to inhibit coagulation, as assessed by plasma recalcification time, APTT or PT, in vitro. Thus, for most indications, and effective dose would be one which produces a concentration of compound in this range in the blood.

More preferably, a dose of drug will be selected which exhibits anti-thrombotic activity, while minimally affecting systemic coagulation and, hence, lessening hemorrhagic potential in a patient. As described above, such a dose can be selected by evaluating the compound in a thrombus formation test, such as the rabbit venous stasis model detailed in Example 18, and in a bleeding test, such as the rabbit ear bleeding model detailed in Example 19.

One consideration in any anticoagulant therapy regimen, in view of its potential for producing life-threatening hemorrhage, is identifying an antidote to the therapy; that is, a mode of abrupt discontinuation of action of the compound in the event of overdosage of the compound. In the method of treatment of the present invention, an effective antidote, protamine sulfate, has been identified. In the event of overdosage, it is anticipated that an amount of protamine sulfate approximately equal to or less than the amount of compound administered, would be effective to antagonize the effects of the drug, the amount of protamine sulfate dependent on the time after administration of the compound.

A. Treatment by Intravenous Administration

Studies on the pharmacokinetics and efficacy of intravenously administered macrocyclic compounds of the invention are described above. Briefly, aryl macrocyclic compounds produce antigoagulant effects for 4 hours or longer in a dose-related manner following intravenous administration.

B. Treatment by Oral Administration

Studies in support of the present invention, described above, show that following oral administration (gavage), macrocyclic compounds of the invention produce significant anticoagulant activity for 4 or more hours, the duration of effect being dependent on the dose administered.

The following examples illustrate methods of preparing tetrameric macrocyclic compounds, in accordance with the invention, and their use in inhibiting blood coagulation. The examples are intended to illustrate but not limit the scope of the invention.

Materials

All chemical reagents were obtained from Aldrich Chemical Co., or from other commercial sources.

EXAMPLE 1

Preparation of Naphthalene Macrocyclic Compounds

A. KY-1 ($R_1$=OH, $R_2$=SO$_3$Na, $R_3$=H, $R_4$=>CH$_2$)

To a 41 mM aqueous solution (50 ml) of disodium chromotropic acid, 15 ml of 37% formaldehyde was added, giving a final molar ratio of 5:1 formaldehyde:chromotropic acid. The mixture was reacted with stirring in a stoppered flask at room temperature for 1 week. The resulting dark red solution (70 ml) was filtered under vacuum, and the filtrate, after being concentrated was precipitated by adding 200 ml of acetonitrile. The precipitated product was collected by filtration and taken to dryness under vacuum. The yield of KY-1 was 95%. The compound was characterized as follows:

Melting point (M.P.)>300° C.; HPLC in CH$_3$CN/MeOH/H$_2$O/TFA: 14'48" single broad peak; (IR/KRr)=3425 (OH), 1638 (Ar), 1181, 1044 (SO$_3$) cm$^{-1}$; UV (H$_2$O): 238.0, 358.5 nm Mol Weight: 1505 (M+1) by mass spectroscopy; H$^1$ NMR(CD$_3$OD), chemical shifts on the δ scale: 5.20 (CH$_2$, 8.01 (ArH) ppm; C$^{13}$ NMR (D$_2$O), chemical shifts on the δ scale: 27.19, 120.18, 121.69, 122-06, 122-67, 133-30, 142.97, 154.42 and 181 ppm. Analysis: (C$_{22}$H$_{10}$O$_{16}$S$_4$Na$_4$)$_2$×6 H$_2$O or (C$_{22}$H$_{11}$O$_{16}$S$_4$Na$_4$)$_2$×5 H$_2$O Found: C 3317, H 2.54, Na 11.93 Calculated: C 32.75, H 2.23, Na 11.41; C 33.16, H 2.13, Na 11.56.

B. KY-3 (R$_1$=OH, R$_2$=SO$_2$NH$_2$, R$_3$=H, R$_4$=—CH$_2$—)

KY-1 (2 mM) was treated with 5 ml chlorosulfonic acid and the mixture was stirred at 50° C. for one-half hour. The resultant mixture was added to 20 g of crushed ice to precipitate the crude chloride product, which was collected by filtration and then washed with ether.

The crude chloride product was dissolved in 100 ml of 25% ammonium water solution and allowed to react for 2 hours at room temperature. The mixture was concentrated in vacuo and the remaining oil was dissolved in a small amount of water and filtered. The product was precipitated by adding acetonitrile to the filtrate and collected by filtration and washing with acetonitrile. The compound was characterized as follows: Melting point (M.P.)>300° C.; Mass spec: 1452 (M-7NH$_2$);. HPLC in CH$_3$CN/MeOH/H$_2$O/TFA: 11'46" single peak; (IR/KBr)=3430 (OH), 3187, 1686 (NH$_2$), 1637 (Ar), 1211, 1110, 1044 (SO$_3$) cm$^{-1}$; UV (H$_2$O): 246 nm; H$^1$ NMR(D$_2$O), chemical shifts on the δ scale: 5.15 (CH$_2$), 7.5–8.2 (ArH) ppm; Analysis: (C$_{44}$H$_{40}$O$_{26}$S$_{10}$N$_{12}$Na$_4$)-16H$_2$O Found: C 28.62, H 3.93, N 8.82, S 17.17, Na 5.44; Calculated: C 28.51, H 3.89, N 9.07, S 17.28, Na 4.97;

C. KY-42 (R$_1$=OH, R$_2$=SO$_3$Na, R$_3$=H, R$_4$=>CHCOOH)

Chromotropic acid, disodium (10 mM) in 50 ml water was mixed with glyoxylic acid (10.0 mM, in 5 ml water) and 10 ml of 37% hydrogen chloride at room temperature. The mixture was boiled for 8 hours and the color of the solution turned to dark red. The resultant solution was added to 50 ml of water and filtered. The filtrate was concentrated and ethanol was added to precipitate the product of KY-42. The yield of 87%. The compound was characterized as follows:

Melting point (M.P.)>300° C.; Mass spec: 1623 (M-3H$_2$O). HPLC in CH$_3$CN/MeOH/H$_2$O/TFA: 10'36" single peak; (IR/KBr)=3452 (OH), 1801, 1719 (Co), 1638 (Ar), 1206, 1050 (SO$_3$) cm$^{-1}$; UV (H$_2$O): 238.0, 351.5, 520 nm; H$^1$ NMR(D$_2$O), chemical shifts on the δ scale: 7.10 (CHCO$_2$H) 8.00 (ArH) ppm; C$^{13}$ NMR (D$_2$O), chemical shifts on the δ scale: 116.04, 118.90, 120.94, 121.27, 122.30, 124.30, 124.68, 126.60, 128.37, 136.48, 136.71, 140.50, 143.93, 144.26, 145.75, 152.01, 154.33, 156.01, 156.67; Analysis: (C$_{48}$H$_4$O$_{40}$S$_8$Na$_8$)$_4$-4H$_2$O Found: C 23.74, H 2.50; Calculated: C 32.58, H 2.71;

D. KY-123 (R$_1$=OH, R$_2$=SO$_2$Na, R$_3$=H, R$_4$=>CH$_2$)

KY-1 (2 mM) was treated with 5 ml chlorosulfonic acid and the mixture was stirred at 50° C. for one-half hour. The resultant mixture was added to 50 g of crushed ice to precipitate the product which was collected by filtration and then washed with ether. The crude sulfonyl chloride product was treated with sodium sulfite (20 mM) in 4 ml water. The reaction mixture was kept slightly alkaline by addition at intervals of small portions of 50% NaOH for 2 days. After solvent removal, ethanol was added to precipitate the product, which was acidified by addition of 50% H$_2$SO$_4$, followed by addition of ethanol to precipitate sodium sulfate. The ethanol phase was mixed with ether (1:2, v/v) to precipitate the desired product. Product yield was 39%.

E. KY-147 (R$_1$=OH, R$_2$=SO$_2$NHCH$_3$, R$_3$=H, R$_4$=>CH$_2$)

N-methyl chromotropic acid chloride was formed by reacting chromotropic acid (disodium salt) with thionylchloride in the presence of DMF. The reaction was carried out with stirring at 80° C. for 4 hours. After removal of solvent and excess of thionylchloride in vacuo, ether was added to precipitate the chromotropic acid chloride which was subsequently collected by filtration and washed with ether. The crude product was added to 20 ml of methylamine and stirred for 2 hours. After removal of all solvent from the resultant substance, the residue was dissolved in a 200 ml of cold methanol and filtered. The filtrate was added with acetonitrile to precipitate the product chromotropic acid methyl sulfonamide. Yield 56%.

The chromotropic acid methyl sulfonamide (2 mM) in 3 ml water was reacted with 37% formaldehyde (1 ml) at room temperature for one week. Acetonitrile was added to precipitate the product which was collected by filtration and washed by acetonitrile. Yield was 85%.

F. KY-151 (R$_1$=OCH$_3$, R$_2$=SO$_3$Na, R$_3$=H, R$_4$=>CH$_2$)

KY-1 (50 mM) was dissolved in 80 ml of NaOH water solution (0.2M NaOH) and heated to 50° C., dimethylsulfate (0.2M) was added slowly for 1 hour. The mixture was continuously stirred for another 2 hours and left at room temperature for 2 days. Saturated NaCl solution (100 ml) was added to the resultant substance and filtered. The precipitate was washed with ethanol, acetonitrile and ether sequentially. The dry substance was dissolved in 100 ml of methanol and filtered. The filtrate was concentrated and ether was added to precipitate the methyl ether of KT-1.

G. KY-158 (R$_1$=OH, R$_2$=SO$_2$CH$_3$, R$_3$=H, R$_4$=>CH$_2$)

KY-1 from Example 1A was first treated with thionyl chloride to produce chromotropic acid sulfonyl chloride. This compound was reduced by excess sodium sulfite in the presence of sodium bicarbonate to produce the corresponding sodium sulfonate salt of cyclized chromotropic acid (R$_2$=SO$_2$Na). The sulfonate salt was treated with dimethyl sulfate in the presence of NaHCO$_3$, and worked up as described in Example 1A. Product yield was about 21%.

H. KY-175 (R$_1$=OH, R$_2$=SO$_3$CH$_3$, R$_3$=H, R$_4$=>CH$_2$)

Chromotropic acid was first treated with thionyl chloride to produce chromotropic acid sulfonyl chloride. This compound was then treated with sodium methoxide in methanol in the presence of sodium salt. The product was worked up as described in Example 1A to form the macrocyclic compound. Product yield was about 29%.

I. KY-270 ($R_1$=OCOCH$_3$, $R_2$=SO$_3$Na, $R_3$=H, $R_4$=>CH$_2$)

KY-1 from Example 1A (0.66 mmole) was dissolved in 3 ml water containing 0.1 g NaOH. To this was added 1 g acetyl chloride (13 mmole) and the reaction was allowed to proceed at room temperature overnight with stirring. After solvent removal, 25 ml ethanol was added to precipitate the product. The crude product was dissolved in methanol and filtered. The filtrate was allowed to precipitate, giving a 87% yield.

J. KY-346 ($R_1$=OH, $R_2$=SO$_3$Na, $R_3$=H, $R_4$=—CH$_2$—N(CH$_3$)CH$_2$)

Chromotropic acid disodium salt, was dissolved in 80 ml of water at a concentration of 50 mM with stirring at 50° C. until the solution turned to clear, hexamethylene-tetramine (50 mM) was then added to above solution with continuous stirring at the same temperature for additional two hours. At this time, the color of this mixture converted to dark blue. The mixture was allowed to stir at room temperature for 2 days. The resultant dark blue solution was filtered and the filtrate was concentrated, evaporated by flask, which was subsequently treated with 200 ml methanol to precipitate the product KY-346. The yield of KY-346 was 85%. The compound was characterized as follows:

M.P.>300° C.; HPLC in CH$_3$CN/MeOH/H$_2$O/TFA: 13'07" single peak; (IR/KBr)=3425 (OH), 1626 (Ar), 1197, 1052 (SO$_3$) cm$^{-1}$; UV (H$_2$O): 232.0, 377.5 nm Analysis: (C$_{13}$H$_{11}$O$_8$NS$_2$Na$_2$)$_4$×12 H$_2$O Found: C 33.17, H 3.13, N 2.75 Calculated: C 33.98, H 3.59, N 2.96. Molecular weight: 1668 by gel filtration.

EXAMPLE 2

Preparation of Phenyl Macrocyclic Compounds

A. Y-49 ($R_1$=OH, $R_2$=SO$_3$H, $R_4$=—CH$_2$—, n=4)

4-tert-butylcalix(4)arene (10 g) was treated with 200 ml of concentrated H$_2$SO$_4$ at room temperature for 0.5 hour and then at 75°-85° C. oil bath for another 4 hours. The reaction was completed when no water-insoluble material was detected. The resultant oil was dropped into 500 g of crushed ice and the solution was filtered by reduced pressure. After the water removed away from the filtrate, acetonitrile (500 ml) was added to the residual and allowed to stand for 4 hours to precipitate the crude product which was then collected by filtration and washed with acetonitrile, ethyl acetate and ether. Yield 8 g (73%). The pure product was furnished by recrystallization of the crude compound with methanol-ether or methanol-acetonitrile system. The single crystal compound was also found in the recrystallization process.

Similar methods were used in the synthesis of Y-77 ($R_1$=OH, $R_3$=SO$_3$H, $R_4$=—CH$_2$—, n=6) and Y-1 ($R_1$=OH, $R_3$=SO$_3$H, $R_4$=—CH$_2$—, n=8).

B. KY-225 ($R_1$=—OH, =O), $R_2$=SO$_3$H, $R_4$=>CH$_2$, ≧CH, n=4)

4-tert-Butylcalix(4)arene (1 g) was treated with 10 ml of 95-98% sulfuric acid at room temperature for 0.5 hours then at 160° C. for 5 minutes. After the resultant mixture was cool, the mixture was poured slowly into 100 ml of crushed ice and filtrated. The solution was evaporated and the residual was added with 300 ml acetonitrile to produce great amount of precipitate which was collected by filtration and washed with acetonitrile. The crude product was dissolved in 20 ml methanol and the product was precipitated by addition of diethyl ether. Yield was 84%.

Similar methods were used in the synthesis of Y-48 ($R_1$=—OH or =O, $R_3$=SO$_2$H, $R_4$=—CH$_2$—, n=6) and Y-226 ($R_1$=—OH or =O, $R_2$=SO$_3$H, $R_4$=—CH$_2$—, n=8).

C. O-Acetylate of Y-1 ($R_1$=—OCOCH$_3$, $R_2$=SO$_3$Na, $R_4$=>CH$_2$, n=8)

Under nitrogen, Y-1 (0.4 g) was refluxed in a stirring mixture of NaOAc (305 mg) and acetic anhydride (20 ml) for 3 days. After cooling to room temperature, the suspension was filtered. The solid was washed three times with ether (25 ml) and dried in vacuo. The resulting solid was sonicated in a mixture of MeOH (50 ml) and activated charcoal (150 mg), filtered, and the black precipitate was washed twice with MeOH (10 ml). The filtrate was concentrated in vacuo. The resulting residue was recrystallized from MeOH/acetonitrile mixture. The product (240 mg) was obtained after filtration and lyophilization. $^{13}$CNMR (D$_2$O, δ): 173.9, 151.6, 144.1, 135.6, 130.1, 34.2, and 22.4.

D. Y-78 ($R_1$=—OH, $R_2$=SO$_2$NH$_2$, $R_4$=>CH$_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the crude product is dissolved in 100 ml of 25% ammonium water solution and allowed to react for 2 hours at room temperature. The mixture is concentrated in vacuo and the remaining oil is dissolved in a small amount of water and filtered. The product is precipitated by adding acetonitrile to the filtrate and collected by filtration and washing with acetonitrile.

E. Glycyl sulfonamide of Y-1 ($R_1$=—OH, $R_2$=SO$_2$NHCH$_2$CO$_2$H, $R_4$=>CH$_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the material is added to 50 ml of solution containing 5.7 g glycine and 2.1 g NaOH, and stirred for 2 hours at room temperature. After removal of all solvent from the resultant substances, the residue is dissolved in a 200 ml of cold methanol and filtered. The filtrate is added with acetonitrile to precipitate the product.

F. Acetyl-Bridged Y-49 ($R_1$=—OH, $R_2$=SO$_3$H, $R_4$=—CHCO$_2$H—, n=4)

4.3 g of p-hydroxybenzenesulfonic acid was treated with g gram of glyoxylic acid in 30 ml 18% conc. HCl for 2 hours at 100° C. After the reaction product was dried under reduced pressure, 50 ml of methanol was added and insoluble impurities were removed by filtration. The product was precipitated from the filtrate by addition of ether then collected by filtration and dried in vacuo.

G. Toluene Sulfonyl Ester of Y-49 ($R_1$=—SO$_3$C$_6$H$_4$CH$_3$, $R_2$=SO$_3$H, $R_4$=>CHCO$_2$H, n=4)

Under nitrogen is added toluenesulfonyl chloride (1.9 g) to a suspension of dry sodium carbonate (1.06 g), dry dimethylformamide (10 ml) and Y-49 (0.75 g). After an overnight reflux, the resulting mixture is cooled to room temperature and filtered. The filtrate is diluted with ether to precipitate out the crude product. Recrystallization from acetonitrile/ether solvent provided the product.

H. Carboxylic Acid Derivative of Y-49 ($R_1$=—CO$_2$H, $R_2$=SO$_3$H, $R_4$=>CHCO$_2$H, n=4).

Under nitrogen, trifluoromethanesulfonic anhydride (1.0 ml) is added to ice cold dry dichloromethane solution (10 ml) of 2,6, di-tert-butyl-4-methylpyridine (1.25 g) and 4-tert-butylcalix[4]arene (0.65 g). After overnight stirring at room temperature, the mixture is diluted with pentane (10 ml) and filtered. The filtrate is extracted with ice cold 1N aqueous NaOH solution, ice cold 1N aqueous HCl solution, then saturated aqueous NaCl solution, dried over anhydrous sodium sulfate, filtered through a pad of silica gel and concentrated in vacuo. The residue is dissolved in a mixture of dry diisapropylethylamine (10 ml), trimethylsilyl cyanide (0.5 ml) and palladium tetrakis-triphenyl phosphine (20 mg). After an overnight reflux under nitrogen and then cooling to room temperature, ether (50 ml) was added and the resulting suspension was filtered. After concentration of the filtrate in vacuo and silica gel chromotography (hexane/ethyl acetate eluent), the cyano intermediate is heated at 80° C. with concentrated sulfuric acid (10 ml) for 3 hours, diluted with water (10 ml) and refluxed overnight. After cooling to room temperature, the resulting mix is added to charcoal (0.5 g) and ice (50 g). After filtration, the resulting filtrate is concentrated in vacuo to ca 15 ml in volume and the resulting solid was filtered. The solid is dissolved in a minimal amount of methanol and precipitated out by adding ether. Final purification by reverse phase C18 chromatography (methanol/water eluent) provide the product.

I. Methyl Ether of Y-1 ($R_1$=OMe, $R_3$=SO$_3$Na, $R_4$=>CH$_2$, n=8).

iodomethane (0.58 ml) was added to a heated (50° C.) mixture of Y-1 (447 mg), NaOH (6N in water, 1.53 ml), and dimethylsulfoxide (9 ml) for 20 hours. The resulting mix was added dropwise into stirring absolute ethanol (100 ml). The resulting suspension was centrifuged (9,000 rpm, 20 minutes), and then the supernatant was removed. Twice, the resulting solid was dissolved in water (6 ml), and the resulting solution was treated as above with ethanol, centrifuged, and the supernatant removed. The remaining solid was lyophilized to yield the product (420 mg).

$^{13}$CNMR (D$_2$O, δ): 161.2, 140.9, 137.6, 129.5, 63.6, and 33.5.

J. XXVI. ($R_1$=—OH, $R_2$=H, $R_3$=$R_5$=H, $R_4$=—CH$_2$—, n=4)

Calix(4)arene XXVI is prepared from 4-tert-butyl-calix(4)arene (XXV; FIG. 13) as described (Gutsche, Levine, and Sujeeth, 1985). A hot solution of 5.0 g (6.75 mmol) of XXV in 250 ml of toluene is placed in a 500 ml three-necked round-bottom flask fitted with a mechanical stirrer and a gas inlet tube. The solution is cooled to 50°–55° C., treated with 5.0 g (37 mmol) of anhydrous AlCl$_3$, and stirred for 2 h at 50°–55° C. in an inert atmosphere. The mixture is cooled in an ice bath and stirred with 125 ml of 1N HCl for 30 min, the organic phase is separated and washed, dried, and evaporated to leave a yellow residue. This is triturated with 500 ml of ether, and the insoluble material is recrystallized from CHCl$_3$—CH$_3$OH to yield 1.9 g (66%) of XXVI as off-white microcrystals. m.p. 313°–318° C.

K. XXVIII. ($R_1$=—OH, $R_2$=COOH, $R_3$=$R_5$=H, $R_4$=—CH$_2$—, n=4)

Calix(4)arene XXVIII is prepared as described (Yilmaz and Vural). Known p-acetyl-calix(4)arene (XXVII; 1.3 g) (Yilmaz and Vural, 1991; No et al., 1986) is dissolved in 50 ml of 2N aqueous NaOH. A solution of iodine (8 g) and potassium iodide (20 g) in 40 ml of water is added and the mixture stirred. The solution is warmed on a water bath for 1 h. Iodoform is removed by filtration,and NaHSO$_3$ (20 g) is added to the filtrate. Concentrated HCl is then added to the filtrate to produce a pale yellow precipitate which is then filtered off, washed with water, and dried. The crude product is dissolved in 10 % aq. NaHSO$_3$ and treated with charcoal. After filtration, the solution is acidified with 1N HCl. The precipitated product is collected by filtration, washed with distilled water until free of Cl$^-$, and dried in a vacuum desiccator, yielding 1.04 g (79%) of XXVIII. m.p. 320° C. (dec.).

L. XXXI. ($R_1$=—OH, $R_2$=—CH$_2$COOH, $R_3$=$R_5$=H, $R_4$—CH$_2$—, n=4)

Calix(4)arene derivative XXXI is prepared via p-(dimethylamino)methyl-calix(4)arene (XXIX) as described (Gutsche and Nam, 1989).

To a solution of 15.9 g (39.5 mmol) of calix(4)arene (XXVI) in 360 ml of THF are added 45 ml of acetic acid, 22.5 g (0.2 mol) of 40% aqueous dimethylamine, and 16.2 g (0.2 mol) of 37% aqueous formaldehyde. The reaction mixture is stirred for 24 h at room temperature, the solvents are removed under vacuum, and the residue is dissolved in 250 ml of water. The aqueous solution is extracted twice with 200 ml of ether and neutralized with 10% K$_2$CO$_3$ solution, and the precipitate that forms is removed by suction filtration. The product is dried under vacuum and then recrystallized from chloroform to give 19.1 g (78%) of p-(dimethylamino)methyl-calix(4)arene XXIX as white needles.

To a solution containing 16.3 g of p-(dimethylamino)-methyl-calix(4)arene in 220 ml of DMSO is slowly added 9.57 ml (0.15 mol) of methyl iodide. After the reaction mixture is stirred for 30 min at room temperature, 15 g (0.3 mol) of NaCN is added, and the mixture is heated for 2 h at 80° C. under a nitrogen atmosphere. The solution is then cooled, treated with 1 liter of ice water, acidified with 2N HCl, filtered, and air-dried. The crude product is recrystallized from CH$_3$CN to yield 12.8 g (88%) of p-cyanomethyl-calix(4)arene XXX as a pale yellow solid.

p-Cyanomethyl-calix(4)arene (0.5 mmol) is then added to a solution of DMSO (25 ml) and conc. aqueous HCl (5 ml) and refluxed overnight. After dilution with water (100 ml) at room temperature, the precipitate is collected by filtration and recrystallized from methanol to provide purified XXXI.

M. XXXIII. ($R_1$=—OH, $R_2$=—CH$_2$CH$_2$COOH, $R_3$=$R_5$=H, $R_4$=—CH$_2$—, n=4)

Calix(4)arene derivative XXXIII is prepared as described (Gutsche and Nam, 1989).

To a solution of 3.26 g (5 mmol) of (dimethylamino)-methyl-calix(4)arene (XXIX; Example C) in 80 ml of DMSO, 1.90 ml (30 mmol) of methyl iodide is added. After the mixture is stirred for 30 min, sodium diethyl malonate, prepared from 1.20 g of Na, 7.28 g of diethyl malonate, and 28 ml of EtOH, is added, and the reaction mixture is heated for 2 h at 80° C. in an atmosphere of nitrogen. The solution is then cooled, poured onto 200 ml of ice-water, acidified with 2N HCl, and worked up in the usual fashion to give 5.50 g (99%) of p-(diethyl-malonyl)methyl-calix(4)arene XXXII as crude product. Hydrolysis and decarboxylation is effected by dissolving the crude product in 100 ml of DMSO and 30 ml of conc. HCl and heating at 120° C. for 10 h in an atmosphere of nitrogen. The mixture is then cooled, poured into 500 ml of ice-water, stirred for 10 min, and filtered. The precipitate is recrystallized from acetoneethyl acetate to give 2.42 g (69%) of XXXIII as colorless crystals. m.p. 224.

N. XXXVI ($R_1$=—OH, $R_2$=—$PO_3H$, $R_3$=$R_5$=H, $R_4$=—$CH_2$—, n=4)

Derivative XXXVI is prepared by adaptation of the methods of Arduini et al. and Hirao et al.

Calix(4)arene (XXVI) is refluxed with Hg(O-COCF$_3$)$_2$ in CHCl$_3$, giving an almost quantitative yield of tetra-(Hg-OCOCF$_3$) calixarene derivative. Following evaporation of the CHCl$_3$, metal iodine exchange is carried out by reaction of the calixarene derivative with I$_2$ in CHCl$_3$, giving p-iodo-calix(4)arene XXXIV as a brown compound in 40% yield.

A concentrated toluene solution of HPO(OEt)$_2$ (10 mmol), triethylamine (10 mmol), Pd(PPh$_3$)$_4$ (0.3 mmol) and p-iodocalix(4)arene (1.0 mmol) is stirred at 100° C. under nitrogen atmosphere for 3 days. After dilution with ether (50 ml) at room temperature, the reaction mixture is filtered and then concentrated under high vacuum (100° C., at <0.1 mm Hg). The resultant concentrate is purified by silica chromatography to obtain purified phosphonate diester (XXXV), which is then refluxed overnight in 6N HCl (5 ml) to produce the phosphonic acid product. After removal of solvent (100° C., at <0.1 mm Hg), the solid is recrystallized from methanol to yield purified XXXVI.

O. XXXIX. ($R_1$=—OH, $R_2$=—$CH_2PO_3H$, $R_3$=$R_5$=H, $R_4$=—$CH_2$—, n=4)

Calix(4)arene derivative XLIV is prepared via p-chloromethyl-calix(4)arene as described (Almi et al.).

To a solution of 1.0 g (2.4 mmol) of calix(4)arene (XXVI) and 14.4 g (81 mmol) of chloromethyl-n-octyl ether in 100 ml of CHCl$_3$ cooled at −10° C., is added 4.7 ml (40.3 mmol) of SnCl$_4$ dropwise over about 15 min. The cooling bath is then removed, and the reaction mixture is kept at room temperature until all of the calixarene starting material has reacted (after ~50 min), as judged by thin layer chromatography (hexane:ethyl acetate=4:3). Water is then added slowly and the two phases are allowed to separate. The organic layer is washed twice with distilled water and is then dried over Na$_2$SO$_4$. Following removal of the Na$_2$SO$_4$, the solvent is evaporated to give a residue that is then washed with n-hexane and filtered, giving 1.23 g (80%) of product, p-chloromethyl-calix(4)arene XXXVII.

Derivative XXXVII (1 g, 1.6 mmol) is refluxed for 6 h in 20 ml of triethyl phosphite. Excess triethyl phosphite is then removed by distillation, and the resultant solid residue (phosphate diester XXXVIII) is dried under vacuum for 8 h. A solution of 20% HCl (60 ml) is added and the resultant reaction mixture is refluxed for 20 h. The solvent is then removed by evaporation, and the resultant precipitate is filtered, washed first with methanol and then with CHCl$_3$, and dried under vacuum to give 1.11 g (80%) of XXXIX as a white solid. m.p. 360° C.

P. XLIV. ($R_1$=—OTs, $R_2$=—$CH_2CH_2Br$, $R_3$=$R_5$=H, $R_4$=—$CH_2$—, n=4)

p-2-Bromoethyl-calix(4)arene derivative XLIV is prepared as described (Gutsche, Levine, and Sujeeth, 1985; Gutsche, Dhawan, et al., 1983).

(a) To a solution of calix(4)arene (XXVI; 2.14 g) in 100 ml of THF and 10 ml of DMF is added 2.0 g of NaH followed by 28 g of allyl bromide. The mixture is refluxed 1 h, after which the THF is removed by evaporation, and the residue is partitioned between water and CHCl$_3$. The CHCl$_3$ extract is washed with water, dried, and evaporated, and the residue is recrystallized from 95% ethanol to give 2.18 g (74%) of O-allyl-calix(4)arene XL as colorless needles.

(b) A solution of 1.66 g (2.84 mmol) of the O-allyl calix(4)arene in 25 ml of N,N-diethylaniline is heated at reflux for 2 h in an inert atmosphere. The solution is cooled, poured into 250 ml of ice-water, stirred with 250 ml of concentrated HCl, and filtered to yield a crude product, which is then crystallized from isopropanol to afford 1.22 g (74%) of p-allyl-calix(4)arene XLI as off-white needles, m.p. 245°–248° C.

(c) A solution of 2.09 g (3.57 mmol) of p-allyl-calix(4)arene in 100 ml of dry THF is treated with 1.0 g (42 mmol) of NaH followed by 4.0 g (21 mmol) of p-toluenesulfonyl chloride, and the mixture is heated at reflux for 1.5 h. The solvent is removed by evaporation to leave a light brown oil, which is dissolved in 100 mL of CHCl$_3$, cooled in an ice bath, and treated with 100 ml of ice-water. The organic phase is dried and evaporated, and the residue is recrystallized from isopropanol to yield 3.41 g (79.5%) of tosylated p-allyl-calix(4)arene (XLII).

(d) A solution of 3.50 g of tosylated p-allyl-calix(4)arene in 60 ml of CH$_2$Cl$_2$ and 40 mL of CH$_3$OH is cooled in a dry ice-acetone bath and treated with ozone until it retains a blue color (10–15 min). Nitrogen is bubbled through the solution until the blue color disappears, and 2 g of NaBH$_4$ is added. The solution is stirred at room temperature for 3–4 h, poured into ice cold, dilute HCl solution, and worked up in conventional fashion to yield a crude product as a white resin. Recrystallization from 3:5 acetone-hexane produces 1.51 g (43%) of microcrystalline p-2-hydroxyethyl-calix(4)arene phenol-oxygen-tosylate (XLIII).

(e) A solution of triphenylphosphine dibromide, prepared from 6.5 g (25 mmol) of triphenylphosphine and Br$_2$ (Schaefer et al., 1973), in 150 ml of dry acetonitrile is treated with a solution of the product from step (d), prepared from 3.25 g of the product of step (c), in 50 ml of acetonitrile. The mixture is stirred for 2 h at room temperature and filtered, and the solvent is removed by evaporation to leave a sticky orange oil. This is stirred with 250 ml of 95% ethanol for 8 h, and 3.10 g (78%) of p-2-bromoethyl-O-tosyl-calix(4)arene XLIV is collected as a white powder by filtration.

Q. XLVI ($R_1$=—OH, $R_2$=—$CH_2CH_2PO_3H$, $R_3$=$R_5$=H, $R_4$=—$CH_2$—, n=4)

Calix(4)arene derivative XLVI is prepared from p-2-bromoethyl derivative XLIV (Example G) by modification of the method used to make XXXIX from p-chloromethyl-calix(4)arene (Example F).

Purified bromide XLIV (1 mmol) is refluxed in P(OEt)$_3$ (10 ml) overnight under nitrogen atmosphere. After removal of excess phosphite at high vacuum (100° C., 0.1 mm Hg), the residue (diethyl phosphite XLV) is added to a mixture of DMSO (5 mL) and 6N NaOH (1 ml) under nitrogen and heated at 100° C. overnight, thus removing the tosylate groups. After removal of DMSO under high vacuum (100° C., <0.1 mm Hg), the residue is diluted with hot water (25 ml) and acidified with conc. HCl to give upon cooling a precipitate which is then collected by filtration. Recrystallization of the solid from methanol provides purified XLVI.

R. XLVII. ($R_1$=—OH, $R_2$=—CH$_2$SO$_3$H, $R_3$=$R_5$=H, $R_4$=—CH$_2$—, n=4)

To a solution of p-chloromethyl-calix(4)arene (XXVII, Example F; 2.5 mmol) in 95% ethanol (10 ml) is added at room temperature an aqueous solution of Na$_2$SO$_3$ (2M, 11 mmol). After refluxing overnight, the solvent is removed by distillation until a precipitate forms. The precipitate is collected by filtration, washed with cold, saturated aqueous NaCl, and then suspended in a minimum of water and passed through a column of Amberlite IR-120 resin in water. The UV-active fractions containing product are concentrated under vacuum and the residue is recrystallized from methanol to give purified XLVII.

S. XLIX. ($R_1$=—OH, $R_2$=—CH$_2$CH$_2$SO$_3$H, $R_3$=$R_5$=H, $R_4$=—CH$_2$', n=4)

Calix(4)arene derivative XLIX is prepared from bromoethyl derivative XLIV (Example G) by applying sequentially the sulfonation method of Example I to give XLVIII, the hydrolysis step of Example H to remove the tosyl group, and the Amberlite IR-120 step of Example I to produce sulfonic acid XLIX.

T. LII. ($R_1$=—OAc, $R_2$=t-butyl, $R_3$=$R_5$=H, $R_4$=—CH(OH)—, n=4)

Calixarene LII is made via known calixarene LI (Gormer et al; 1990: $R_1$=—OAc, $R_2$=t-butyl, $R_3$=$R_5$=H, $R_4$=—C(=O)—, n=4) as follows.

A solution of 1.5 g (2.3 mmol) of p-tert-butyl-calix-(4)arene (XXV) is refluxed in a solution of acetic anhydride (37 ml) and conc. sulfuric acid (0.1 ml). The reaction mixture is then added to 300 ml of ice water, producing an oil that slowly crystallizes. The crystalline solid is collected, washed several times with water, and dried with petroleum ether, giving the O-acetyl-p-tert-butyl-calix(4)arene (L) as white crystals.

To a three-necked round-bottom flask equipped with a condenser, stirrer, and addition funnel, are added 1.2 g (1.5 mmol) of O-acetyl-p-tert-butyl-calix(4)arene in 70 ml of acetic anhydride. To this is added dropwise a solution of 3.5 g chromium(IV)oxide in a mixture of acetic anhydride (15 ml) and acetic acid (5 ml) at 20° C. with stirring, and the reaction mixture is added to 600 ml of ice-water and allowed to stand for 12 h. The resultant yellow precipitate is collected and washed with water. Recrystallization from methanol yields the purified keto derivative LI (O-acetyl-p-tert-butyl-calix-(4)arene, $R_4$=—C(=O)—) (Gormer et al., 1990). m.p. 305° C.

To the keto derivative (1 mmol) from the previous step, dissolved in absolute ethanol (10 mL), is added NaBH$_4$ (8 mmol) in small portions at room temperature under nitrogen atmosphere. After reduction of the keto-group is complete, as judged from the disappearance of the carbonyl band at 1670 cm$^{-1}$ observed by infrared spectroscopy, acetic acid (1 ml) is added dropwise and the resulting mixture is stirred for 1 h. The solvent is removed under high vacuum (<0.1 mm Hg), and the resultant solid is refluxed in methanol (5 ml) for 20 min. After removal of solvent, the residue is purified by silica chromatography, yielding purified hydroxymethylene-bridged, O-acetyl-p-tert-butyl product LII.

U. LIII. ($R_1$=—OH, $R_2$=$R_3$=$R_5$=H, $R_4$=—CH(Cl)—, n=4)

Derivative LII (Example K; 0.5 mmol) is refluxed in SOCl$_2$ (5 ml) under nitrogen atmosphere. After evolution of SO$_2$ has ceased, excess SOCl$_2$ is removed by distillation under high vacuum (<0.1 mm Hg). To the residue is added THF (5 ml), and distillation is repeated to remove residual SOCl$_2$, yielding chloro-derivative LIII.

V. LVI. ($R_1$=—OH, $R_2$=$R_3$=$R_5$=H, $R_4$=—CH(CO$_2$H)—, n=4)

(a) A reaction mixture containing chloro-derivative LIII (1 mmol) and NaCN (1.1 mmol) in DMSO (10 ml) is heated at 80° C. under nitrogen for 6 h. The mixture is then poured in ice-water (50 ml), acidified with 3N HCl, and the resultant precipitate is collected by filtration. The filtrate is added to a mixture of DMSO (25 ml) and conc. aqueous HCl (5 ml) and refluxed overnight. After dilution with water (100 ml) at room temperature, the resultant precipitate is collected by filtration and recrystallized from CHCl$_3$/methanol to afford LV.

(b) To remove the p-tert-butyl groups, the product from the previous step is added in small portions under nitrogen atmosphere to about (60° C.) toluene suspension (50 ml) of AlCl$_3$ (10 mmol). After stirring overnight, the mixture is cooled to 0° C., and 1N HCl (100 ml) is added dropwise. After the addition, the organic phase is separated and concentrated in vacuo. Recrystallization from CHCl$_3$/methanol affords purified LVI.

W. LVII. ($R_1$=—OAc, $R_2$=t-butyl, $R_3$=$R_5$=H, $R_4$=—CH(CH$_2$CH=CH$_2$—, n=4)

Chloro-derivative LIII (Example L) is dissolved in a minimum amount of THF, and the mixture is added dropwise to a stirred, cold (−78° C.) solution of THF containing (CH$_2$CH=CH$_2$)$_2$CuLi (0.2M, 3 mmole). The suspension is then allowed to warm to room temperature. After overnight stirring, the suspension is extracted with a 3:1 mixture (5 ml) of saturated NH$_4$Cl and saturated NH$_3$ solutions. The organic phase is dried over anhydrous Na$_2$SO$_4$, filtered, and concentrated in vacuo. The residue is purified by silica chromatography to provide the O-acetyl-p-tert-butyl allyl derivative LVII.

If desired, removal of the acetyl and t-butyl groups is achieved as in part b of the following Example.

X. LVIII. ($R_1$=—OH, $R_2$=$R_3$=$R_5$=H, $R_4$=—CH(CH$_2$CO$_2$H)—, n=4)

(a) Calixarene LVII (1 mmol) in CH$_2$Cl$_2$ (10 ml) is ozonized at −78° C. until the reaction mixture turns blue. Formic acid (2 ml) and then hydrogen peroxide (1 ml) are added, and the resultant mixture is allowed to warm to room temperature while being purged with nitrogen. The mixture is then refluxed overnight, after which the solvent is removed under vacuum, yielding LVIIa.

(b) Removal of the acetyl groups is achieved by refluxing the O-acetylated product (0.2 mmol) from the previous step in a mixture of methanol (4 ml) and 6N NaOH (1 ml) overnight. After removal of solvent under vacuum, the residue is diluted with water (10 ml), acidified to pH 2. The resultant precipitate is collected by filtration and recrystallized from CHCl$_3$/hexane provides. De-t-butylation is then effected according to step b of Example M, yielding purified LVIII.

Y. LXII. ($R_1$=—O(CH$_2$)$_3$SO$_3$Na, $R_2$=H, lower alkyl, $R_3$=$R_5$=H, $R_4$=—CH$_2$—, n=4)

Calix(4)arene LXII is prepared as described (Shinkai et al., 1989).

Calix(4)arene XXVI (1.54 mmol) is dissolved in THF (100 ml) at 50° C. under nitrogen atmosphere. After cooling, sodium hydride (1.20 g, 30 mmol; 60% dispersion in oil) is added and the mixture is stirred until evolution of hydrogen ceases (~1 h). Propane-1,3-sulfone (2.26 g, 18.5 mmol) is then added dropwise and the mixture is stirred at room temperature for 24 h. Remaining NaH is decomposed by addition of methanol, after which the solvent is evaporated under reduced pressure, and the residue is dissolved in hot water (500 ml). Any insoluble material is removed by centrifugation. The product is then precipitated by the salting-out method with sodium acetate to give purified LXII (10% yield). m.p.>300° C.

Z. LXIV. ($R_1$=—O($CH_2$)$_3$$SO_3$Na, $R_2$=$SO_3$Na, $R_3$=$R_5$=H, $R_4$=—$CH_2$—, n=4)

To a mixture of DMSO (10 ml), p-sulfonyl-calix(4)arene (XV, Example 8; 1 mmol), and 6N NaOH (1 ml) is added propane-1,3-sulfone (9 mmol), and the resultant reaction mixture is heated at 60° C. overnight. After removal of solvents under vacuum (<0.1 mm Hg), the solid residue is diluted with a minimum amount of water and then added dropwise to 100 ml of ethanol with stirring. The resultant precipitate is collected by filtration, and the steps of dilution in a minimum of water and dropwise addition to 100 ml of ethanol are repeated once. The precipitate is collected by filtration and recrystallized from methanol/$CH_3CN$ provides purified LXIV.

EXAMPLE 3

Preparation of Aryl-Bridged Macrocylic Compound

A. VII. Mixed naphthyl/Phenyl Macrocycle

Chromotropic acid, disodium (10 g) in 55 ml of water was treated with 22 ml of 30 ml 37% HCl. To this solution, 1,2-benzenedimethanol (5 g) in 55 ml of acetic acid was added and this reaction was carried out at reflux for 6 hours. After filtration of the resultant mixture, acetonitrile (500 ml) was added to precipitate the crude product and collected it by filtration. The crude compound was further purified by column chromatographic purification on LH-20 resin and elution with ethanol.

B. LXXV. Napthyl-Phenyl Macrocycle (n=2 napthyl+2 phenyl)

Mixed macrocycle LXXV is prepared using the strategy outlined by de Mendoza et al.

Chromotropic acid (III, FIG. 3A; 10 mmol) and 2,5-dihydroxymethyl-3-tert-butyl-phenol (LXXII; 1 mmol) is heated at 100° C. overnight in the presence of conc. HCl (5 ml). After removal of solvent under high vacuum (100° C.<0.1 mm Hg), the residue is dissolved in a minimum amount of water and eluted through a column of Sephadex LH-20 in water. The isolated product (LXXIII; 0.6 mmol), which contains two chromotropic acid units and one phenol unit, is again heated at 100° C. overnight in the presence of conc. HCl (2 ml) and 2,5-dihydroxymethyl-3-tert-butyl-phenol (LXXII; 0.6 mmol). The product (LXXIV; 0.05 mmol), isolated using a Sephadex LH-20 column, is dried under vacuum and then heated at 80° C. for 6 h in conc. sulfuric acid (1 ml) under nitrogen atmosphere. After dilution with cold water (5 ml) and treatment with charcoal (100 mg), the resulting mixture is filtered, and most of the water in the filtrate is removed in vacuo (<0.1 mm Hg). The residue is dissolved in hot, saturated aqueous NaCl. Upon cooling to 0° C., a precipitate forms. The precipitate is filtered, dissolved in a minimum of water, and eluted through a column of Amberlite IR-120 in water. The fractions containing pure product are combined and lyophilized, yielding purified LXXV (0.03 mmol).

EXAMPLE 4

In vitro Anticoagulant Activity Assays

A. Preparation of Blood samples

Venous blood samples were taken using clean venipuncture procedures. Samples were collected in collection tubes (VACUTAINER TM) or in plastic tubes containing sodium citrate such that 9 parts of blood were added to 1 part of 3.8% sodium citrate, and placed in an icebath. Prior to centrifugation, blood samples were checked for the presence of clots, and any tubes containing clots were discarded. Samples were centrifuged at 1500×g for 15 minutes in a refrigerated clinical centrifuge. Plasma was removed from the sample using a non-wettable plastic pipet and stored in a non-wettable plastic stoppered tube, at 4° C. Plasma samples showing evidence of hemolysis were discarded. Plasma samples were then placed in an icebath for testing within 8 hours of collection, or were alternatively frozen at $-20_0$ for testing within 1 week of collection. All in vitro specimens after drug administration were collected into VACUTAINER ® coagulation tubes for assays of PT, APTT and fibrinogen within 8 hours without freezing.

Human blood was collected by venipuncture using a double-syringe technique through a 21 gauge butterfly needle. The initial 2-3 ml's of blood were discarded and the subsequent blood was immediately added to 3.8% citrate (1:10) in plastic tubes. The tubes were centrifuged for 20 minutes at 2,500 RPM to obtain platelet poor plasma. Additional human plasma was obtained from a blood bank at a university medical center. Plasma was obtained from blood from health donors into CPD-A1 anticoagulant. The blood was centrifuged and the resulting plasma was freshly frozen in 250 ml packs. Prior to use, the individual plasma packs were thawed in a water bath at 37° C. and pooled. A minimum of at least 5 individual plasmas were used to prepare a pool. Aliquots of all plasmas were stored at −70° C. prior to use.

Factor I deficient plasma (made deficient by plasma pheresis of normal donors) was obtained from George King Biomedical (Overland Park, Kans.) This plasma is stored at −70° C. until use. Plasma deficient in antithrombin III is prepared using heparin affinity chromatography (Ofosu, et al., 1981). Heparin-sepharose CL 6B is obtained from Pharmacia (Piscataway, N.J.). A column (total volume 156 ml) will be packed with heparin-sepharose and equilibrated with 0.06M $NaHPO_4$ and 0.5M NaCl pH 7.5. To obtain the antithrombin III deficient plasma, 200 ml of citrated normal human, platelet poor plasma is applied to the column. The plasma is eluted at a flow rate of 2.5 ml/minute with equilibration buffer. The eluted plasma is dialyzed against 0.4% sodium citrate containing 0.15M NaCl, aliquoted and frozen at −70° C. prior to use. Antithrombin III levels are determined using a fractional (ACA; automated chemistry analyzer, E. I. Du Pont Co.) method.

Platelet rich plasma was prepared in the following manner. Blood was drawn from individual donors into 3.8% citrate (1:10 ratio) and centrifuged at a slow speed to obtain plasma rich in platelets. The platelet count was adjusted (using autologous platelet poor plasma) to about 250,000 platelets/$mm^3$ using a light microscope and a Bright line hemocytometer.

B. Prothrombin Time Assay (PT)

Plasma samples collected as described in Example 4A, were pre-warmed to 37° in a waterbath, then 0.1 ml aliquots above were forcibly added to tubes containing 0.2 ml thromboplastin-calcium reagent (Dade ® Thromboplastin•C, Becton Dickinson), reconstituted and stored according to manufacturers directions, prewarmed and resting in a 37° waterbath. Each tube was timed individually while being mixed gently, using the manual tilt tube method. Time until visible clot formation was obtained for each sample. All samples were assayed in triplicate, and the clotting times (PT times) were averaged. Alternatively, clotting time was measured in a fibrometer (BBL, Cockeysville, Md.).

C. Activated Partial Thromboplastin Time (APTT)

Plasma samples were collected as described in Example 4A and stored in an icebath until testing. 0.1 ml of plasma sample was mixed with 0.1 ml of partial thromboplastin (Actin ® Activated Cephaloplastin Reagent; Becton Dickinson), reconstituted and handled according to manufacturer's instructions, in a 13×100 mm polyethylene tube. The tube containing the mixture was placed in a 37° water bath for 3 minutes, prior to addition of 0.1 ml of pre-warmed (37°) 0.02M calcium chloride). The tube was then tilted gently at 5 second intervals, for a total of 20 seconds at 37°, then removed from the water bath and the periodic tilting continued as the sample was observed for fibrin web formation. Alternatively, clot formation was measured in a fibrometer (BBL, Cockeysville, Md.). All samples were assayed in duplicate.

D. Plasma Recalcification Time (Plasma Clotting Time)

Blood was collected in 8% sodium citrate and centrifuged for at least 20 minutes at 1500×g to obtain platelet-poor plasma. A 50 microliter aliquot of plasma was mixed with 50 microliters of physiological saline solution, and the mixture was placed in a test tube at room-temperature. Twenty-five microliters of pre-warmed (37°) 1% (1 g/100 ml) calcium chloride was added to the test tube with gentle mixing. The mixture was then tilted at 1 minute intervals and observed for clot formation.

E. Fibrinogen Assay

Blood was collected as described in Example 1A. Clotting time was determined after addition of thrombin reagent (Data-Fi ® Thrombin Reagent, Baxter Healthcare Corp., Miami, Fla.; reconstituted according to manufacturer's instructions) a dilute plasma sample. This time was compared to a standard curve of clotting times for samples containing known amounts of fibrinogen, to determine fibrinogen concentration of the dilute sample.

F. Reptilase Assay (Atroxin Time)

Blood samples were centrifuged to produce platelet poor plasma (1500×g, 15 min.), as described in Example 4A. Plasma samples (0.2 ml) were incubated at 37° for 5 minutes. ATROXIN ® (Sigma Chemical Co., St. Louis, Mo.), prewarmed to 37°, was added as a 0.1 ml aliquot to each sample tube with mixing to initiate the reaction. Time to clotting was recorded as Atroxin time.

G. Thrombin Time Assay (TT)

Thrombin solution was prepared by diluting concentrated stock human a-thrombin (4270 u/ml) into barbital buffered saline, pH 7.35 to achieve a 10× concentrated working stock. The final concentration of thrombin to be used in standard assays was determined by testing serial dilutions of concentrated stock a-thrombin for its ability to produce a clotting time of 20 sec±0.5 sec. in control platelet poor plasma samples. Platelet poor plasma was prepared as described in Example 4A, and prewarmed at 37° in 0.18 ml aliquots. Test compounds or saline were added to the plasma samples to produce a final volume of 0.2 ml. The reaction was initiated by addition of 10 μl of 10-fold concentrated stock purified human a-thrombin to each sample. Incubation was continued at 37° with gentle sweeping of each sample with a wire loop 2 times per second, until a clot formed in the loop. Time to clot formation was recorded for all samples.

H. Platelet Aggregation

Blood samples were drawn with a plastic syringe and transferred to plastic test tubes containing a sufficient volume of sodium citrate to produce a final concentration of 0.011M sodium citrate in the sample. Samples of platelet rich plasma (PRP) and platelet poor plasma (PPP) were prepared from each sample by first centrifuging the sample at 150×g for 5 minutes at room temperature and collecting the red blood cell free supernatant (PRP), then centrifuging the remaining blood at 1500×g for 15 minutes to obtain the PPP supernatant. PRP and PPP were held in tightly capped plastic tubes until testing. PRP was verified by performing a platelet count and determining that platelet levels were between 200,000 and 300,000 per μl PRP. If necessary, dilution of PRP samples with PPP was made to dilute platelets to this level.

A control 0.5 ml sample of PPP was transferred to an aggregometer cuvette. Several 0.45 ml samples of room temperature PRP were transferred to separate cuvettes. A baseline reading of the PPP sample was obtained by placing the PPP in the aggregometer and incubating at 37° according to aggregometer manufacturer's instructions. A PRP sample was then placed in the aggregometer and allowed to equilibrate for 2 minutes, prior to addition of test reagent contained in 0.05 ml saline. Percent aggregation values were obtained for each sample.

I. Plasmin Assay

Plasmin chromogenic assays were carried out using a standard clinical protocol, at the Stanford University Blood Bank.

J. Heptest

The Heptest assay used was obtained from Haemachem, Inc., St. Louis, Mo. It serves to measure heparin or heparin-like activity as assessed by neutralization of factors Xa and IIa by AT-III, since inhibition of factors Xa and IIa by AT-III is accelerated by heparin. The amount of factor Xa/IIa activity neutralized during a specified time period is directly proportional to the concentration of heparin in the reaction mixture.

Blood was collected in 3.8 trisodium citrate at a ratio of one volume citrate to blood, and processed, as described above to obtain plasma. Factor Xa and Recalmix, each provided in the assay kit, were each reconstituted in 2 ml distilled water and stored according to manufacturer's instructions. Recalmix was pre-warmed at 37° C. for 10 minutes before use. Heparin was diluted in normal human plasma (NHP) for the calibration curve at the following final concentrations in NHP: 1.0 u/ml, 0.5 u/ml, 0.25 u/ml, 0.125 u/ml, 0.06 u/ml, 0.03 u/ml, and 0.

Test plasma (0.1 ml) was added to the fibrocup (pre-warmed at 37° C. for 3 minutes). 0.1 ml factor Xa (room temperature) was then added and the mixture incubated exactly 120 seconds. 0.1 ml Recalmix (kept at 37° C.) was then added and the clotting time was recorded.

K. Chromogenic Anti-IIa (Human) Assay

This assay provides a measurement of absolute heparin concentration or heparin activity, by utilizing its inhibitory effect against human thrombin (IIa), quantitated by a chromogenic substrate for thrombin.

The buffer used in this assay consisted of Tris 50 mM, NaCL 175 nM, EDTA 7.5 mM pH 8.4 at 25° C. The enzyme used was Human thrombin from Ortho Diagnostics (Raritan, N.J.). The enzyme was reconstituted to 10 NIH u/ml (To give a $A_{405}$/min of 0.700 in a FIIa reagent blank.), and stored according to manufacturer's instructions. Substrate used was a substrate specific for thrombin at 1.0 mM, e.g., Chromozym Th, Pentapharm (Basel, Switzerland), or Spectrozyme TH, Diagnostic American or CGS 3447.

Blood from one control male and 1 control female subject was drawn into 3.8% sodium citrate (1 part to 9 parts whole blood by two-syringe butterfly technique, in plastic tube—all laboratory equipment used was plastic). Blood was processed to produce platelet poor plasma, as described above, and pooled. A calibration curve was constructed, using fresh plasma pool and heparin used in experimental model or patient.

400 μl buffer, and 25 μl plasma sample with added test compound or calibration standard were mixed together. The samples were prewarmed to 37° C. for about 1 minute and 25 μl human thrombin was added. The mixture was incubated 1 minute at 37° C. Substrate (50 μl) was then added and the sample was placed in a spectrophotometer for determination of absorbance at 405 nm. $A_{405}$/min. at 37° C. for each calibration standard and plasma sample was recorded, and a calibration graph was prepared for determination of unknown activity. Alternatively, it is possible to calculate % IIa inhibition using the following equation:

$$100\% \left[ \frac{\text{OD sample}}{\text{OD plasma blank}} \times 100\% \right] = \% \text{ F IIa inhibition}$$

Results of studies in which this assay was used are shown in Table 14.

L. Chromogenic Anti-Xa (Bovine) Assay

This assay provides a measurement of absolute heparin concentration or heparin activity utilizing its inhibitory effect against bovine factor Xa, quantitated by a chromogenic substrate for factor Xa. The buffer used in this assay consisted of Tris 50 mM, NaCL 175 mM, pH 8.4 at 25° C. The enzyme is Bovine factor Xa from Stago Diagnostica (Asnieres, France), or Enzyme Research Laboratories (South Bend, Ind.). The enzyme is reconstituted to 5 nkat/ml (To give a $A_{405}$/min. of 0.700 in a FXa reagent blank) and stored according to manufacturer's instructions. Substrate is any substrate specific for factor Xa at 2.5 mM, e.g., CBS 31.39 from Stago Diagnostica.

Blood from one control male and 1 control female subject was drawn into 3.8% sodium citrate (1 part to 9 parts whole blood by two-syringe butterfly technique, in plastic tube—all laboratory equipment used was plastic). Blood was processed to produce platelet poor plasma, as described above, and pooled. A calibration curve was constructed, using fresh plasma pool and heparin used in experimental model or patient.

375 μl buffer and 25 μl plasma sample containing test compound or derived from subject to which test compound has been administered, or calibration standard were mixed together. The mixture was incubated 2 minutes at 37° C., then 50 μl bovine factor Xa was added. The mixture was incubated 2 minutes at 37° C. prior to addition of 50 μl substrate. Absorbance at 405 nm was measured at 37° C. over time to determine $A_{405}$/min. for each calibration standard and plasma sample.

Percent inhibition of Factor IIA was determined graphically or by using the following equation:

$$100\% \left[ \frac{\text{OD sample}}{\text{OD plasma blank}} \times 100\% \right] = \% \text{ F Xa inhibition}$$

Results of studies in which this assay was used are reported in Table 14.

M. Fibrinopeptide A generation test (FPAGT)

The fibrinopeptide-A generation test (FPAGT) is used to examine the test compounds. 0.625–5.0 ug/ml concentrations of the test compounds are supplemented to pooled normal human platelet poor plasma. Thromboplastin C (Dade PT reagent) is standardized in a prothrombin time assay to achieve consistent and measurable amounts of FPA. The standardization is accomplished by diluting the Thromboplastin-C in 0.025M $CaCl_2$ to obtain a PT value of about 35 seconds for citrated human plasma. FPA generation is initiated by adding 100 ul of the standardized thromboplastin to 400 ul of test plasma. Control FPA generation is measured by adding 100 ul of saline to 400 ul of test plasma. After 2 minutes, 100 ul of inhibitor cocktail containing 10 mg/ml EDTA, 500 KIU/ml aprotinin, 1 ug/ml indomethecin (Merk Sharpe and Dohme, Philadelphia, Pa.) and a thrombin inhibitor 5 antithrombin U/ml is added to the mixture. The plasma is then treated with bentonite (2:1 bentonite to plasma) mixed well and centrifuged. The supernatant is then be assayed for FPA using an ELISA Kit (Stago, Asnieres, France), using manufacturer's instructions. This kit relies on competitive binding between labeled and unlabeled fibrinopeptide-A to polyclonal antibodies.

The FPAGT is performed identically in platelet-rich, and antithrombin III-deficient plasma.

A whole blood system for the FPAGT is also utilized. The test is performed as follows: 12×75 non-siliconized glass tubes are washed with saline, marked at a 2.0 ml level and supplemented with 100 ul of an appropriate concentration of heparin or test compound. Blood is drawn from normal human volunteers using a double-syringe technique. After discarding the first 2–3 ml's, the whole blood will be immediately added to the tubes and filled up to the 2.0 ml mark. FPA generation is allowed to proceed for exactly 2 minutes. At the end of the 2 minutes, 200 μl of the inhibitor cocktail previously described is added to prevent further FPA generation. Plasma is obtained by centrifugation, treated with bentonite, recentrifuged and assayed as before.

EXAMPLE 5

Effect of macrocyclic compounds on plasma recalcification (clotting time)

Venous blood samples were collected from rat tail vein into tubes containing sodium citrate (8%), and plasma was prepared, using procedures described in Example 1A. Recalcification of plasma was carried out, as described in Example 1D in a total volume of 0.125 ml. To 50 μl plasma was added 50 μl saline or compound dissolved in saline. Plasma recalcification was initiated by addition of 25 μl 1% (wt/vol) calcium chloride. Effects of these studies are shown in Table 3, in which each compound was tested at a final concentration of 12.5, 25, and 50 μg/ml. Clotting time values are expressed as heparin equivalent weights, in micrograms. 1 USP unit=6.4 μg heparin.

EXAMPLE 6

Effect of increasing concentrations of KY-1, Y-1 and Y-49 on Prothrombin Time (PT) in vitro KY-1, Y-1 and Y-49 were tested in a PT assay using platelet poor plasma prepared from human blood, similar to that described in Example 4B. In this assay, plasma samples (0.1 ml) were pre-mixed with 10 μl saline containing varying amounts of test compound (0–250 μg/ml, final concentrations). The resulting mixed aliquots were forcibly added to tubes containing 0.2 ml pre-warmed (37°) Thromboplastin-calcium reagent (Dade® Thromboplastin•C, Baxter Healthcare Corp., Hayward, Calif.). Each tube was timed individually for clot formation while subjected to gentle mixing, using the manual tilt tube method. Time to clot formation was recorded as PT for each sample.

EXAMPLE 7

Effect of KY-1, Y-49 and Y-1 on APTT

KY-1, Y-1 and Y-49 were tested in an APTT assay using platelet poor plasma prepared from human blood, similar to that described in Example 4C. Plasma samples were collected as described in Example 4A. Plasma samples (0.1 ml) were pre-mixed with 0–364 μg of test compound in 10 μl saline. The mixed samples were added to 0.1 ml of APTT reagent (Automated APTT®, Organon Teknika Corp., Durham, N.C.), prior to addition of 0.2 ml 0.025M calcium chloride, pre-warmed to 37° on a fibrometer plate. The sample was timed for formation of fibrin web.

EXAMPLE 8

Effect on KY-1, Y-49 and Y-1 on Thrombin Time (TT)

Compounds were tested for effects on thrombin time (TT). Platelet poor human plasma was prewarmed at 37° in 0.18 ml aliquots in the presence of 20 μl of test compound (0–190 μg/ml final concentration). The reaction was initiated by addition of 10 μl (42 u/ml) purified human a-thrombin (amount calibrated to give a TT of 20 sec. in untreated human platelet poor plasma). Time to clot formation was recorded for all samples.

EXAMPLE 9

Reptilase Assay (Atroxin Time)

Samples of human platelet poor plasma (0.2 ml) were incubated at 37° with 10 μl aliquots of saline containing test compound (final concentration, 0–900 μg/ml) for 5 minutes. ATROXIN® (Sigma Chemical Co., St. Louis, Mo.), prewarmed to 37°, was added as a 0.1 ml aliquot to each sample tube to initiate the reaction. Time to clotting was recorded as Atroxin time.

EXAMPLE 10

Effect on KY-1 and Y-1 on Plasmin Activity

Figure 37C:
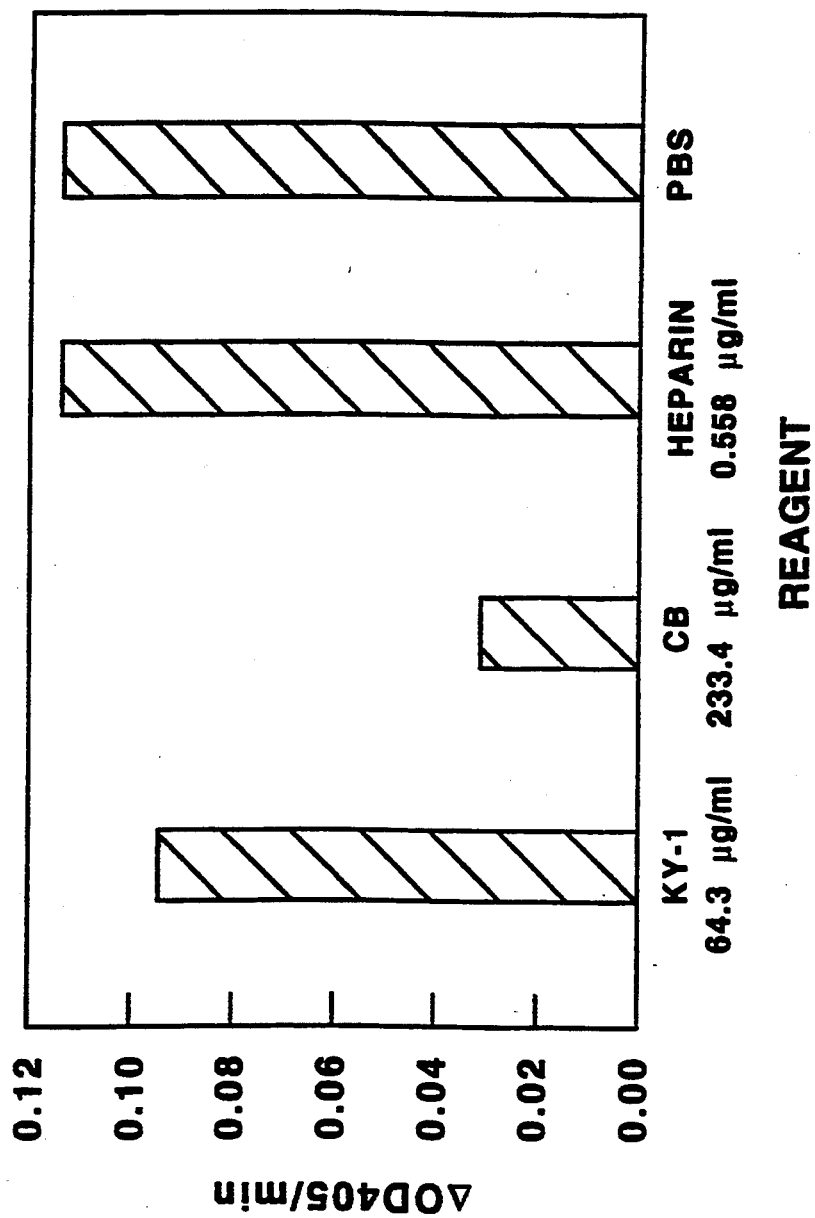

KY-1 and Y-1 were tested for effects on plasmin chromogenic activity. KY-1 was tested at concentrations of 20.3, 40.6, and 81.1 μg/ml final concentration, and Y-1 was tested at final concentrations of 9.4 and 18.8 μg/ml. By way of comparison, heparin was tested at a final concentration of 0.41 μg/ml. Results are shown in FIGS. 37A–C.

EXAMPLE 12

Effect of intravenous administration of macrocyclic compounds on PT, APTT and fibrinogen content of rat plasma Macrocyclic compounds at various concentrations were dissolved in phosphate buffered saline (pH 7.4) and administered to rates at 2.5, 0.5, or 25 mg/kg, intravenously. At various times after administration, a blood sample was taken from each rat, plasma prepared, as described in Example 4A, and determinations of PT, APTT, and fibrinogen content made, as described in Examples 4B, 4C and 4E, respectively.

EXAMPLE 13

Effect of oral Y-1 on Plasma Clotting Time

Female Swiss-Webster mice (27″28 g each) were each given 2 doses (500 or 625 mg/kg) of compound or saline (PBS) at 30 minute intervals by gastric gavage. Blood samples were collected into 8% citrate via retroorbital venipuncture 2.5 hours following the initial dosing. Blood plasma was obtained, processed as described in Example 4A, and assayed for plasma clotting time as described in Example 5. For comparison, Y-1 (12 or 20 μg/ml) was added to plasma samples from saline treated control animals, and samples were tested similarly for clotting time. Results of this assay are shown in Table 4.

EXAMPLE 14

Time course of effect of orally administered Y-1 on PT and APTT

Rates were given Y-1 at a dose of 450 mg/kg by gastric gavage. Arterial blood samples were withdrawn at 0.5, 4, 8, 16, and 24 hours through a cannula inserted in the left carotid artery, with tip extending to the descending aorta. Plasma samples were prepared as described in Example 4A, and tested for PT and APTT, as described in Examples 4B and 4C. An additional dose of 225 mg/kg was administered to a subgroup of animals 23 hours after the initial dosing, and plasma from these animals was also tested at 24 hours. Results are shown in Table 6.

EXAMPLE 15

Effect of intravenous Y-1 on PT and APTT

Male Sprague-Dawley rats (2/dose) were given 2.5 mg/kg or 5 mg/kg Y-1 intravenously in the lateral tail vein. At various time intervals following injection, rats (4/time period) were bled through a cannula inserted in the carotid artery to the descending aorta, and the blood was processed to obtain plasma, as described in Example 4A. An APTT assay was carried out on each plasma sample.

EXAMPLE 16

Effect of KY-1, Y-1, and Y-49 on Platelet Aggregation

General platelet aggregation assay procedures were used as described in Example 4I. Collagen dose was titrated to give maximal response to platelet aggregation using citrated platelet-rich plasma. KY-1 and Y-49 at 24 μg/ml and 48 μg/ml concentrations had no effect on collagen-induced aggregation (0.47 μg/ml). Y-1 at 24 μg/ml had a slight inhibitory effect while at 48 μg/ml showed significant inhibition.

EXAMPLE 17

Rabbit model of Stasis Thrombosis

New Zealand White rabbits (2, 5-3, 0 kg) were obtained from Langshaw farms (Augusta, Mich.) and were exposed to a regular 12 hour light/dark cycle. The rabbits were fed a standard diet of Wayne Rabbit Ration and allowed free access to water.

White New Zealand male rabbits were anesthetized with intramuscular injections of xylazine (20 mg/kg; ROMPUN ®, Bayvet division of Miles Labs, Shawnee, Kans.) and ketamine (80 mg/kg; KETALAR ®, Parke Davis, Morris Plains, N.J.). After induction of anaesthesia, the rabbits were weighed and prepared for surgery. Baseline blood samples were taken at that time. The surgical procedure entailed isolation of both right and left jugular vein segments. To minimize trauma and to ensure hemostasis, battery operated cauterizes were used in the surgical procedures. After isolating the jugular vein segments, the test compounds were injected by intravenous route through a marginal ear vein.

At the appropriate time, a thrombogenic challenge of KONYNE ® brand of prothrombin complex concentrate (PCC; Cutter Labs, Berkeley, Calif.), 25 U/kg followed by 0.01 U/kg Russel's viper venom (RVV) in cephalin (Sigma, St. Louis, Mo.), was administered through the marginal ear vein and allowed to circulate for exactly 20 seconds. The isolated jugular vein segments were ligated and stasis produced. Blood samples drawn through a carotid catheter for ex vivo analysis, were taken immediately prior to and after injection of the thrombogenic challenge. After exactly 5, 10, or 20 minutes of stasis time (as indicated in Table 8 and Table 9), the isolated segments were removed and examined for blood clots in a saline filled petri dish. Clot formation was visually grade using a ± system. In this system, "−" represents blood only with no evidence of clotting, "+" indicates some small clots but mostly blood, "++" indicates mostly small but some medium clots, "+++" indicates a large clot with some blood, while "++++" indicates a fully formed, casted clot with no blood. In order to analyze the data, the ± grades were be transformed into numerical values using the following scale:

```
     −    = 0
     +    = 1.25
    ++    = 2.5
   +++    = 5.0
  ++++    = 10.0
```

After transformation, mean values were determined from the average of the left and right stasis scores.

Drugs were compared in 10 animals for each route of injection and concentration. Results are shown in Table 8 and Table 9.

EXAMPLE 18

Modified Rabbit Ear Bleeding Model

Rabbits were anesthetized using 10 mg/kg ROMPUM and 80 mg/kg KETALAR. The rabbit's ear was then immersed in a saline bath at 37° C. Using transillumination, an area was selected that was free of major blood vessels. Using a Bard-Parker Knife, five uniform incisions of full thickness were made. Immediately thereafter, the rabbit's ear was immersed in the saline bath at 37° C. for 10 minutes. After 10 minutes, the saline was collected in a bottle and the total red cells were counted using a Coulter cell counter.

It is claimed:

1. A method of inhibiting thrombus formation in a mammalian subject, comprising
   administering to the subject a therapeutically effective dose of calix(n)arene compound which is derivatized, at its ring positions meta to the bridge attachments to the ring, with polar substituents having terminal sulfonate groups.

2. The method of claim 1, wherein the number of subunits in the compound (n) is 4–10.

3. The method of claim 1, wherein the calix(n)arene compound is partially oxidized.

4. The method of claim 1, wherein the compound is administered orally.

5. The method of claim 1, wherein the calix(n)arene compound has the general structure:

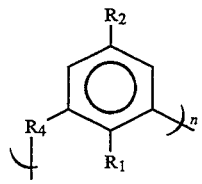

wherein
   (a) $n=4, 6$, or 8;
   (b) $R_1$ is OH, $=$O, or a combination thereof;
   (c) $R_2$ has the form: $(CH_2)_m R_2'$, where $m=1-3$, and $R_2'$ is a sulfonate group;
   (d) $R_4$ is $>CH_2$, $\geq CH$, or a combination thereof.

6. The method of claim 5, wherein $R_2'$ is $-SO_3^-$.

7. A method of inhibiting thrombus formation in a mammalian subject, comprising
   administering to the subject a therapeutically effective dose of a calix(n)arene compound having the general structure:

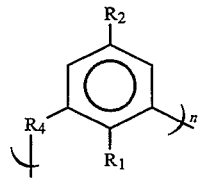

wherein
   (a) $n=4, 6$, or 8;
   (b) $R_1$ is OH, $=$O, or a combination thereof;
   (c) $R_2$ has the form: $(CH_2)_m R_2'$, where $m=1-3$, and $R_2'$ is a sulfonate group;
   (d) $R_4$ is $>CH_2$, $\geq CH$, or a combination thereof.

8. The method of claim 7, wherein $R_2'$ is $-SO_3^-$.

9. The method of claim 7, wherein the compound is administered orally.

* * * * *